US012662702B2

(12) United States Patent
Mandell et al.

(10) Patent No.: US 12,662,702 B2
(45) Date of Patent: Jun. 23, 2026

(54) SEQUENCING POLYNUCLEOTIDES USING NANOPORES

(71) Applicant: ILLUMINA, INC., San Diego, CA (US)

(72) Inventors: Jeffrey Mandell, Rancho Santa Fe, CA (US); Jessica Killian, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 877 days.

(21) Appl. No.: 17/947,877

(22) Filed: Sep. 19, 2022

(65) Prior Publication Data

US 2023/0090867 A1 Mar. 23, 2023

Related U.S. Application Data

(60) Provisional application No. 63/247,155, filed on Sep. 22, 2021.

(51) Int. Cl.
*C12Q 1/6869* (2018.01)
*C12Q 1/70* (2006.01)
(Continued)

(52) U.S. Cl.
CPC ........... *C12Q 1/6869* (2013.01); *C12Q 1/701* (2013.01); *G01N 27/3276* (2013.01);
(Continued)

(58) Field of Classification Search
CPC .................................................. C12Q 1/6869
See application file for complete search history.

(56) References Cited

U.S. PATENT DOCUMENTS

| | | | |
|---|---|---|---|
| 5,432,272 A | 7/1995 | Benner | |
| 5,795,782 A | 8/1998 | Church et al. | |

(Continued)

FOREIGN PATENT DOCUMENTS

| | | | | |
|---|---|---|---|---|
| EP | 3955002 A1 | 2/2022 | | |
| GB | 2590846 A | * 7/2021 | ....... | G01N 33/48721 |

(Continued)

OTHER PUBLICATIONS

Deamer et al.Three decades of nanopore sequencing. Nat Biotechnol. May 6, 2016;34(5):518-24. doi: 10.1038/nbt.3423. PMID: 27153285; PMCID: PMC673352; cited as NPL # 10 in IDS filed Dec. 29, 2022 (Year: 2016).*

(Continued)

Primary Examiner — Aaron A Priest
Assistant Examiner — Tian Nmn Yu
(74) Attorney, Agent, or Firm — Sheppard, Mullin, Richter & Hampton LLP; Jaime D. Choi

(57) ABSTRACT

Sequencing polynucleotides using nanopores is provided herein. A polynucleotide is disposed through a nanopore's aperture such that its 3' end is on the nanopore's first side and its 5' end is on the nanopore's second side. On the nanopore's first side, a duplex with the polynucleotide is formed that includes a 3' end. The duplex is extended on the first side of the nanopore by adding a nucleotide to the 3' end of the duplex. A first force is applied disposing the 3' end of the duplex within the aperture, and the nanopore inhibits translocation of the 3' end of the duplex to the second side of the nanopore. A value of an electrical property of the 3' end of the duplex and a single-stranded portion of the polynucleotide is measured. The nucleotide at the 3' end of the duplex is identified using the measured value.

32 Claims, 30 Drawing Sheets

Specification includes a Sequence Listing.

(51) Int. Cl.
| | | |
|---|---|---|
| *G01N 27/327* | (2006.01) | |
| *G01N 27/447* | (2006.01) | |
| *G01N 33/487* | (2006.01) | |

(52) U.S. Cl.
CPC . *G01N 27/44791* (2013.01); *G01N 33/48721* (2013.01); *C12Q 2565/631* (2013.01)

(56) References Cited

U.S. PATENT DOCUMENTS

| | | | |
|---|---|---|---|
| 6,150,510 | A | 11/2000 | Seela et al. |
| 6,329,178 | B1 | 12/2001 | Patel et al. |
| 6,362,002 | B1 | 3/2002 | Denison et al. |
| 6,395,524 | B2 | 5/2002 | Loeb et al. |
| 6,602,695 | B2 | 8/2003 | Patel et al. |
| 6,936,433 | B2 | 8/2005 | Akeson et al. |
| 7,170,050 | B2 | 1/2007 | Turner et al. |
| 7,238,485 | B2 | 7/2007 | Akeson et al. |
| 7,476,503 | B2 | 1/2009 | Turner et al. |
| 8,143,030 | B2 | 3/2012 | Maxham et al. |
| 8,153,375 | B2 | 4/2012 | Travers et al. |
| 8,324,914 | B2 | 12/2012 | Chen et al. |
| 8,500,982 | B2 | 8/2013 | Akeson et al. |
| 8,628,940 | B2 | 1/2014 | Sorenson et al. |
| 8,652,779 | B2 | 2/2014 | Turner et al. |
| 8,679,747 | B2 | 3/2014 | Olasagasti et al. |
| 8,828,208 | B2 | 9/2014 | Canas et al. |
| 8,986,928 | B2 | 3/2015 | Turner et al. |
| 9,116,118 | B2 | 8/2015 | Turner et al. |
| 9,121,059 | B2 | 9/2015 | Davis et al. |
| 9,395,353 | B2 | 7/2016 | Gu et al. |
| 9,481,908 | B2 | 11/2016 | Olasagasti et al. |
| 9,588,079 | B2 | 3/2017 | Gundlach et al. |
| 9,678,056 | B2 | 6/2017 | Turner et al. |
| 9,708,655 | B2 | 7/2017 | Mandell et al. |
| 9,732,379 | B2 | 8/2017 | Gu et al. |
| 9,738,929 | B2 | 8/2017 | Turner et al. |
| 10,059,988 | B2 | 8/2018 | Akeson et al. |
| 10,202,645 | B2 | 2/2019 | Akeson et al. |
| 10,364,462 | B2 | 7/2019 | Stava et al. |
| 10,436,747 | B2 | 10/2019 | Lieber et al. |
| 10,788,451 | B2 | 9/2020 | Brown et al. |
| 10,920,271 | B2 | 2/2021 | Davis et al. |
| 11,049,588 | B2 | 6/2021 | Van Rooyen et al. |
| 11,150,216 | B2 | 10/2021 | Chen et al. |
| 2007/0048748 | A1 | 3/2007 | Williams et al. |
| 2010/0035260 | A1* | 2/2010 | Olasagasti ........... C12Q 1/6869 |
| | | | 435/6.16 |
| 2018/0155774 | A1* | 6/2018 | Gunderson .......... C12Q 1/6869 |
| 2019/0136307 | A1 | 5/2019 | Predki et al. |
| 2019/0256904 | A1 | 8/2019 | Davis et al. |
| 2019/0310242 | A1 | 10/2019 | Reid et al. |
| 2020/0080966 | A1 | 3/2020 | Reid et al. |
| 2020/0115745 | A1 | 4/2020 | Ju et al. |
| 2020/0309761 | A1 | 10/2020 | Massingham et al. |
| 2021/0313009 | A1 | 10/2021 | Ruehle |
| 2022/0106629 | A1 | 4/2022 | Hong et al. |
| 2023/0090867 | A1 | 3/2023 | Mandell et al. |

FOREIGN PATENT DOCUMENTS

| | | | |
|---|---|---|---|
| WO | 9202258 | A1 | 2/1992 |
| WO | 9310820 | A1 | 6/1993 |
| WO | 9422892 | A1 | 10/1994 |
| WO | 9424144 | A2 | 10/1994 |
| WO | 2008124107 | A1 | 10/2008 |
| WO | 2009037473 | A2 | 3/2009 |
| WO | 2011/106456 | A2 | 9/2011 |
| WO | 2011/106459 | A2 | 9/2011 |
| WO | 2012/033524 | A2 | 3/2012 |
| WO | 2013/019759 | A1 | 7/2012 |
| WO | 2012166742 | A1 | 12/2012 |
| WO | 2015150786 | A1 | 10/2015 |
| WO | 2015166276 | A1 | 11/2015 |
| WO | 2015187670 | A2 | 12/2015 |

| | | | |
|---|---|---|---|
| WO | 2016100749 | A1 | 6/2016 |
| WO | 2016196755 | | 8/2016 |
| WO | 2020/044780 | A1 | 7/2019 |
| WO | 2019234432 | A1 | 12/2019 |
| WO | 2020/168286 | A1 | 8/2020 |
| WO | 2021/099801 | A1 | 5/2021 |
| WO | 2021/240761 | A1 | 12/2021 |
| WO | 2021/255477 | A1 | 12/2021 |

OTHER PUBLICATIONS

Vercoutere et al.; Discrimination among individual Watson-Crick base pairs at the termini of single DNA hairpin molecules, Nucleic Acids Research, vol. 31, Issue 4, Feb. 15, 2003, pp. 1311-1318, doi.org/10.1093/nar/gkg218 (Year: 2003).*

Wang et al. Fast and precise detection of DNA methylation with tetramethylammonium-filled nanopore. Sci Rep 7, 183 (2017). doi.org/10.1038/s41598-017-00317-2 (Year: 2017).*

Ashkenasy et al., "Recognizing a Single Base in an Individual DNA Strand: A Step Toward Nanopore DNA Sequencing," Angew Chem Int Ed Engl.; 44(9): 1401-1404 (2005).

Benner et al., Sequence-specific detection of individual DNA polymerase complexes in real time using a nanopore, Nat Nanotechnol; 2(11): 718-724 (2007).

Butler, "Nanopore Analysis of Nucleic Acids," University of Washington; UMI Microform 3265304 (2007).

Cherf et al., "Automated forward and reverse ratcheting of DNA in a nanopore at 5-Åprecision," Nat Biotechnol 30, 344-348 (2012) https://doi.org/10.1038/nbt.2147.

Chu et al., "Real-Time Monitoring of DNA Polymerase Function and Stepwise Single-Nucleotide DNA strand Translocation through a Protein Nanopore," Angew Chem Int Ed Engl.; 49(52): 10106-10109 (2010) doi:10.1002/anie.201005460.

Cockroft et al., "A Single-Molecule Nanopore Device Detects DNA Polymerase Activity with Single-Nucleotide Resolution," J. Am. Chem. Soc.; 130(3): 818-820 (2008)J. Am. Chem. Soc. 2008, 130, 818-820.

Cockroft et al., "A Single-Molecule Nanopore Device Detects DNA Polymerase Activity with Single-Nucleotide Resolution," J. Am. Chem. Soc.; 130(3): 818-820 (2008)J. Am. Chem. Soc. 2008, 130, 818-820 Supplemental Information.

Dahl et al., "Direct observation of translocation in individual DNA polymerase complexes," J Biol Chem.; 287(16):13407-21 (2012) doi: 10.1074/jbc.M111.338418.

Dahl et al., "Dynamics of translocation and substrate binding in individual complexes formed with active site mutants of {phi} 29 DNA polymerase," J Biol Chem.; 289(10):6350-6361 (2014) doi: 10.1074/jbc.M113.535666.

Deamer et al., "Three decades of nanopore sequencing," Nat Biotechnol.; 34(5): 518-524 (2016) doi:10.1038/nbt.3423.

Derrington et al., "Nanopore DNA sequencing with MspA," PNAS; 107(37): 16060-16065 (2010).

Floyd et al., "Analysis of Kinetic Intermediates in Single-Particle Dwell-Time Distributions" Biophysical Journal; 99: 360-366 (2010).

Garalde et al., "Distinct Complexes of DNA Polymerase I (Klenow Fragment) for Base and Sugar Discrimination during Nucleotide Substrate Selection," The Journal of Biological Chemistry; 286(16): 14480-14492 (2011).

Ghadiri et al., "Single DNA Rotaxanes of a Transmembrane Pore Protein," Angew Chem Int Ed Engl.; 43(23): 3063-3067 (2004).

Gyarfas et al., "Mapping the Position of DNA Polymerase-Bound DNA Templates in a Nanopore at 5 ÅResolution," ACS Nano; 3(6): 1457-1466 (2009) https://doi.org/10.1021/nn900303.

Hurt et al., "Specific nucleotide binding and rebinding to individual DNA polymerase complexes captured on a nanopore," 131 J. Am. Chem. Soc. 3772 (2009).

Jain et al., "Improved data analysis for the MinION nanopore sequencer," 12 Nat. Methods 351 (2015).

Jain et al., "The Oxford Nanopore MinION: delivery of nanopore sequencing to the genomics community," Genome Biol 17(239): 1-11 (2016) https://doi.org/10.1186/s13059-016-1103-0.

Jain, M., "High-Coverage Long Read DNA Sequencing with the Oxford Nanopore MinION," (dissertation) (2017).

(56)　　　　　　References Cited

OTHER PUBLICATIONS

Langford et al., "Unsupported planar lipid membranes formed from mycolic acids of *Mycobacterium tuberculosis*," J. Lipid Rsrch.; 52: 272-277 (2011).

Laszlo et al., "Detection and mapping of 5-methylcytosine and 5-hydroxymethylcytosine with nanopore MspA," PNAS; 110(47): 18904-18909 (2013).

Lieberman et al., "Dynamics of the translocation step measured in individual DNA polymerase complexes," J. Am. Chem. Soc.; 134: 18816 (2012).

Lieberman et al., "Kinetic mechanism of translocation and dNTP binding in individual DNA polymerase complexes," J. Am. Chem. Soc.; 135(24): 9149-9155 (2013).

Lieberman et al., "Processive replication of single DNA molecules in a nanopore catalyzed by phi29 DNA polymerase," J. Am. Chem. Soc.; 132: 17961 (2010).

Manrao et al., "Reading DNA at single-nucleotide resolution with a mutant MspA nanopore and phi29 DNA polymerase," Nat Biotechnol; 30: 349-353 (2012) https://doi.org/10.1038/nbt.2171.

Noakes et al., "Increasing the accuracy of nanopore DNA sequencing using a time-varying cross membrane voltage," Nat Biotechnol; 37: 651-656 (2019). https://doi.org/10.1038/s41587-019-0096-0.

Olasagasti et al., "Replication of Individual DNA Molecules under Electronic Control Using a Protein Nanopore," Nat Nanotechnol; 5(11): 798-806 (2010) doi:10.1038/nnano.2010.177.

Shreiber et al., "Error rates for nanopore discrimination among cytosine, methylcytosine, and hydroxymethylcytosine along individual DNA strands," Proc. Nat'l Acad. Sci. U.S.A.; 110: 18910-5 (2013).

Wilson et al., "Electronic control of DNA polymerase binding and unbinding to single DNA molecules," Am. Chem. Soc. Nano; 3: 995-1003 (2009).

Wyatt et al., "The bases of the nucleic acids of some bacterial and animal viruses: the occurrence of 5-hydroxymethylcytosine," Biochem, 55, pp. 179-180, 1953.

Josse et al., "Glucosylation of deoxyribonucleic acid," J. Biol. Chem., 237(6), pp. 1968-1976, 1962.

Horowitz et al.,"Mapping of N6-methyladenosine residues in bovine prolactin mRNA," Proc Natl Acad Sci USA, 81 (18), pp. 5667-5671, 1984.

Buncel et al., "Metal ion-biomolecule interactions>XII, 1H and 13C NMR evidence for the preferred reaction of thymidine over guanosine in exchange and competition reactions with mercury(II) and methylmercury(II)," Inorg Biochem, 25, pp. 61-73, 1985.

Narayan et al., "Unequal distribution of N6-mehntyladenosine in influenza virus mRNAs," Mol Cell Biol 7(4), pp. 1572x-1575, 1987.

Singer, "Alkyl bases, Nucleosides, and Nucleotides: UV spectral characteristics and acidic dissociation constants of 280 alkyl bases, nucleosides, and nucleotides," in Fasman ed., Practical Handbook of Biochemistry and Molecular Biology, CRC Press, Boca Raton, United States, pp. 385-394, 1989.

Lee et al., "A cooperative conformational change in duplex DNA induced by Zn2+ and other divalent metal ions," Biochem Cell Biol 71, pp. 162-168, 1993.

Limbach et al., "Summary: the modified nucleosides of RNA," Nucl. Acids Res. 22(12), pp. 2183-2196, 1994.

Matray et al., "A specific partner for abasic damage in DNA," Nature 399(6737), pp. 704-708, 1999.

Mccullough et al., "Initiation of base excision repair: glycosylase mechanisms and structures," Annual Rev of Biochem 68, pp. 255-285, 1999.

Zimmerman et al., "A novel silver(I)-mediated DNA base pair," J Am Chem Soc 124(46), pp. 13684-13685, 2002.

Wettig et al., "Thermodynamic investigation of M-DNA: a novel metal ion-DNA complex," J Inorg Biochem, 94, pp. 94-99, 2003.

Liu et al., "A four-base paired genetic helix with expanded size," Science, 302(5646), pp. 868-871, 2003.

Zimmerman et al., "A second-generation copper(II)-mediated metallo-DNA-base pair," Bioorg Chem 32(1), pp. 13-25, 2004.

Ono et al., "Highly selective oligonucleotide-based sensor for mercury (II) in aqueous solutions," Angew Chem, 43, pp. 4300-4302, 2004.

Lariviere et al., "Structural evidence of a passive base-flipping mechanism for ?-glucosyltransferase," J. Biol. Chem. 279(33), pp. 34715-34720, 2004.

Johnson et al., "A third base pair for the polymerase chain reaction: inserting isoC and isoG," 32(6), pp. 1937-1941, 2004.

Clever et al., "A highly DNA-duplex-stabilizing metal-salen base pair," Angew Chem Int Ed, 44, pp. 7204-7208, 2005.

Petersson et al., "Crystal structure of a partly self-complementary peptide nucleic acid (PNA) oligomer showing a duplex-triplex network," J Am Chem Soc 127(5), pp. 1424-1430, 2005.

Ahle et al., "Sequence determination of nucleic acids containing 5-methylisocytosine and isoguanine: identification and insight into [polymerase replication of the non-natural nucleobases," Nucleic Acids Res 33(10), pp. 3176-3184, 2005.

Kimoto et al., "Fluorescent probing for RNA molecules by an unnatural base-pair system," Nucleic Acids Res. 35(16), pp. 5360-5369, 2007.

Krueger et al., "Model systems for understanding DNA base pairing," Curr Opinions in Chem Biology, 11(6), pp. 588-594, 2007.

Yanagida et al., "Preparation of DNA double helical structures containing both mercury and silver ions," Nucleic Acids Symp Ser, 51, pp. 179-180, 2007.

Ooi et al., "The colorful history of active DNA demethylation," Cell 133, pp. 1145-1148, 2008.

Everts, "RNA's Outfits: The nucleic acid has dozens of chemical costumes," C&EN, 87(36), pp. 65-68, 2009.

Kriaucionis et al., "The nuclear DNA base, 5-hydroxymethylcytosine is present in brain and enriched in Purkinje neurons," Science, 324(5929), pp. 929-930, 2009.

Krueger et al., "Redesigning the architecture of the base pair:toward biochemical and biological function of new genetic sets," Chemistry & Biology 16(3), pp. 242-248, 2009.

Loakes et al., "Polymerase engineering: towards the encoded synthesis of unnatural biopolymers," Chem Commun, pp. 4619-4631, 2009.

Schlegel et al., "Metal-mediated base pairing within the simplified nucleic acid GNA," Org Biomol Chem 7(3), pp. 476-482, 2009.

Seo et al., "Optimization of an unnatural base pair towards natural-like replication," J Am Chem Soc, 131(9), pp. 3246-3252, 2009.

Tahiliani et al., "Conversion of 5-methylcytosine to 5-hydroxymethylcytosine in mammalian DNA by NLL partner TET1," Science 324(5929), pp. 930-935, 2009.

Yoon, "Hidden Markov models and their applications in biological sequence analysis," Current Genomics, 10(6), pp. 402-415, 2009.

Carr et al., "Towards in situ sequencing for life detection," 2017 IEEE Aerospace Conference, Big Sky, MT, USA, 2017, pp. 1-18, doi: 10.1109/AERO.2017.7943896.

Goodwin et al., "Coming of Age: Ten Years of Next Generation Sequencing Technologies," Nature Reviews Genetics; 17(6): 333-351 (2016).

International Search Report and Written Opinion for PCT/US2022/044105 dated Apr. 18, 2023; 22 pages.

International Search Report and Written Opinion for PCT/US2022/076673 dated Mar. 16, 2023; 23 pages.

Laszlo et al., "Decoding long nanopore sequencing reads of natural DNA," Nat Biotechnol. Aug. 2014;32(8):829-33. doi: 10.1038/nbt.2950. Epub Jun. 25, 2014. PMID: 24964173; PMCID: PMC4126851 (Year: 2014).

Ding et al., "Differentiation of G:C vs A:T and G:C vs G:mC Base Pairs in the Latch Zone of a-Hemolysin," ACS Nano. Nov. 24, 2015;9(11):11325-32. doi: 10.1021/acsnano.5b05055. Epub Oct. 27, 2015. PMID: 26506108; PMCID: PMC4876701 (Year: 2015).

Yuen et al., "Systematic benchmarking of tools for CpG methylation detection from nanopore sequencing," Nat Commun 12, 3438 (2021). Published: Jun. 8, 2021 (Year: 2021).

* cited by examiner

Raw Data

Level Means

SEQUENCE LISTING

```
Sequence total quantity: 6
SEQ ID NO: 1              moltype = DNA   length = 27
FEATURE                  Location/Qualifiers
source                   1..27
                         mol_type = other DNA
                         organism = synthetic construct
SEQUENCE: 1
tttttacat tttttacatt ttttacg                              27

SEQ ID NO: 2              moltype = DNA   length = 27
FEATURE                  Location/Qualifiers
source                   1..27
                         mol_type = other DNA
                         organism = synthetic construct
```

-continued

```
modified_base            8
                         mod_base = m5c
modified_base            17
                         mod_base = m5c
SEQUENCE: 2
tttttacat tttttacatt ttttacg                                              27

SEQ ID NO: 3            moltype = DNA   length = 12
FEATURE                Location/Qualifiers
source                 1..12
                       mol_type = other DNA
                       organism = synthetic construct
SEQUENCE: 3
gtacgtacgt ac                                                             12

SEQ ID NO: 4           moltype = DNA   length = 13
FEATURE                Location/Qualifiers
source                 1..13
                       mol_type = other DNA
                       organism = synthetic construct
SEQUENCE: 4
cgtacgtacg tac                                                            13

SEQ ID NO: 5           moltype = DNA   length = 18
FEATURE                Location/Qualifiers
source                 1..18
                       mol_type = other DNA
                       organism = synthetic construct
SEQUENCE: 5
tggtcaggtg tttgcgta                                                       18

SEQ ID NO: 6           moltype = DNA   length = 58
FEATURE                Location/Qualifiers
source                 1..58
                       mol_type = other DNA
                       organism = synthetic construct
modified_base          11..13
                       mod_base = OTHER
                       note = abasic site
SEQUENCE: 6
cccccccca nnnagttctg agcaaatagg ctgtgcttta tacgcaaaca cctgacca    58
```

SEQUENCING POLYNUCLEOTIDES USING NANOPORES

CROSS-REFERENCE TO RELATED APPLICATION

This application claims the benefit of U.S. Provisional Patent Application No. 63/247,155, filed Sep. 22, 2021 and entitled "Sequencing Polynucleotides Using Nanopores," the entire contents of which are incorporated by reference herein.

SEQUENCE LISTING

The material in the accompanying sequence listing is hereby incorporated by reference into the application. The accompanying sequence listing XML file, named "G1094_IP_2048_US_85491_02100.xml", was created on Sep. 16, 2022 and is 8 kB in size.

FIELD

This application generally relates to sequencing polynucleotides using nanopores.

BACKGROUND

A significant amount of academic and corporate time and energy has been invested into using nanopores to sequence polynucleotides. For example, the dwell time has been measured for complexes of DNA with the Klenow fragment (KF) of DNA polymerase I atop a nanopore in an applied electric field. Or, for example, a current or flux-measuring sensor has been used in experiments involving DNA captured in a α-hemolysin nanopore. Or, for example, KF-DNA complexes have been distinguished on the basis of their properties when captured in an electric field atop an α-hemolysin nanopore. In still another example, polynucleotide sequencing is performed using a single polymerase enzyme complex including a polymerase enzyme and a template nucleic acid attached proximal to a nanopore, and nucleotide analogs in solution. The nucleotide analogs include charge blockade labels that are attached to the polyphosphate portion of the nucleotide analog such that the charge blockade labels are cleaved when the nucleotide analog is incorporated into a polynucleotide that is being synthesized. The charge blockade label is detected by the nanopore to determine the presence and identity of the incorporated nucleotide and thereby determine the sequence of a template polynucleotide. In still other examples, constructs include a transmembrane protein nanopore subunit and a nucleic acid handling enzyme.

Olasagasti et al., "Replication of individual DNA molecules under electronic control using a protein nanopore," Nature Nanotechnology 5(11): 798-806 (2010) discloses disposing a DNA template through a nanopore. A DNA template-polymerase complex is formed on the first side of an α-hemolysin nanopore, and includes a DNA duplex and a polymerase. The DNA template includes abasic reporter nucleotides that initially are positioned on the second side of the α-hemolysin nanopore. While the polymerase is used to add nucleotides to the duplex based on the sequence of the DNA template, the ionic current through the nanopore is measured ($I_{EBS}$, where EBS refers to the enzyme bound state). As these nucleotides are added, the abasic reporter nucleotides are drawn towards and subsequently through the α-hemolysin, which causes changes in $I_{EBS}$.

However, such previously known compositions, systems, and methods may not necessarily be sufficiently robust, reproducible, or sensitive and may not have sufficiently high throughput for practical implementation, e.g., demanding commercial applications such as genome sequencing in clinical and other settings that demand cost effective and highly accurate operation. Accordingly, what is needed are improved compositions, systems, and methods for sequencing polynucleotides.

SUMMARY

Sequencing polynucleotides using nanopores is provided herein.

Some examples herein provide a method of sequencing a polynucleotide using a nanopore including a first side, a second side, and an aperture extending through the first and second side. The method may include (a) disposing a polynucleotide through the aperture of the nanopore such that a 3' end of the polynucleotide is on the first side of the nanopore, and a 5' end of the polynucleotide is on the second side of the nanopore. The method may include (b) forming a duplex with the polynucleotide on the first side of the nanopore, the duplex including a 3' end. The method may include (c) extending the duplex on the first side of the nanopore by adding a first nucleotide to the 3' end of the duplex. The method may include (d) applying a first force disposing the 3' end of the extended duplex within the aperture. The method may include, while the first force is applied, inhibiting, using the nanopore, translocation of the 3' end of the extended duplex to the second side of the nanopore; and measuring a value of an electrical property of the 3' end of the extended duplex and a single-stranded portion of the polynucleotide. The method may include (e) identifying the first nucleotide using the value measured in operation (d).

In some examples, the value measured in operation (d) includes an electrical current, ionic current, electrical resistance, or electrical voltage drop across the nanopore. In some examples, the value measured in operation (d) includes noise of an electrical current, ionic current, electrical resistance, or electrical voltage drop across the nanopore. In some examples, the value measured in operation (d) includes a standard deviation of the noise.

In some examples, the value measured in operation (d) is at least based on M nucleotides of the single-stranded portion of the polynucleotide and D pairs of hybridized nucleotides of the extended duplex. In some examples, M is greater than or equal to two, and D is greater than or equal to one. In some examples, M is greater than or equal to three. In some examples, D is greater than or equal to two. In some examples, at least one of the M nucleotides of the single-stranded portion includes a modified base, the method including identifying the modified base using the value measured in operation (d). In some examples, the modified base includes a methylated base.

In some examples, the method further includes inhibiting addition of another nucleotide to the 3' end of the extended duplex while the first force is applied in operation (d). In some examples, the nanopore inhibits the addition of another nucleotide.

In some examples, the nanopore is oriented so that the first side of the nanopore includes a majority of the aperture. In some examples, the nanopore is oriented so that the second side of the nanopore includes a majority of the aperture.

In some examples, the method further includes (f) applying a modified first force again disposing the 3' end of the extended duplex within the aperture. The method further may include, while applying the modified first force: inhibiting, using the nanopore, translocation of the 3' end of the extended duplex to the second side of the nanopore; and measuring a value of an electrical property of the 3' end of the extended duplex and a single-stranded portion of the polynucleotide. The method further may include (g) identifying the first nucleotide using the value measured in operation (f).

In some examples, the first nucleotide is added using a polymerase in contact with the 3' end of the duplex. In some examples, the method further may include reversibly inhibiting the polymerase from adding a second nucleotide to the 3' end of the extended duplex. In some examples, a blocking moiety reversibly inhibits the polymerase from adding the second nucleotide to the 3' end of the extended duplex. In some examples, the first nucleotide is coupled to the blocking moiety. In some examples, the blocking moiety includes a 3'-blocking group. In some examples, the blocking moiety is reversibly associated with the extended duplex. In some examples, the method further includes detecting association of the blocking moiety with the extended duplex. In some examples, the method further includes detecting absence of the blocking moiety from the extended duplex. In some examples, the method further includes removing the blocking moiety to allow the polymerase to add the second nucleotide to the 3' end of the extended duplex.

In some examples, the first force applied in (d) removes the polymerase from contact with the 3' end of the extended duplex. In some examples, the method includes including applying a second force to remove the polymerase from contact with the 3' end of the extended duplex, wherein second force is greater than the first force.

In some examples, the method includes (f) applying a third force disposing the polymerase, in contact with the 3' end of the duplex, within or adjacent to the aperture on the first side of the nanopore. The method further may include, while applying the third force: inhibiting, using the nanopore, movement of the polymerase into, or further into, the aperture; and measuring the value of the electrical property of the polymerase. The method may include (g) identifying contact of the polymerase with the 3' end of the duplex using the value measured in operation (f). In some examples, the third force is less than the first force. In some examples, operation (f) is performed after operation (c) and before operation (d). In some examples, the first nucleotide is associated with a blocking moiety. In some examples, operation (g) further includes confirming presence of the blocking moiety associated with the first nucleotide using the value measured in operation (f).

In some examples, the polymerase includes a DNA polymerase. In some examples, the polymerase includes an RNA polymerase. In some examples, the polymerase includes a reverse transcriptase.

In some examples, the first nucleotide is associated with a blocking moiety, and operation (e) further includes confirming presence of the blocking moiety associated with the nucleotide using the value measured in operation (d). In some examples, the method includes removing the blocking moiety from the first nucleotide after operation (d). In some examples, the method includes, after removing the blocking moiety, (f) again applying the first force disposing the 3' end of the extended duplex within the aperture and the single-stranded portion of the polynucleotide within the aperture. The method may include, while again applying the first force: inhibiting, using the nanopore, translocation of the 3' end of the extended duplex to the second side of the nanopore; and measuring the value of the electrical property of the 3' end of the extended duplex and a single-stranded portion of the polynucleotide. The method may include (g) again identifying the first nucleotide using the value measured in operation (f). In some examples, the method includes removing the blocking moiety from the first nucleotide before operation (d).

In some examples, the extended duplex includes one or more nucleotide analogues. In some examples, the one or more nucleotide analogues enhance stability of the extended duplex relative to a natural nucleotide. In some examples, the one or more nucleotide analogues include one or more locked nucleic acids (LNA). In some examples, the one or more nucleotide analogues include one or more 2'-methoxy (2'-OMe) nucleotides. In some examples, the one or more nucleotide analogues include one or more 2'-fluorinated (2'-F) nucleotides. In some examples, the one or more nucleotide analogues alter the value of the electrical property relative to a natural nucleotide. In some examples, the first nucleotide includes one of the one or more nucleotide analogues. In some examples, the one or more nucleotide analogues include a 2' modification. In some examples, the one or more nucleotide analogues include a base modification.

In some examples, the first force is insufficiently strong to cause dissociation of the extended duplex.

In some examples, the first force includes a first voltage.

In some examples, operations (b) and (c) are performed in the absence of the first force.

In some examples, operation (c) is performed in the presence of a fourth force that opposes the first force.

In some examples, a first locking structure is coupled to the 3'-end of the polynucleotide on the first side of the nanopore. The first locking structure may inhibit translocation of the 3'-end of the polynucleotide to the second side of the nanopore through the aperture. In some examples, the first locking structure is removable.

In some examples, a second locking structure is coupled to the 5'-end of the polynucleotide on the second side of the nanopore. The second locking structure may inhibit translocation of the 5'-end of the polynucleotide to the first side of the nanopore through the aperture. In some examples, the second locking structure is removable.

In some examples, the method further includes, after operation (d): dissociating the extended duplex from the polynucleotide; and forming a new duplex with the polynucleotide on the first side of the nanopore, the new duplex including a new 3' end.

In some examples, operation (a) includes: contacting the nanopore with the polynucleotide hybridized to a substantially complementary polynucleotide; and applying a sixth force dehybridizing the substantially complementary polynucleotide from the polynucleotide.

In some examples, the nanopore includes a solid-state nanopore. In some examples, the nanopore includes a biological nanopore. In some examples, the biological nanopore includes MspA.

In some examples, the polynucleotide includes RNA. In some examples, the polynucleotide includes DNA.

In some examples, the extended duplex includes a primer hybridized to the polynucleotide.

Some examples herein provide a sequencing system. The sequencing system may include a nanopore including a first side, a second side, and an aperture extending through the first and second sides. The sequencing system may include a polynucleotide disposed through the aperture of the nanopore such that a 3' end of the polynucleotide is on the first side of the nanopore, and a 5' end of the polynucleotide is on the second side of the nanopore. The sequencing system may include a duplex with the polynucleotide disposed on the first side of the nanopore, the duplex including a 3' end at which a first nucleotide is disposed. The sequencing system may include circuitry configured to apply a first force disposing the 3' end of the duplex within the aperture. The circuitry also may be configured to measure a value of an electrical property of the 3' end of the duplex and a single-stranded portion of the polynucleotide while applying the first force. The circuitry also may be configured to identify the first nucleotide using the measured value. The nanopore may inhibit translocation of the 3' end of the duplex to the second side of the nanopore while the first force is applied.

In some examples, the value measured by the circuitry includes an electrical current, ionic current, electrical resistance, or electrical voltage drop across the nanopore. In some examples, the value measured by the circuitry includes noise of an electrical current, ionic current, electrical resistance, or electrical voltage drop across the nanopore. In some examples, the value measured by the circuitry includes a standard deviation of the noise.

In some examples, the value measured by the circuitry is at least based on M nucleotides of the single-stranded portion of the polynucleotide and D pairs of hybridized nucleotides of the duplex. M may be greater than or equal to two, and D may be greater than or equal to one. In some examples, M is greater than or equal to three. In some examples, D is greater than or equal to two. In some examples, at least one of the M nucleotides of the single-stranded portion includes a modified base, the circuitry being configured to identify the modified base using the value measured by the circuitry. In some examples, the modified base includes a methylated base.

In some examples, addition of another nucleotide to the 3' end of the duplex is inhibited while the first force is applied. In some examples, the nanopore inhibits the addition of another nucleotide.

In some examples, the nanopore is oriented so that the first side of the nanopore includes a majority of the aperture. In some examples, the nanopore is oriented so that the second side of the nanopore includes a majority of the aperture.

In some examples, the circuitry further is configured to apply a modified first force again disposing the 3' end of the duplex within the aperture. The circuitry further may be configured to measure a value of an electrical property of the 3' end of the duplex and a single-stranded portion of the polynucleotide while applying the modified first force. The circuitry further may be configured to identify the first nucleotide using the measured value. The nanopore may inhibit translocation of the 3' end of the duplex to the second side of the nanopore while the modified first force is applied.

In some examples, the system further includes a polymerase in contact with the 3' end of the duplex and configured to add the first nucleotide. In some examples, the polymerase is reversibly inhibited from adding a second nucleotide to the 3' end of the duplex. In some examples, the system further includes a blocking moiety reversibly inhibiting the polymerase from adding the second nucleotide to the 3' end of the duplex. In some examples, the first nucleotide is coupled to the blocking moiety. In some examples, the blocking moiety includes a 3'-blocking group. In some examples, the blocking moiety is reversibly associated with the duplex. In some examples, the circuitry further is configured to detect association of the blocking moiety with the duplex. In some examples, the circuitry further is configured to detect absence of the blocking moiety from the duplex. In some examples, the blocking moiety is removable to allow the polymerase to add the second nucleotide to the 3' end of the duplex.

In some examples, the first force removes the polymerase from contact with the 3' end of the duplex. In some examples, the circuitry further is configured to apply a second force to remove the polymerase from contact with the 3' end of the duplex, wherein the second force is greater than the first force. In some examples, the circuitry further is configured to: apply a third force disposing the polymerase, in contact with the 3' end of the duplex, within or adjacent to the aperture on the first side of the nanopore. The circuitry may be configured to measure the value of the electrical property of the polymerase while applying the third force. The circuitry may be configured to identify contact of the polymerase with the 3' end of the duplex using the value measured. The nanopore may inhibit movement of the polymerase into, or further into, the aperture. In some examples, the third force is less than the first force. In some examples, the circuitry is configured to apply the third force before applying the first force. In some examples, the first nucleotide is associated with a blocking moiety. In some examples, the circuitry is configured to confirm presence of the blocking moiety associated with the first nucleotide using the value measured.

In some examples, the polymerase includes a DNA polymerase. In some examples, the polymerase includes an RNA polymerase. In some examples, the polymerase includes a reverse transcriptase.

In some examples, the first nucleotide is associated with a blocking moiety, and the circuitry further is configured to confirm presence of the blocking moiety associated with the nucleotide using the value measured. In some examples, the blocking moiety is removed from the first nucleotide after applying the first force. In some examples, the circuitry is configured to, after the blocking moiety is removed, again apply the first force disposing the 3' end of the duplex within the aperture and the single-stranded portion of the polynucleotide within the aperture. The circuitry further may be configured to, while again applying the first force, measure the value of the electrical property of the 3' end of the duplex and a single-stranded portion of the polynucleotide. The circuitry further may be configured to again identify the first nucleotide using the value measured. The nanopore may inhibit translocation of the 3' end of the duplex to the second side of the nanopore. In some examples, the blocking moiety is removed from the first nucleotide before the first force is applied.

In some examples, the duplex includes one or more nucleotide analogues. In some examples, the one or more nucleotide analogues enhance stability of the duplex relative to a natural nucleotide. In some examples, the one or more nucleotide analogues include one or more locked nucleic acids (LNA). In some examples, the one or more nucleotide analogues include one or more 2'-methoxy (2'-OMe) nucleotides. In some examples, the one or more nucleotide analogues include one or more 2'-fluorinated (2'-F) nucleotides. In some examples, the one or more nucleotide analogues alter the value of the electrical property relative to a natural nucleotide. In some examples, the first nucleotide includes one of the one or more nucleotide analogues. In some examples, the one or more nucleotide analogues include a 2' modification. In some examples, the one or more nucleotide analogues include a base modification.

In some examples, the first force is insufficiently strong to cause dissociation of the duplex. In some examples, the first force includes a first voltage. In some examples, the polynucleotide is disposed through the aperture and the duplex is disposed on the first side of the nanopore in the absence of the first force. In some examples, the circuitry is configured to apply a fourth force that opposes the first force.

In some examples, a first locking structure is coupled to the 3'-end of the polynucleotide on the first side of the nanopore, the first locking structure inhibiting translocation of the 3'-end of the polynucleotide to the second side of the nanopore through the aperture. In some examples, the first locking structure is removable.

In some examples, a second locking structure is coupled to the 5'-end of the polynucleotide on the second side of the nanopore, the second locking structure inhibiting translocation of the 5'-end of the polynucleotide to the first side of the nanopore through the aperture. In some examples, the second locking structure is removable.

In some examples, the circuitry is configured to, after applying the first force, dissociate the duplex from the polynucleotide.

In some examples, the circuitry is configured to apply a sixth force dehybridizing a substantially complementary polynucleotide from the polynucleotide so as to dispose the polynucleotide through the aperture of the nanopore.

In some examples, the nanopore includes a solid-state nanopore. In some examples, the nanopore includes a biological nanopore. In some examples, the biological nanopore includes MspA.

In some examples, the polynucleotide includes RNA. In some examples, the polynucleotide includes DNA.

In some examples, the duplex includes a primer hybridized to the polynucleotide.

Some examples herein provide a method of sequencing an unknown polynucleotide. The method may include providing as input to a nucleotide identification module a plurality of measured values of an electrical property of a single-stranded portion of the unknown polynucleotide and a 3' end of a duplex with the unknown polynucleotide within an aperture of a nanopore. The method may include using the nucleotide identification module to compare the plurality of measured values to values within a data structure, wherein the data structure correlates different measured values with different combinations of nucleotides within a single-stranded portion of a known polynucleotide and a 3' end of a known duplex including the known polynucleotide within an aperture of a nanopore. The method may include using the nucleotide identification module to determine the sequence of nucleotides in the sequence of the unknown polynucleotide using the comparisons. The method may include receiving as output from the nucleotide identification module a representation of the determined sequence of nucleotides.

In some examples, the nucleotide identification module includes a trained machine-learning algorithm. In some examples, the nucleotide identification module includes a trained deep learning algorithm. In some examples, the data structure includes neurons of the trained machine-learning algorithm.

In some examples, the data structure includes a read map. In some examples, the read map includes a look-up table storing the different measured values and representations of the different combinations of nucleotides within the 3' end of the known duplex and the single-stranded portion of the known nucleotide.

In some examples, the method further includes, by the computer, using a measurement module to generate the plurality of measured values using the aperture of the nanopore.

In some examples, the method further includes, by the computer, using a nucleotide addition module, a measurement module, and a nucleotide identification module to generate the data structure using the aperture of the nanopore.

Some examples herein provide a system for sequencing an unknown polynucleotide. The system may include a processor; and at least one computer-readable medium. The computer-readable medium may store a plurality of measured values of an electrical property of a single-stranded portion of the unknown polynucleotide and a 3' end of a duplex including the unknown polynucleotide within an aperture of a nanopore. The computer-readable medium may store a data structure correlating different measured values with different combinations of nucleotides within a single-stranded portion of a known polynucleotide and a 3' end of a known duplex within an aperture of a nanopore. The computer-readable medium may store instructions for causing the processor to implement operations. The operations may include comparing the plurality of measured values to the values within the data structure. The operations may include determining the sequence of nucleotides in the sequence of the unknown polynucleotide using the comparisons. The operations may include outputting a representation of the determined sequence of nucleotides.

In some examples, the nucleotide identification module includes a trained machine-learning algorithm. In some examples, the nucleotide identification module includes a trained deep learning algorithm. In some examples, the data structure includes neurons of the trained machine-learning algorithm.

In some examples, the data structure includes a read map. In some examples, the read map includes a look-up table storing the different measured values and representations of the different combinations of nucleotides within the 3' end of the known duplex and the single-stranded portion of the known nucleotide.

In some examples, the instructions further are for causing the processor to generate the plurality of measured values using the aperture of the nanopore.

In some examples, the instructions further are for causing the processor to generate the data structure using the aperture of the nanopore.

Some examples herein provide a method of locking a polynucleotide to a nanopore that includes a first side, a second side, and an aperture extending through the first and second sides. The method may include (a) coupling a first locking group to a 3' end of the polynucleotide. The method may include (b) disposing the polynucleotide through the aperture of the nanopore such that the 3' end of the polynucleotide and the first locking group are on the first side of the nanopore, and a 5' end of the polynucleotide is on the second side of the nanopore. The method may include (c) coupling a second locking group to the 5' end of the polynucleotide on the second side of the nanopore.

In some examples, the first locking group includes locked nucleic acids (LNA) or peptide nucleic acids (PNA).

In some examples, the second locking group includes locked nucleic acids (LNA) or peptide nucleic acids (PNA).

In some examples, the polynucleotide is hybridized to a complementary polynucleotide prior to operation (a), the method further including dehybridizing the complementary polynucleotide between operations (b) and (c).

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1A:
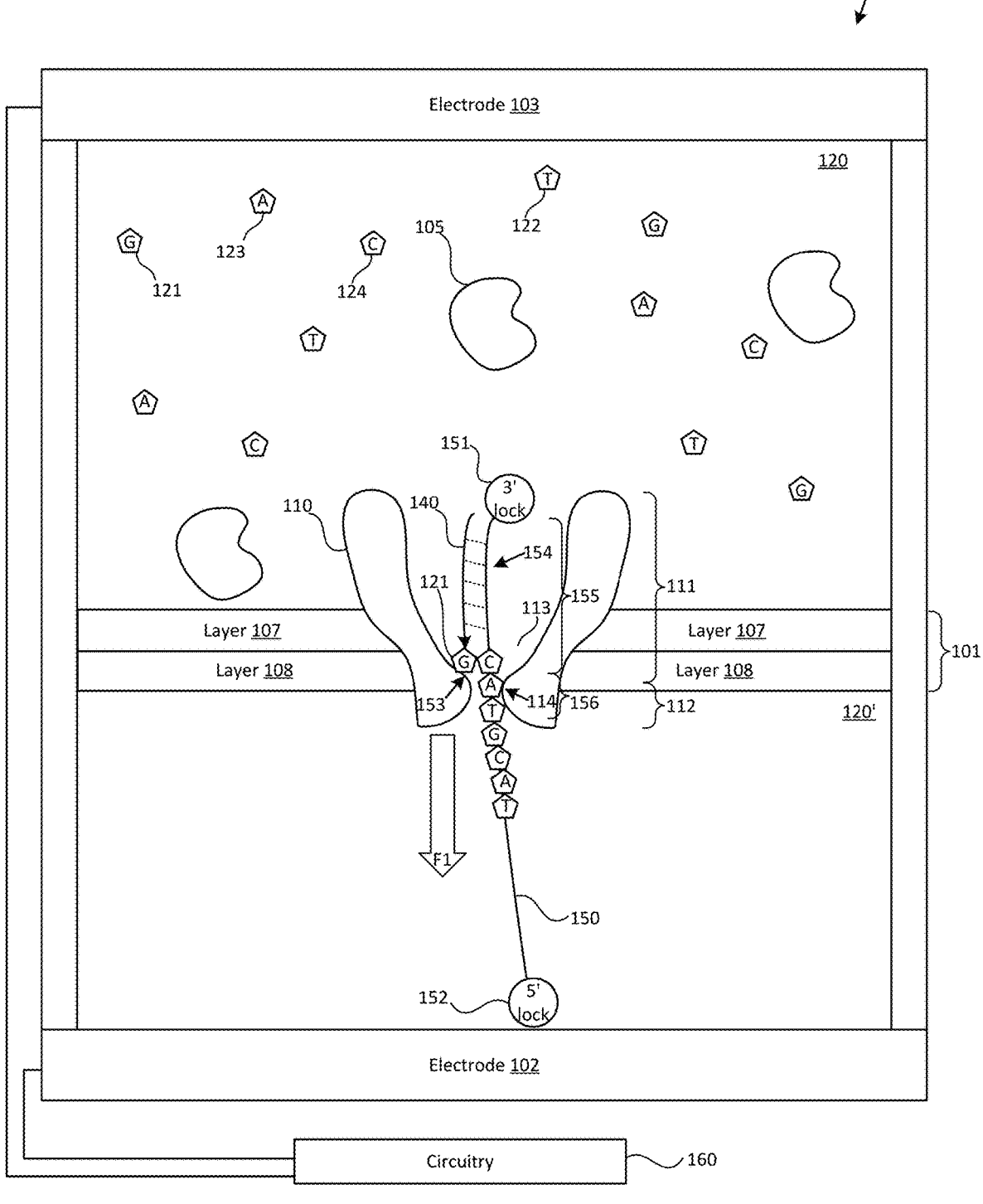
FIGS. 1A-1H schematically illustrate use of an example sequencing system, and example compositions and operations, for sequencing a polynucleotide using a nanopore.

Sequencing polynucleotides using nanopores is provided herein.

More specifically, in a manner such as described in greater detail below, a single-stranded target polynucleotide to be sequenced is disposed through the aperture of a nanopore. A duplex is formed with a portion of the target polynucleotide, on a first side of the nanopore. A force then is applied that lodges the duplex within the aperture of the nanopore, and an electrical measurement is made. The particular value of that measurement is based on the particular complementary bases that are located at the 3' end of the duplex, and the particular sequence of bases that are in a single-stranded portion of the target polynucleotide, within the aperture of the nanopore. Accordingly, the particular measured value provides information from which the sequence of the bases in the target polynucleotide may be determined. A force then is applied that dislodges the duplex from within the aperture of the nanopore so that the duplex may be extended by a nucleotide, and the measurement repeated. The repeated measurements provide further information from which the sequence of the bases in the target polynucleotide may be determined.

It will be appreciated that the present subject matter may be used to sequence polynucleotides—such as DNA or RNA—using relatively few reagents and without the need for optical components that otherwise may add cost, weight, and complexity. The present subject matter may be used to identify modified bases, such as methylated bases, without the need to chemically or enzymatically modify the modified bases. The present subject matter is be compatible with relatively long reads, e.g., of up to about 1,000 bases, or up to about 2,000 bases, or up to about 5,000 bases, or even up to 10,000 bases or more. The present subject matter overcomes the homopolymer problem traditionally associated with strand-based nanopore sequencing, for improved accuracy of sequencing areas that contain repeating nucleotides. The present subject matter provides for controllable translocation of polynucleotides through a nanopore, thus inhibiting or preventing translocation events that are too fast to go undetected and that may lead to deletion errors or other types of errors that detrimentally affect accuracy. These and other problems are solved by the present systems, compositions, and methods, as will be appreciated from the present disclosure.

First, some terms used herein will be briefly explained. Then, some example systems, compositions, and methods for sequencing polynucleotides using nanopores will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or system, the term "comprising" means that the compound, composition, or system includes at least the recited features or components, but may also include additional features or components.

As used herein, the singular forms "a", "an" and "the" include plural referents unless the content clearly dictates otherwise.

The terms "substantially," "approximately," and "about" used throughout this specification are used to describe and account for small fluctuations, such as due to variations in processing. For example, they may refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, the term "nucleotide" is intended to mean a molecule that includes a sugar and at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar, backbone, and/or phosphate moiety compared to naturally occurring nucleotides. Nucleotide analogues also may be referred to as "modified nucleic acids." Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. Nucleotides may include any suitable number of phosphates, e.g., three, four, five, six, or more than six phosphates. Nucleotide analogues also include locked nucleic acids (LNA), peptide nucleic acids (PNA), and 5-hydroxylbutynl-2'-deoxyuridine ("super T").

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof such as locked nucleic acids (LNA) and peptide nucleic acids (PNA). A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA, LNA, or PNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a "polymerase" is intended to mean an enzyme having an active site that assembles polynucleotides by polymerizing nucleotides into polynucleotides. A polymerase can bind a primer and a single stranded target polynucleotide, and can sequentially add nucleotides to the growing primer to form a "complementary copy" polynucleotide having a sequence that is complementary to that of the target polynucleotide. DNA polymerases may bind to the target polynucleotide and then move down the target polynucleotide sequentially adding nucleotides to the free hydroxyl group at the 3' end of a growing polynucleotide strand. DNA polymerases may synthesize complementary DNA molecules from DNA templates. RNA polymerases may synthesize RNA molecules from DNA templates (transcription). Other RNA polymerases, such as reverse transcriptases, may synthesize cDNA molecules from RNA templates. Still other RNA polymerases may synthesize RNA molecules from RNA templates, such as RdRP. Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase.

Example DNA polymerases include Bst DNA polymerase, 9° Nm DNA polymerase, Phi29 DNA polymerase, DNA polymerase I (E. coli), DNA polymerase I (Large), (Klenow) fragment, Klenow fragment (3'-5' exo-), T4 DNA polymerase, T7 DNA polymerase, Deep VentR™ (exo-) DNA polymerase, Deep VentR™ DNA polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo-) DNA Polymerase, RepliPHI™ Phi29 DNA Polymerase, rBst DNA Polymerase, rBst DNA Polymerase (Large), Fragment (IsoTherm™ DNA Polymerase), MasterAmp™ AmpliTherm™, DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, ThermoPhi DNA polymerase, and IsopoI™ SD+ polymerase. In specific, nonlimiting examples, the polymerase is selected from a group consisting of Bst, Bsu, and Phi29. Some polymerases have an activity that degrades the strand behind them (3' exonuclease activity). Some useful polymerases have been modified, either by mutation or otherwise, to reduce or eliminate 3' and/or 5' exonuclease activity.

Example RNA polymerases include RdRps (RNA dependent, RNA polymerases) that catalyze the synthesis of the RNA strand complementary to a given RNA template. Example RdRps include polioviral 3Dpol, vesicular stomatitis virus L, and hepatitis C virus NSSB protein. Example RNA Reverse Transcriptases. A non-limiting example list to include are reverse transcriptases derived from Avian Myelomatosis Virus (AMV), Murine Moloney Leukemia Virus (MMLV) and/or the Human Immunodeficiency Virus (HIV), telomerase reverse transcriptases such as (hTERT), SuperScript™ III, SuperScript™ IV Reverse Transcriptase, ProtoScript® II Reverse Transcriptase.

As used herein, the term "primer" is defined as a poly-nucleotide to which nucleotides may be added via a free 3' OH group. A primer may include a 3' block inhibiting polymerization until the block is removed. A primer may include a modification at the 5' terminus to allow a coupling reaction or to couple the primer to another moiety. A primer may include one or more moieties, such as 8-oxo-G, which may be cleaved under suitable conditions, such as UV light, chemistry, enzyme, or the like. The primer length may be any suitable number of bases long and may include any suitable combination of natural and non-natural nucleotides. A target polynucleotide may include an "amplification adapter" or, more simply, an "adapter," that hybridizes to (has a sequence that is complementary to) a primer, and may be amplified so as to generate a complementary copy polynucleotide by adding nucleotides to the free 3' OH group of the primer.

As used herein, the term "plurality" is intended to mean a population of two or more different members. Pluralities may range in size from small, medium, large, to very large. The size of small plurality may range, for example, from a few members to tens of members. Medium sized pluralities may range, for example, from tens of members to about 100 members or hundreds of members. Large pluralities may range, for example, from about hundreds of members to about 1000 members, to thousands of members and up to tens of thousands of members. Very large pluralities may range, for example, from tens of thousands of members to about hundreds of thousands, a million, millions, tens of millions and up to or greater than hundreds of millions of members. Therefore, a plurality may range in size from two to well over one hundred million members as well as all sizes, as measured by the number of members, in between and greater than the above example ranges. Example poly-nucleotide pluralities include, for example, populations of about $1\times10^5$ or more, $5\times10^5$ or more, or $1\times10^6$ or more different polynucleotides. Accordingly, the definition of the term is intended to include all integer values greater than two. An upper limit of a plurality may be set, for example, by the theoretical diversity of polynucleotide sequences in a sample.

As used herein, the term "double-stranded," when used in reference to a polynucleotide, is intended to mean that all or substantially all of the nucleotides in the polynucleotide are hydrogen bonded to respective nucleotides in a complementary polynucleotide. A double-stranded polynucleotide also may be referred to as a "duplex."

As used herein, the term "single-stranded," when used in reference to a polynucleotide, means that essentially none of the nucleotides in the polynucleotide are hydrogen bonded to a respective nucleotide in a complementary polynucle-otide.

As used herein, the term "target polynucleotide" is intended to mean a polynucleotide that is the object of an analysis or action, and may also be referred to using terms such as "library polynucleotide," "template polynucleotide," or "library template." The analysis or action includes sub-jecting the polynucleotide to amplification, sequencing and/or other procedure. A target polynucleotide may include nucleotide sequences additional to a target sequence to be analyzed. For example, a target polynucleotide may include one or more adapters, including an amplification adapter that functions as a primer binding site, that flank(s) a target polynucleotide sequence that is to be analyzed. In particular examples, target polynucleotides may have different sequences than one another but may have first and second adapters that are the same as one another. The two adapters that may flank a particular target polynucleotide sequence may have the same sequence as one another, or comple-mentary sequences to one another, or the two adapters may have different sequences. Thus, species in a plurality of target polynucleotides may include regions of known sequence that flank regions of unknown sequence that are to be evaluated by, for example, sequencing (e.g., SBS). In some examples, target polynucleotides carry an amplifica-tion adapter at a single end, and such adapter may be located at either the 3' end or the 5' end the target polynucleotide. Target polynucleotides may be used without any adapter, in which case a primer binding sequence may come directly from a sequence found in the target polynucleotide.

The terms "polynucleotide" and "oligonucleotide" are used interchangeably herein. The different terms are not intended to denote any particular difference in size, sequence, or other property unless specifically indicated otherwise. For clarity of description, the terms may be used to distinguish one species of polynucleotide from another when describing a particular method or composition that includes several polynucleotide species.

As used herein, the term "substrate" refers to a material used as a support for compositions described herein. Example substrate materials may include glass, silica, plas-tic, quartz, metal, metal oxide, organo-silicate (e.g., poly-hedral organic silsesquioxanes (POSS)), polyacrylates, tan-talum oxide, complementary metal oxide semiconductor (CMOS), or combinations thereof. An example of POSS can be that described in Kehagias et al., Microelectronic Engi-neering 86 (2009), pp. 776-778, which is incorporated by reference in its entirety. In some examples, substrates used in the present application include silica-based substrates, such as glass, fused silica, or other silica-containing mate-rial. In some examples, silica-based substrates can include silicon, silicon dioxide, silicon nitride, or silicone hydride. In some examples, substrates used in the present application include plastic materials or components such as polyethyl-ene, polystyrene, poly(vinyl chloride), polypropylene, nylons, polyesters, polycarbonates, and poly(methyl meth-acrylate). Example plastics materials include poly(methyl methacrylate), polystyrene, and cyclic olefin polymer sub-strates. In some examples, the substrate is or includes a silica-based material or plastic material or a combination thereof. In particular examples, the substrate has at least one surface including glass or a silicon-based polymer. In some examples, the substrates can include a metal. In some such examples, the metal is gold. In some examples, the substrate has at least one surface including a metal oxide. In one example, the surface includes a tantalum oxide or tin oxide.

Acrylamides, enones, or acrylates may also be utilized as a substrate material or component. Other substrate materials can include, but are not limited to gallium arsenide, indium phosphide, aluminum, ceramics, polyimide, quartz, resins, polymers and copolymers. In some examples, the substrate and/or the substrate surface can be, or include, quartz. In some other examples, the substrate and/or the substrate surface can be, or include, semiconductor, such as GaAs or ITO. The foregoing lists are intended to be illustrative of, but not limiting to the present application. Substrates can include a single material or a plurality of different materials. Substrates can be composites or laminates. In some examples, the substrate includes an organo-silicate material.

Substrates can be flat, round, spherical, rod-shaped, or any other suitable shape. Substrates may be rigid or flexible. In some examples, a substrate is a bead or a flow cell.

Substrates can be non-patterned, textured, or patterned on one or more surfaces of the substrate. In some examples, the substrate is patterned. Such patterns may include posts, pads, wells, ridges, channels, or other three-dimensional concave or convex structures. Patterns may be regular or irregular across the surface of the substrate. Patterns can be formed, for example, by nanoimprint lithography or by use of metal pads that form features on non-metallic surfaces, for example.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that can be used in methods and compositions set forth herein include, but are not limited to, those commercially available from Illumina, Inc. (San Diego, CA).

As used herein, the term "electrode" is intended to mean a solid structure that conducts electricity. Electrodes may include any suitable electrically conductive material, such as gold, palladium, or platinum, or combinations thereof. In some examples, an electrode may be disposed on a substrate. In some examples, an electrode may define a substrate.

As used herein, the term "nanopore" is intended to mean a structure that includes an aperture that permits molecules to cross therethrough from a first side of the nanopore to a second side of the nanopore, in which a portion of the aperture of a nanopore has a width of 100 nm or less, e.g., 10 nm or less, or 2 nm or less. The aperture extends through the first and second sides of the nanopore. Molecules that can cross through an aperture of a nanopore can include, for example, ions or water-soluble molecules such as amino acids or nucleotides. The nanopore can be disposed within a barrier, or can be provided through a substrate. Optionally, a portion of the aperture can be narrower than one or both of the first and second sides of the nanopore, in which case that portion of the aperture can be referred to as a "constriction." Alternatively or additionally, the aperture of a nanopore, or the constriction of a nanopore (if present), or both, can be greater than 0.1 nm, 0.5 nm, 1 nm, 10 nm or more. A nanopore can include multiple constrictions, e.g., at least two, or three, or four, or five, or more than five constrictions. nanopores include biological nanopores, solid-state nanopores, or biological and solid-state hybrid nanopores.

Biological nanopores include, for example, polypeptide nanopores and polynucleotide nanopores. A "polypeptide nanopore" is intended to mean a nanopore that is made from one or more polypeptides. The one or more polypeptides can include a monomer, a homopolymer or a heteropolymer. Structures of polypeptide nanopores include, for example, an α-helix bundle nanopore and a β-barrel nanopore as well as all others well known in the art. Example polypeptide nanopores include α-hemolysin, *Mycobacterium smegmatis* porin A, gramicidin A, maltoporin, OmpF, OmpC, PhoE, Tsx, F-pilus, SP1, mitochondrial porin (VDAC), Tom40, outer membrane phospholipase A, CsgG, aerolysin, and Neisseria autotransporter lipoprotein (NalP). *Mycobacterium smegmatis* porin A (MspA) is a membrane porin produced by Mycobacteria, allowing hydrophilic molecules to enter the bacterium. MspA forms a tightly interconnected octamer and transmembrane beta-barrel that resembles a goblet and includes a central constriction. For further details regarding α-hemolysin, see U.S. Pat. No. 6,015,714, the entire contents of which are incorporated by reference herein. For further details regarding SP1, see Wang et al., Chem. Commun., 49:1741-1743 (2013), the entire contents of which are incorporated by reference herein. For further details regarding MspA, see Butler et al., "Single-molecule DNA detection with an engineered MspA protein nanopore," Proc. Natl. Acad. Sci. 105: 20647-20652 (2008) and Derrington et al., "Nanopore DNA sequencing with MspA," Proc. Natl. Acad. Sci. USA, 107:16060-16065 (2010), the entire contents of both of which are incorporated by reference herein. Other nanopores include, for example, the MspA homolog from Norcadia farcinica, and lysenin. For further details regarding lysenin, see PCT Publication No. WO 2013/153359, the entire contents of which are incorporated by reference herein. For further details regarding aerolysin, see Cao et al., "Single-molecule sensing of peptides and nucleic acids by engineered aerolysin nanopores," Nature Communications 10: Article number: 4918 (2019), the entire contents of which are incorporated by reference herein.

A "polynucleotide nanopore" is intended to mean a nanopore that is made from one or more nucleic acid polymers. A polynucleotide nanopore can include, for example, a polynucleotide origami.

A "solid-state nanopore" is intended to mean a nanopore that is made from one or more materials that are not of biological origin. A solid-state nanopore can be made of inorganic or organic materials. Solid-state nanopores include, for example, silicon nitride (SiN), silicon dioxide ($SiO_2$), silicon carbide (SiC), hafnium oxide ($HfO_2$), molybdenum disulfide ($MoS_2$), hexagonal boron nitride (h-BN), or graphene. A solid-state nanopore may comprise an aperture formed within a solid-state membrane, e.g., a membrane including any such material(s).

A "biological and solid-state hybrid nanopore" is intended to mean a hybrid nanopore that is made from materials of both biological and non-biological origins. Materials of biological origin are defined above and include, for example, polypeptides and polynucleotides. A biological and solid-state hybrid nanopore includes, for example, a polypeptide-solid-state hybrid nanopore and a polynucleotide-solid-state nanopore.

As used herein, a "barrier" is intended to mean a structure that normally inhibits passage of molecules from one side of the barrier to the other side of the barrier. The molecules for which passage is inhibited can include, for example, ions or water soluble molecules such as nucleotides and amino acids. However, if a nanopore is disposed within a barrier, then the aperture of the nanopore may permit passage of molecules from one side of the barrier to the other side of the barrier. As one specific example, if a nanopore is disposed within a barrier, the aperture of the nanopore may permit passage of molecules from one side of the barrier to the other side of the barrier. Barriers include membranes of biological origin, such as lipid bilayers, and non-biological barriers such as solid-state membranes or substrates.

As used herein, "of biological origin" refers to material derived from or isolated from a biological environment such as an organism or cell, or a synthetically manufactured version of a biologically available structure.

As used herein, "solid-state" refers to material that is not of biological origin.

As used herein, a "blocking moiety" is intended to mean a moiety that inhibits a polymerase from adding another nucleotide to an end of a duplex until that moiety is removed. A "blocking group" is a nonlimiting example of a blocking moiety, and is intended to mean a chemical group. In some examples, a nucleotide may be coupled to a blocking group. Removal of a blocking group from a nucleotide may be referred to as "deblocking" that nucleotide. In examples in which the 3' position of a nucleotide is coupled to a blocking group, that blocking group may be referred to as a "3'-blocking group." A 3'-blocking group may inhibit a polymerase from coupling another nucleotide to that nucleotide until that moiety is removed and replaced with a hydroxyl (OH) group.

As used herein, the term "methylated base" refers to a base that includes a methyl group (—CH$_3$ or -Me) or a derivatized methyl group. For example, "methylcytosine" or "mC" refers to cytosine in DNA (namely, 2'-deoxycytosine) that includes a methyl group, or is a derivative of methylcytosine. As another example, "methyladenine" or "mA" refers to adenine in DNA that includes a methyl group, or is a derivative of methyadenine. A nonlimiting example of a derivatized methyl group is an oxidized methyl group. A nonlimiting example of an oxidized methyl group is hydroxymethyl (—CH$_2$OH). An mC derivative having a hydroxymethyl group may be referred to as hydroxymethylcytosine or hmC. Another nonlimiting example of an oxidized methyl group is formyl group (—CHO). An mC derivative having a formyl group may be referred to as formylcytosine or fC. Another nonlimiting example of an oxidized methyl group is carboxyl (—COOH). An mC derivative including a carboxyl group may be referred to as carboxycytosine or caC. The methyl group of methylcytosine may be located at the 5 position of the cytosine, in which case the mC may be referred to as 5mC. The oxidized methyl group may be located at the 5 position of the cytosine, in which case the hmC may be referred to as 5hmC, the fC may be referred to as 5fC, or the caC may be referred to as 5caC. The methyl group of methyladenine may be located at the 6 position of the adenine, in which case the mA may be referred to as 6 mA.

Sequencing Polynucleotides Using Nanopores

Some example operations, compositions, and systems for sequencing polynucleotides using nanopores now will be described with reference to FIGS. 1A-1H, 2A-2E, 3, 4A-4C, 5A-5B, 6, 7, 8A-8E, 9, and 10.

Referring now to FIG. 1A, sequencing system 100 may include nanopore 110, polynucleotide 150 that it is desired to sequence (e.g., that may be unknown), polynucleotide 140 that is hybridized to first portion 155 of polynucleotide 150 to form duplex 154, and circuitry 160.

Figure 7:
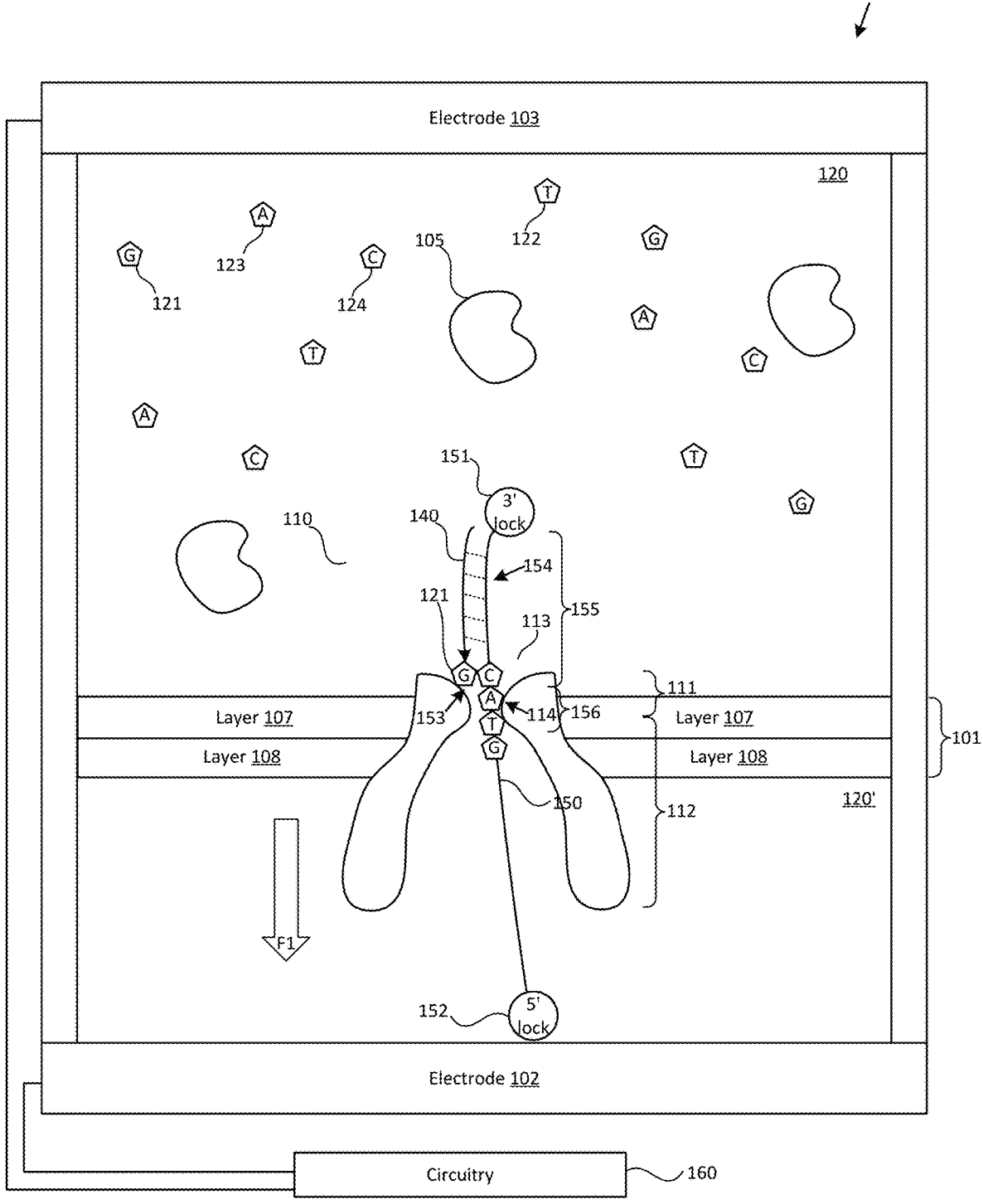
FIG. 7 schematically illustrates an alternative configuration of the sequencing system of FIGS. 1A-1H.

Nanopore 110 may be disposed within barrier 101 and may include first side 111, second side 112, and aperture 113 extending through the first and second sides. Optionally, in some examples, nanopore 110 may include constriction 114 within aperture 113. Aperture 113 of nanopore 110 may provide a pathway for fluid 120 and/or fluid 120' to flow through barrier 101. Nanopore 110 may include a solid-state nanopore, a biological nanopore (e.g., MspA such as illustrated in FIG. 1A), or a biological and solid-state hybrid nanopore. In the nonlimiting example illustrated in FIG. 1A, nanopore 110 may be oriented so that first side 111 of the nanopore includes the majority of aperture 113, such that 3' end 153 of duplex 154 may fit relatively deeply within aperture 113 so as to be relatively inaccessible to fluid 120 and thus may not be acted upon by any polymerase in the fluid. Alternatively, as illustrated in FIG. 7, nanopore 110 may be oriented so that second side 112 of the nanopore includes the majority of aperture 113, such that 3' end of duplex 154 may fit relatively shallowly within aperture 113, and still may be relatively inaccessible to fluid 120 and thus may not be acted upon any polymerase in the fluid. While many of the examples herein may be described with reference to asymmetrical nanopores in "forward" orientations such as illustrated in FIG. 1A, it should be understood that in all such examples, nanopore 110 may have either the orientation illustrated in FIG. 1A or the "reverse" orientation illustrated in FIG. 7. Furthermore, nanopores may be symmetrical, and as such may not necessarily be considered to have either a "forward" or a "reverse" orientation.

Barrier 101 may have any suitable structure that normally inhibits passage of molecules from one side of the barrier to the other side of the barrier, e.g., that normally inhibits contact between fluid 120 and fluid 120'. For example, as illustrated in FIG. 1A, barrier 101 may include first layer 107 and second layer 108, one or both of which inhibit the flow of molecules across that layer. Illustratively, barrier 101 may include a lipid bilayer including lipid layers 107 and 108. However, it will be appreciated that barrier 101 may include any suitable structure(s), any suitable material(s), and any suitable number of layers. For example, barrier 101 may include a solid-state barrier, which may include a single layer or multiple layers. Nonlimiting examples of materials that may be used in barriers are provided elsewhere herein. Nonlimiting examples and properties of barriers and nanopores are described elsewhere herein, as well as in U.S. Pat. No. 9,708,655, the entire contents of which are incorporated by reference herein.

Polynucleotide 150 may include, for example, DNA or RNA. Polynucleotide 150 may be disposed through aperture 113 of nanopore 110 such that a first portion 155 of the polynucleotide 150 is located, optionally entirely, on first side 111 of the nanopore. The 3' end of polynucleotide 150 may be located on the first side 111 of nanopore 110, and the 5' end of polynucleotide 150 may be located on the second side 112 of nanopore 110. Optionally, the 3' end of polynucleotide 150 may be coupled to, or may include, a first steric lock 151. First steric lock 151 is sufficiently large as not to be able to pass through nanopore 110 or feature thereof (e.g., through constriction 114), thus retaining that end on the first side of the nanopore. As an additional or alternative option, the 5' end of polynucleotide 150 may be located on second side 112 of nanopore 110 and may be coupled to, or may include a second steric lock 152. Second steric lock 152 is sufficiently large as not to be able to pass through constriction 114 (such as an oligonucleotide hybridized to polynucleotide 150), thus retaining the second end of polynucleotide 150 on the second side of the nanopore. As such, regardless of the polarity of a bias voltage that circuitry 160 may apply to electrodes 102 and 103 during the operating mode illustrated in FIG. 1A, polynucleotide 150 may remain associated with nanopore 110 during this operating mode.

Polynucleotide 140 may include, for example, DNA or RNA. Polynucleotide 140 may include, for example, a primer hybridized to the first portion of polynucleotide 150 to form duplex 154. The duplex 154 between polynucleotide 140 and the first portion of polynucleotide 150 may be located, optionally entirely, on first side 111 of the nanopore, and may include 3' end 153. In this nonlimiting example, 3' end 153 includes the base pair GC, and it is desired to identify the C as being at this location of the sequence of polynucleotide 150, in addition to the sequence of other nucleotides in polynucleotide 150. The G nucleotide 121 may have been, but need not necessarily have been, incorporated into polynucleotide 140 based on the sequence of polynucleotide 150 using a polymerase, in a manner such as described in greater detail below with reference to FIG. 1B. Single-stranded second portion 156 of polynucleotide 150 (e.g., bases A and T) may be within aperture 113 but not hybridized to polynucleotide 140. Bases of polynucleotides 140, 150 that are not specifically illustrated or labeled should be understood to be present, but omitted for simplicity of illustration.

The hybridization between polynucleotide 140 and the first portion of polynucleotide 150 may be sufficiently strong that, regardless of any bias voltage that circuitry 160 may apply to electrodes 102 and 103 during certain operating modes, the duplex may remain substantially intact. However, in a manner such as will be described further below with reference to FIGS. 4A-4C, circuitry 160 may be configured to have another operating mode in which the circuitry applies a sufficiently strong force to dissociate polynucleotide 140 from polynucleotide 150 and making polynucleotide 150 available to be re-sequenced using another polynucleotide 140, optionally using the same set of measurement conditions or a different set of measurement conditions. Additionally, or alternatively, in a manner such as will be described further below with reference to FIGS. 5A-5B, circuitry 160 may be configured to have another operating mode in which the circuitry applies a sufficiently strong force to dissociate polynucleotide 150 from nanopore 110 and making nanopore 110 available to sequence a different polynucleotide.

In the operating mode illustrated in FIG. 1A, circuitry 160 may apply a first force (F1) disposing the 3' end 153 of duplex 154 within aperture 113. Nanopore 110 inhibits translocation of 3' end 153 of duplex 154 to the second side of the nanopore while the first force is applied. For example, at the particular moment illustrated in FIG. 1A, circuitry 160 applies a first force F1 (such as a first voltage across nanopore 110) that moves duplex 154 towards the second side 112 of nanopore 110, while constriction 114 or other feature of nanopore 110 inhibits the passage of 3' end 153 of the duplex to the second side of the nanopore. In the example illustrated in FIG. 1A, duplex 154 may be wider than constriction 114, and thus sterically hindered from passing through constriction 114. However, it should be appreciated that any suitable portion(s) of nanopore 110 may be used to inhibit the 3' end 153 of duplex 154 from passing to the second side of the nanopore.

As should be understood from the presence of duplex 154 during the operating mode illustrated in FIG. 1A, first force F1 is selected so as to be insufficient to cause dissociation of duplex 154, e.g., dehybridization of polynucleotide 140 from polynucleotide 150. Similarly, in other figures herein in which a duplex is illustrated, it should be understood that the force which circuitry 160 applies is insufficient to cause dissociation of that duplex in the described operating mode; however, other operating modes may be used to intentionally dissociate the duplex. In some examples, duplex 154 may include one or more nucleotide analogues. Such nucleotide analogue(s) may, for example, enhance stability of duplex 154 relative to a natural nucleotide. For example, the nucleotide analogue(s) may include one or more locked nucleic acids (LNA) or may include one or more 2'-methoxy (2'-OMe) nucleotides, or may include one or more 2'-fluorinated (2'-F) nucleotides, or may include one or more peptide nucleic acids (PNA). Such analogue(s) may be included, for example, in polynucleotide 140. Illustratively, such analogue(s) may be added to the primer at the time it is synthesized, or potentially triphosphate nucleotides with these modifications could be incorporated into strand 140 by the polymerase. Such analogue(s) may increase the Tm (melting temperature) of duplex 154. For example, addition of LNA monomers may help to increase the Tm of duplex 154 and may be used to fine-tune the Tm of duplex 154. Or, for example, 2'-OMe may increase the Tm of RNA:RNA duplexes and results in only small changes in RNA:DNA stability. Or, for example, 2' Fluoro bases may have a fluorine modified ribose which increases binding affinity (Tm) and also may confer some relative nuclease resistance when compared to native RNA.

Circuitry 160 may be configured to measure a value of an electrical property of the 3' end 153 of duplex 154 and a single-stranded portion of polynucleotide 150 (e.g., second portion 156) while applying the first force F1, and to identify at least one nucleotide in the polynucleotide 150 using the value measured. For example, circuitry 160 may be in operable communication with first and second electrodes 102, 103 and configured to detect the ionic current passing through the nanopore 110, or an electrical current, electrical resistance, or electrical voltage drop across nanopore 110 during application of the first force F1. For example, fluid 120 may include one or more salts such as KCl, NaCl, potassium ferrocyanide, potassium ferricyanide, or potassium glutamate. In the nonlimiting example illustrated in FIG. 1A, the particular base pair at 3' end 153 of duplex 154 (e.g., GC), and the sequence of one or more bases in single-stranded portion 156 (e.g., A,T), may alter the rate at which the salt in fluid 120 moves through aperture 113 and into fluid 120', and thus may alter the electrical current, ionic current, electrical resistance, or electrical voltage drop across nanopore 110 in such a manner as to be detected by circuitry 160. Additionally, or alternatively, the particular base pair(s) at the 3' end 153 of duplex 154 (e.g., GC), and the sequence of one or more bases in single-stranded portion 156 (e.g., A,T), may alter noise in the measurement, e.g., may alter fluctuations in the rate at which salt in fluid 120 moves through aperture 113 and into fluid 120', and thus may alter the standard deviation of electrical current, the standard deviation of ionic current, the standard deviation of electrical resistance, or the standard deviation of electrical voltage drop across nanopore 110 in such a manner as to be detected by circuitry 160. In some examples, duplex 154 may include one or more nucleotide analogue(s) that alter the value of the electrical property of the nanopore relative to a natural nucleotide. For example, polynucleotide 140 may include nucleotide analogue(s) such as a 2' modification, or a base modification. Such analogue(s) thus may be identified using circuitry 160.

The value that circuitry 160 measures during the operation illustrated in FIG. 1A may be based on any suitable number of nucleotides in first portion 155 (which portion is hybridized to polynucleotide 140) and in second portion 156 (which portion is single-stranded and not hybridized to polynucleotide 140). For example, the measured value may be at least based on M nucleotides of the single-stranded portion and D pairs of hybridized nucleotides of the duplex, wherein M is greater than or equal to one, and wherein D is greater than or equal to one. M and D may have any suitable values. For example, M may be greater than or equal to two, or M may be greater than or equal to three, or M may be greater than or equal to four. Illustratively, M may be about one. Or, illustratively, M may be about two. Or, illustratively, M may be about three. Or, illustratively, M may be about four. Or, illustratively, M may be about five. Additionally, or alternatively, D may be greater than or equal to two, or D may be greater than or equal to three, or D may be greater than or equal to four. Illustratively, D may be about one. Or, illustratively, D may be about two. Or, illustratively, D may be about three. Or, illustratively, D may be about four. Or, illustratively, D may be about five.

The value measured by circuitry 160 may include an electrical current, ionic current, electrical resistance, or electrical voltage drop that is based on the M nucleotides and D pairs of hybridized nucleotides. The value measured by circuitry 160 also, or alternatively, may include noise of an electrical current, ionic current, electrical resistance, or electrical voltage drop across the nanopore, e.g., may include the standard deviation of the noise, which noise is based on the M nucleotides and D pairs of hybridized nucleotides. For example, referring now to FIG. 1F, the numbers are used to represent bases which may affect the measured value under a given force (here, first force F1). For an MspA nanopore such as illustrated, it may be expected that bases 4, 5, 6, and 4' primarily may affect the measured value, although bases adjacent to these may also influence the measured value in a manner such as described elsewhere herein. For example, bases 3 and 3' may affect the measured value. Additionally, or alternatively, base 7 may affect the measured value. Additionally, or alternatively, base 8 may affect the measured value. In one nonlimiting example, bases 3, 3', 4, 4', 5, 6, 7, and 8 affect the measured value. In another nonlimiting example, bases 3, 3', 4, 4', 5, 6, and 7 affect the measured value. In another nonlimiting example, bases 4, 4', 5, 6, 7, and 8 affect the measured value. In another nonlimiting example, bases 3, 3', 4, 4', 5, and 6 affect the measured value. In another nonlimiting example, bases 4, 4', 5, 6, and 7 affect the measured value. In another nonlimiting example, bases 4, 4', 5, and 6 affect the measured value.

Figure 1B:
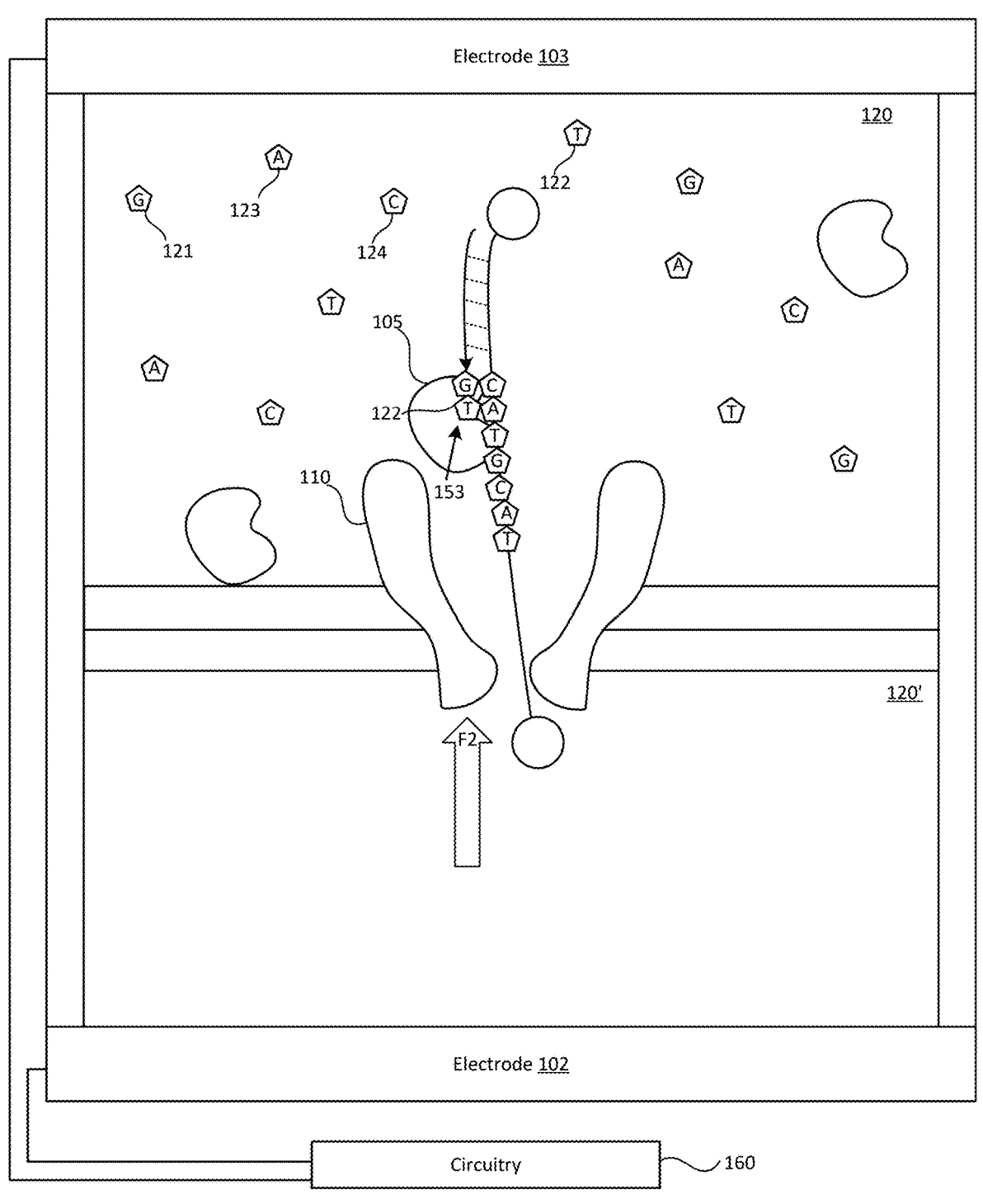
Figure 1C:
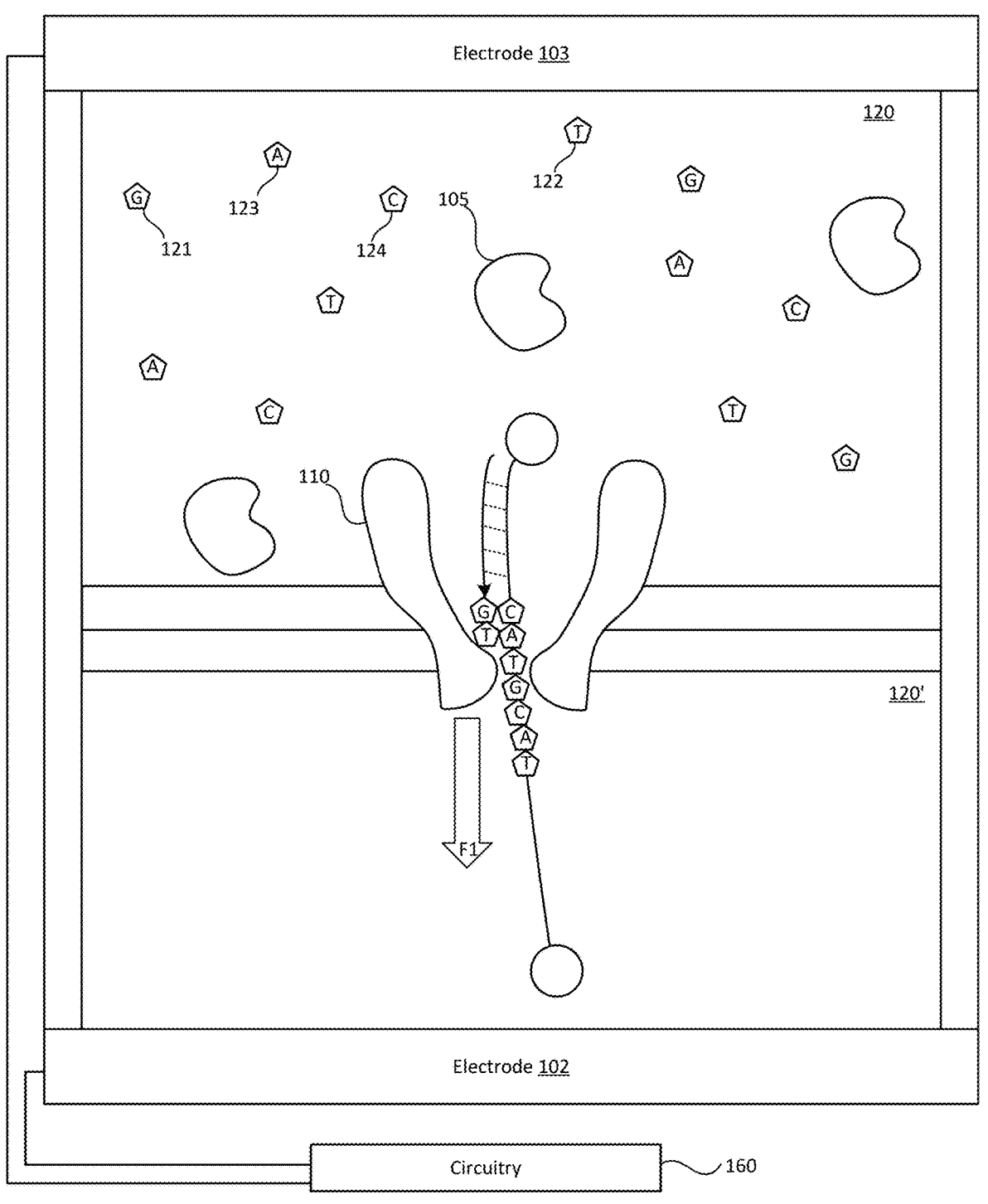
Figure 1D:
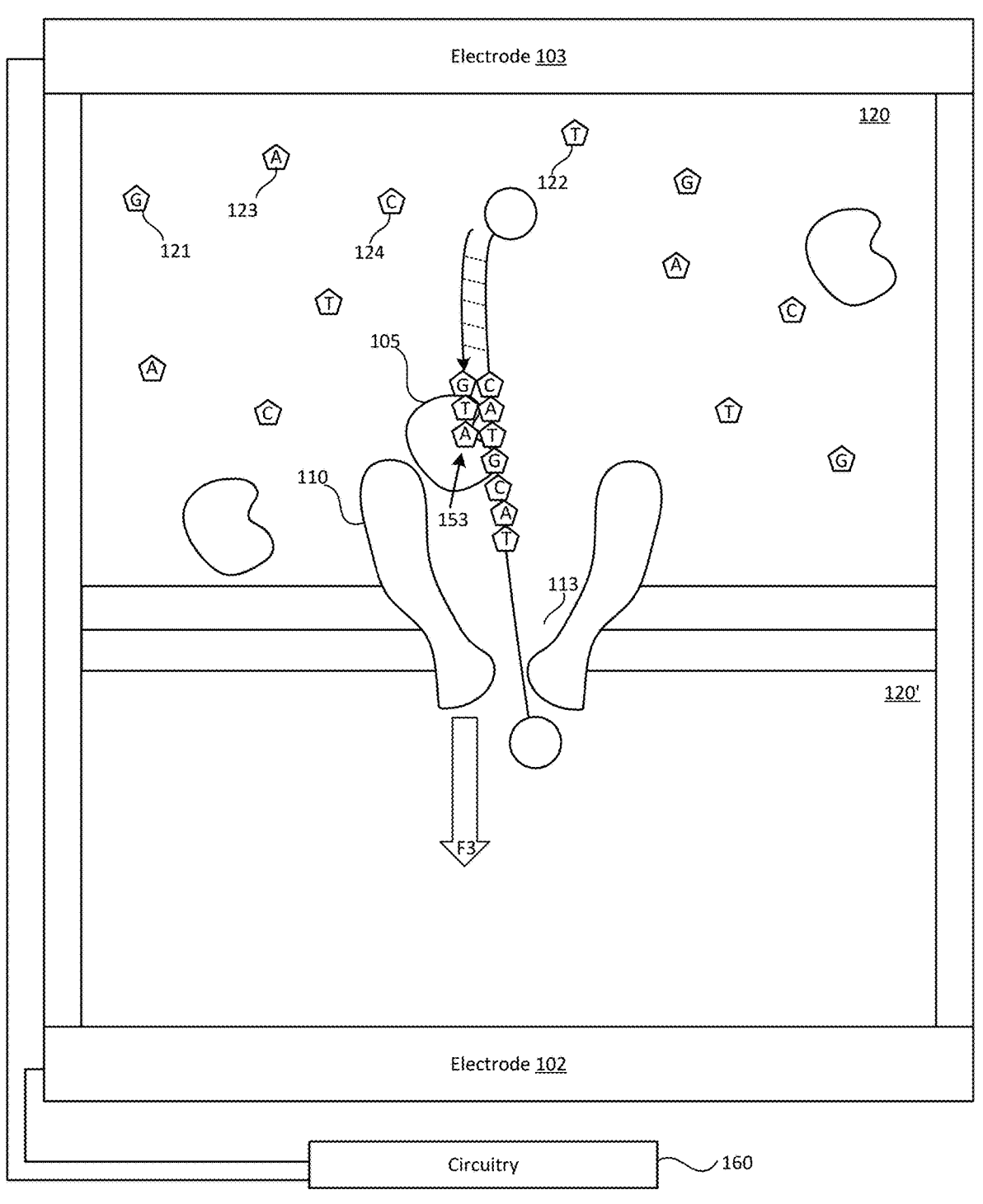
Figure 1E:
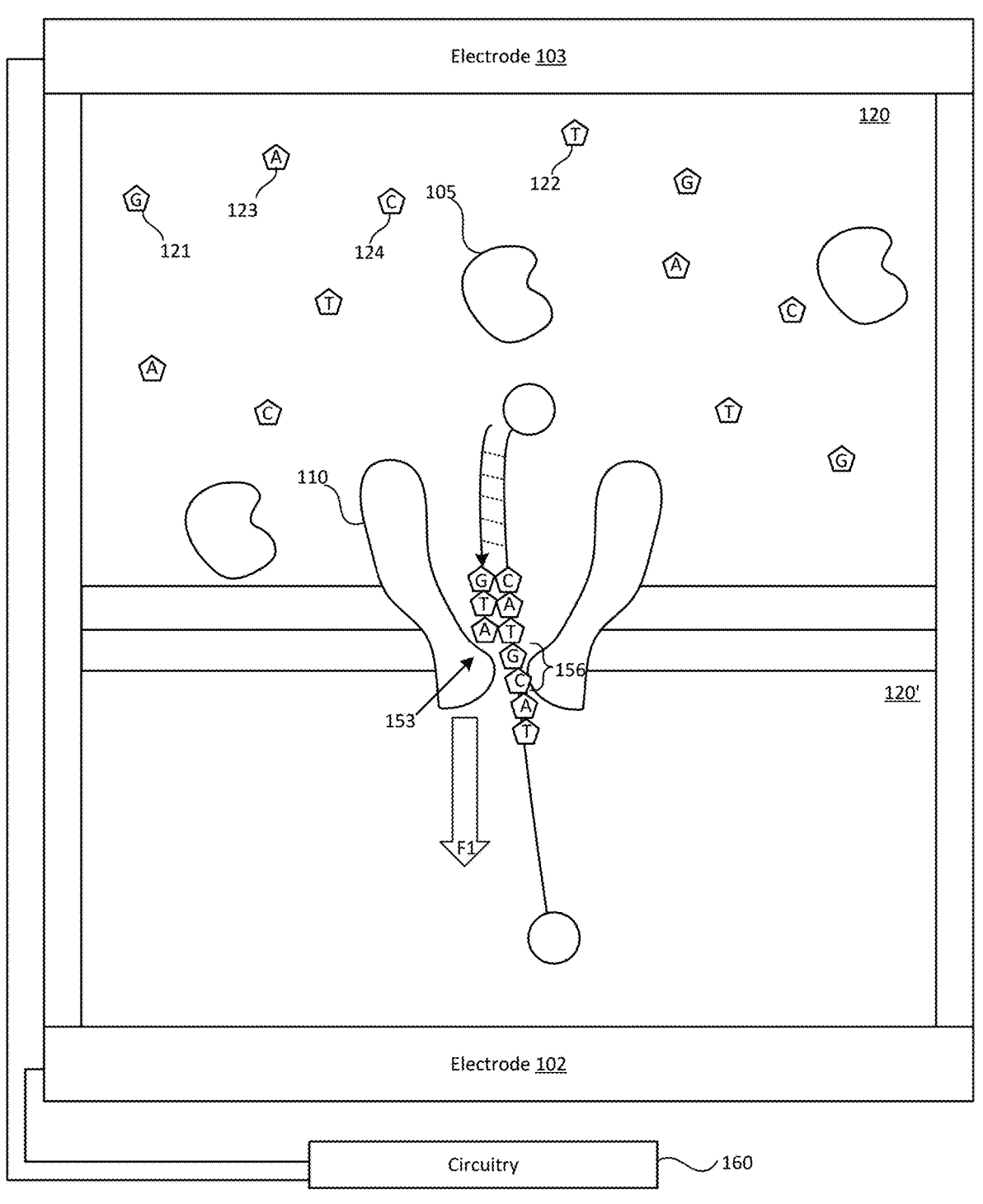
Figures 1F, 1G, 1H:
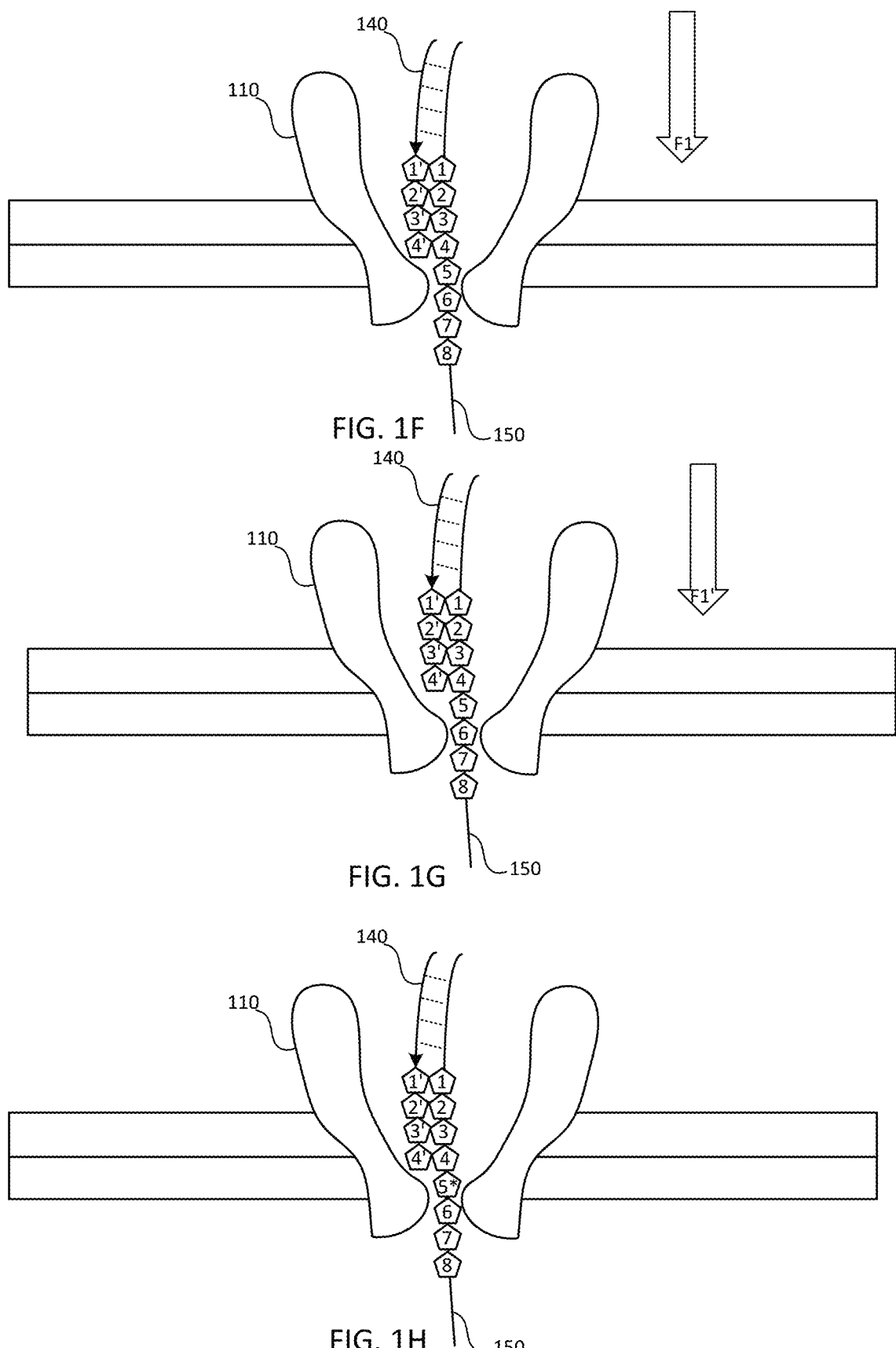

It will be appreciated that the particular number and locations of base(s) that affect the measured value may depend on the particular nanopore configuration used, the particular circuitry configuration used, and the particular conditions under which the measurement is performed. For example, as illustrated in FIG. 1G, under a modified first force (F1'), the 3' end of duplex 154 may be disposed at a different location relative to nanopore 110, e.g., may be disposed deeper within aperture 113 if F1' is greater than F1, or more shallowly within aperture 113 if F1' is less than F1 in the nonlimiting example shown in FIG. 1G. The ionic current through aperture 113 may be affected differently by the bases within the duplex 154 and the single-stranded portion 156 of polynucleotide 150, for different forces. In a manner such as described further below with reference to FIGS. 8A-8E, 9, and 10, the values of measurements made under different forces may be compared so as to even further enhance the accuracy with which nucleotides are identified.

In some examples, circuitry 160 is configured to identify at least one nucleotide within polynucleotide 150 as being modified such as, but not limited to, a methylated base. For example, referring now to FIG. 1H in which the numbers again are used to represent bases which may affect the measured value, it may be expected that if base 5* is methylated (or otherwise modified), such group may affect the measured value differently than would an unmethylated (or otherwise unmodified) base, and that therefore the presence of the methylated (or otherwise modified) base may be identified via its effect on the measured value.

Further details regarding the manner in which circuitry 160 may be used to identify nucleotides using the measured values are provided below with reference to FIGS. 8A-8E, 9, and 10.

Referring back to FIG. 1A, while the first force F1 is applied using circuitry 160, addition of a nucleotide to the 3' end 153 of duplex 154 may be inhibited. For example, fluid 120 may be in contact with the first side 111 of nanopore 110 and may include a plurality of nucleotides 121, 122, 123, 124, e.g., G, T, A, and C, respectively. Each of the nucleotides 121, 122, 123, 124 in fluid 120 optionally may be modified in a manner such as described in greater detail below, e.g., may be coupled to a respective blocking moiety or may include a nucleotide analogue. Fluid 120 further may include a plurality of polymerases 105 that may be used to add nucleotides to polynucleotide 140 using the sequence of polynucleotide 150 in a manner such as described with reference to FIG. 1B. However, at the particular time illustrated in FIG. 1A, aperture 113 of nanopore 110 may inhibit the addition of a nucleotide to 3' end 153 of duplex 154. For example, polymerases 105 may be sterically hindered from binding to 3' end 153 while the 3' end is located within aperture 113.

However, circuitry 160 may be configured so as to switch system 100 to an operational mode in which the 3' end of duplex 154 may be extended by adding a nucleotide. Such a nucleotide addition operation may be performed, for example, after forming duplex 154 and before applying the first force F1, e.g., to add nucleotide 121 prior to the particular time illustrated in FIG. 1A. FIG. 1B schematically illustrates an example mode for adding a nucleotide to duplex 154. In this mode, circuitry 160 may be configured to apply a second force F2 (such as a second voltage across nanopore 110 in a direction opposite that of the first voltage) that moves 3' end 153 of duplex 154 out of aperture 113 such that polymerase 105 may contact the 3' end of the duplex and may add a nucleotide thereto, e.g., T 122, based on the next nucleotide (e.g., A) in the sequence of polynucleotide 150. It will be appreciated that circuitry 160 instead may be configured to as to release the first force F1, following which release 3' end 153 of duplex 154 may naturally diffuse out of aperture 113 such that polymerase 105 may contact the 3' end of the duplex and may add a first nucleotide thereto, without the need to use the circuitry to actively apply a force causing such motion and making the 3' end of the duplex available to the fluid 120.

Note that any suitable type of polymerase 105 may be used to synthesize any suitable type of polynucleotide 140 based on any suitable type of polynucleotide 150. For example, a DNA polymerase 105 may be used copy a DNA polynucleotide 150 to form a DNA polynucleotide 140. Or, for example, an RNA polymerase 105 may be used to copy a DNA polynucleotide 150 to form an RNA polynucleotide 140. Or, for example, an RdRP (RNA dependent RNA polymerase) 105 may be used to copy an RNA polynucleotide 150 to form an RNA polynucleotide 140. Or, for example, a reverse transcriptase 105 may be used to copy an RNA polynucleotide 150 to form a DNA polynucleotide 140. Any DNA modifications may occur on the base or the sugar, including the 3' end. Any RNA modifications may occur on the base or the sugar, including the 2' end.

Example, but non-limiting, modifications to the 2' end include 2'-O-methoxy-ethyl, 2'-OMe, 2'-F and locked nucleic acid (LNA).

Circuitry 160 may be configured so as to repeatedly switch system 100 between a nucleotide addition mode (FIG. 1B), and a measurement mode (FIG. 1A). For example, after performing the measurement described with reference to FIG. 1A, another nucleotide may be added in a manner such as described with reference to FIG. 1B, and another measurement performed. During the measurement mode, the aperture or other feature of nanopore 110 may inhibit polymerase 105 from adding another nucleotide. As such, each cycle of nucleotide measurement may be controlled so as to have any desired duration, e.g., may be electronically controlled using circuitry 160, so as to provide an appropriate signal-to-noise ratio (SNR) for the type of measurement being performed. Generally, the longer the measurement cycle, the better the SNR that may be obtained. In some applications, circuitry 160 may be configured to adjust the length of the measurement mode so as to obtain a sufficiently high SNR (e.g., a SNR exceeding a predefined threshold), even though throughput (number of bases per unit time) may be lower. In other applications, circuitry 160 may be configured to adjust the length of the measurement mode so as to obtain a sufficiently high throughput (e.g., a throughout exceeding a predefined threshold), even though the SNR may be lower.

Circuitry 160 further may be configured to perform repeated cycles of nucleotide addition and measurement any suitable number of times. For example, as illustrated in FIG. 1C, after applying the second force F2 during which a nucleotide is added, circuit 160 again may apply the first force F1. The first force F1 may, in some examples, remove polymerase 105 from contact with 3' end 153 of the duplex 154, and moves the now-extended 3' end 153 of duplex 154 into the aperture 113 of nanopore 110, where constriction 114 or other feature of nanopore 110 inhibits translocation of the 3' end to second side 112 of the nanopore in a similar manner as described with reference to FIG. 1A. Alternatively, the first force F1 may be insufficient to remove the polymerase 105 from contact with 3' end 153 of duplex 154, and circuitry 160 may be configured to apply another force, which may be greater than the first force, to remove the polymerase from contact with the 3' end of the duplex.

In some examples, circuitry 160 is configured to measure binding of polymerase 105 to 3' end 153 of duplex 154 as a way of confirming that the polymerase is actually in the process of adding a nucleotide to the duplex, or has already added a nucleotide to the duplex. Such a confirmation may be useful, for example, when subsequent nucleotides are added that otherwise may yield the same or similar value of the electrical property as one another, and therefore otherwise may be difficult to distinguish from each other based solely on that value. For example, in a manner such as illustrated in FIG. 1D, circuitry 160 may apply a third force F3 disposing the polymerase, in contact with the 3' end of the duplex, within or adjacent to the aperture on the first side of the nanopore. While the third force F3 is applied, nanopore 110 may inhibit passage of the polymerase 105 into, or further into, the aperture. For example, polymerase 105 may be sterically hindered from entering aperture 113 at all, or by more than a limited amount (note that an actual polymerase may be significantly larger than those schematically illustrated in the present application, and indeed may be approximately the same diameter as nanopore 110 in some examples). The third force F3 may be applied in such a manner as to not strip polynucleotide 140 from polynucleotide 150. This could be achieved by keeping F3 below such stripping force, or in the event that F3 is greater than the force required for stripping, F3 is applied in a transient manner such that it does not permit time for the duplex 154 to dissociate.

During the operational mode illustrated in FIG. 1D, circuitry 160 may measure a value of an electrical property of polymerase 150 while applying the third force F3, and to identify contact of the polymerase with the 3' end of the duplex using the value measured. For example, the association of polymerase 105 with 3' end 153 may alter the rate at which salt in fluid 120 moves through aperture 113 and into fluid 120', and thus may alter the electrical current, the ionic current, electrical resistance (resistance to ion flow), or electrical voltage drop across nanopore 110, or the standard deviation of any such electrical characteristics, in such a manner as to be detected by circuitry 160. The third force F3 may be sufficient to move the complex including polymerase 105 and 3' end 153 towards and into contact with nanopore 110, and may be sufficiently low as not to remove the polymerase from 3' end 153. Additionally, or alternatively, circuitry 160 may determine whether there is a polymerase 105 still bound to the 3' end 153 of the duplex because if there is, then primarily single-stranded DNA will be within aperture 113 because the 3' end of the duplex will be held up at the top of the pore by the polymerase which is too large to enter the pore. After the measurement is made, then circuit 160 applies a suitable force so as to remove the polymerase 105 from the 3' end of the duplex, and a shift in signal may be observed to confirm removal of the polymerase as the 3' end of the duplex enters the pore. In some examples, F1 is stronger than F3 and may be in the same direction as F3. Circuit 160 may apply force F1 in such a manner as to dispose the single-stranded second portion 156 of polynucleotide 150 within aperture 113 for a measurement such as illustrated in FIG. 1E, which repeats the measurement described with reference to FIG. 1A but for the newly extended 3' end 153 and the newly shifted single-stranded second portion 156. Operations of adding a nucleotide to 3' end 153, optionally detecting the polymerase 105 in contact with 3' end 153, removing the polymerase, and measuring a value of an electrical property of the 3' end 153 of the duplex 154 and the single stranded second portion 156 of polynucleotide 150, from which value at least one nucleotide may be identified, may be repeated any suitable number of times, e.g., may be repeated along substantially the entire length of polynucleotide 150 to substantially sequence polynucleotide 150.

Note that in examples including constriction 114, although such constriction 114 occupies only a portion of the length of nanopore 110, it may be the most sensitive region for base discrimination, because the constriction is where the largest voltage drop occurs (as it presents the largest resistance between electrodes 102 and 103). Typical nanopore constrictions are longer than a single DNA nucleotide of a single-stranded polynucleotide, and therefore a current signal that a nanopore can generate may be dependent on more than one nucleotide, and typically 3, 4, 5, or even 6 or more nucleotides. These nucleotides form what may be termed a "K-mer." The number of possible K-mers for 4 bases of DNA is $4^K$. Some previously known strand sequencing methods operate by translocating a single strand of DNA through the constriction of a nanopore (i.e., the "sensing zone"), such as MspA or CsgG, and attempting to associate the currents created by each K-mer with the sequence of the K-mer. One method of performing this association is to create a table of each possible K-mer residing in the nanopore constriction at any time, and the associated current it creates, and then using a look-up table to find the K-mer that corresponds to a measured current. Another method of performing the associations is through the use of machine-learning algorithms. In practice there are several limitations to any method of K-mer based strand sequencing.

For example, two currents that correspond to unique K-mers may appear to be the same, or may be similar enough that they cannot be distinguished from one another within the bounds of a given experimental setup. The larger the K-mer, the more likely that such "degenerate" cases will occur. For this reason, the α-hemolysin nanopore presents challenges for strand sequencing because the K-mer is large, about 10 nucleotides, so there are about $4^{10}$ possible signals—far too many to be able to realistically deconvolve. For degenerate cases where the K-mers are somewhat shorter, about 6 nucleotides, other methods have sometimes been used to try to distinguish the K-mers. Translocating the DNA through the pore one nucleotide at a time, while permitting time to measure an electrical value for each nucleotide in succession, for example with the use of translocation enzymes (such as a helicase or polymerase), mitigates the K-mer problem. This so-called single-base ratcheting mitigates the K-mer problem because a given K-mer can transition to one of only four possibilities, because the base that leaves the sensing zone is replaced by A, C, G, or T, while the other bases remain unchanged within the sensing zone. For example, for a 4-mer such as ACGT, if the A leaves, CGT will change register, then as a new base enters, the new 4-mer can be only CGTT, CGTA, CGTC, or CGTG, whereas there are actually $4^4$ (256) K-mers that can be formed from four nucleotide types. Thus, the list of possibilities for the new K-mer is reduced from 256 to only 4, reducing the potential for degenerate signals.

Additionally, when homopolymer stretches in the template DNA translocate through the nanopore that are longer than the nanopore sensing zone (e.g., the K-mer length for a particular nanopore type), current strand sequencing methodologies may not be able to accurately determine the length of the homopolymer because there is no indication that the template DNA has translocated. In these cases, the length of time over which the homopolymer transits the nanopore has been attempted to be used to deduce the length of the homopolymer (by multiplying the time by the average number of nucleotides per time unit). However, translocation enzymes do not move at a consistent rate, so time alone may not provide sufficient accuracy for determining the length of the homopolymer. Indeed, because the speed at which the translocating enzymes move cannot be sufficiently controlled, and the time per nucleotide may be inconsistent, some translocation events may occur extremely rapidly and may be too short to be detectable using strand sequencing. As a result, deletion errors may occur.

The present subject matter mitigates any and all of such issues associated with strand sequencing, and indeed is believed to provide greatly enhanced accuracy, controllability, and repeatability as compared to strand sequencing.

For example, in a manner such as described with reference to FIGS. 1A-1H, the circuitry 160 measures a signal that is based on a combination of duplex 154 and a single-stranded portion 156 of polynucleotide 150, as well as the particular set of measurement conditions that are used. The information which is measured therefore is far richer than for an exclusively single-stranded polynucleotide under a single set of measurement conditions, e.g., as is the case in strand sequencing.

Through the use of the methods described herein to confirm the addition of a nucleotide to the 3' end of 153, the homopolymer issue is solved. For example, each time a new base is added to the 3' end 153 of duplex 154 (e.g., such as described with reference to FIGS. 1B and 1D), a discernible signal then is generated (e.g., such as described with reference to FIGS. 1A, 1C, and 1E) via which it may be confirmed that a single nucleotide was added. If the signals from different, sequentially added nucleotides are sufficiently similar or identical, then it may be inferred that a homopolymer stretch of polynucleotide 150 is being sequenced. Furthermore, different nucleotides within a given homopolymer stretch of polynucleotide 150 may yield different measured values of the electrical property, because each of such nucleotides may have different proximities to other, different nucleotides outside of the homopolymer stretch. Accordingly, even nucleotides of the same type, within a homopolymer, may be individually identified using the values that circuitry 160 measures.

Figure 3:
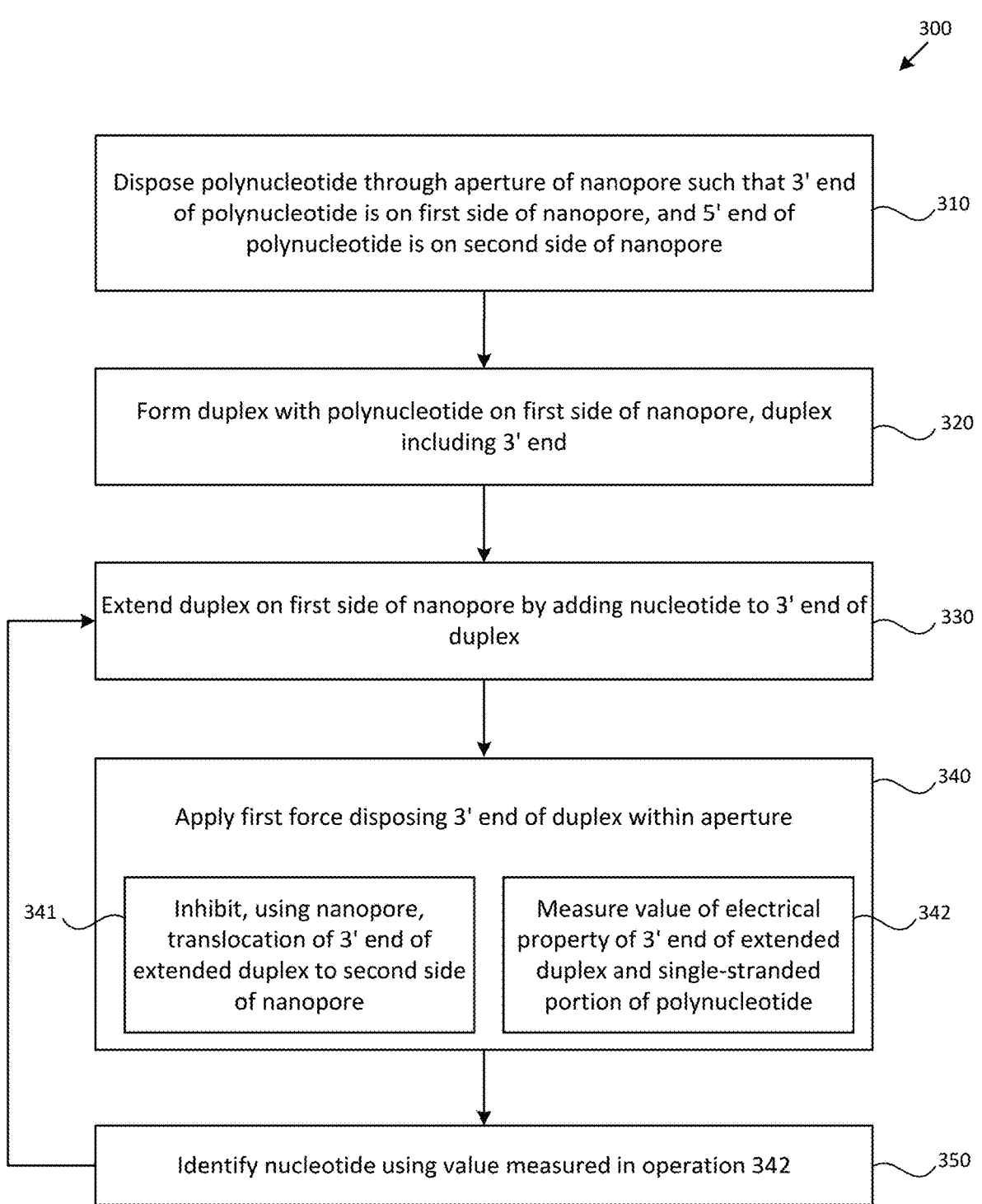
FIG. 3 illustrates a flow of operations in an example method for sequencing a polynucleotide.

Furthermore, during the present measurements such as described with reference to FIG. 1A, 3' end 153 (including the 3' end of polynucleotide 140) may be sequestered within aperture 113 or otherwise inaccessible for addition of another nucleotide until circuitry 160 applies an opposing force that frees 3' end 153 from the aperture 113 and makes the 3' end accessible to fluid, polymerase, and nucleotides for use in adding another nucleotide to 3' end 153.

The enzyme speed issue is also solved because the present systems and methods provide excellent control of the sequencing process. For example, circuitry 160 may electronically control the duration of the measurement operation to achieve a desired SNR (e.g., a SNR exceeding a predefined threshold) while inhibiting polymerase 105 from adding another nucleotide. Translocation of polynucleotide 150 through nanopore 110 also is controlled electronically using circuitry 160, and accordingly is not subject to variable kinetics of a translocation enzyme as is the case with strand sequencing, in which very fast translocation events may go undetected that may otherwise lead to deletion or other types of errors that affect accuracy.

Figures 8A, 8B, 8C:
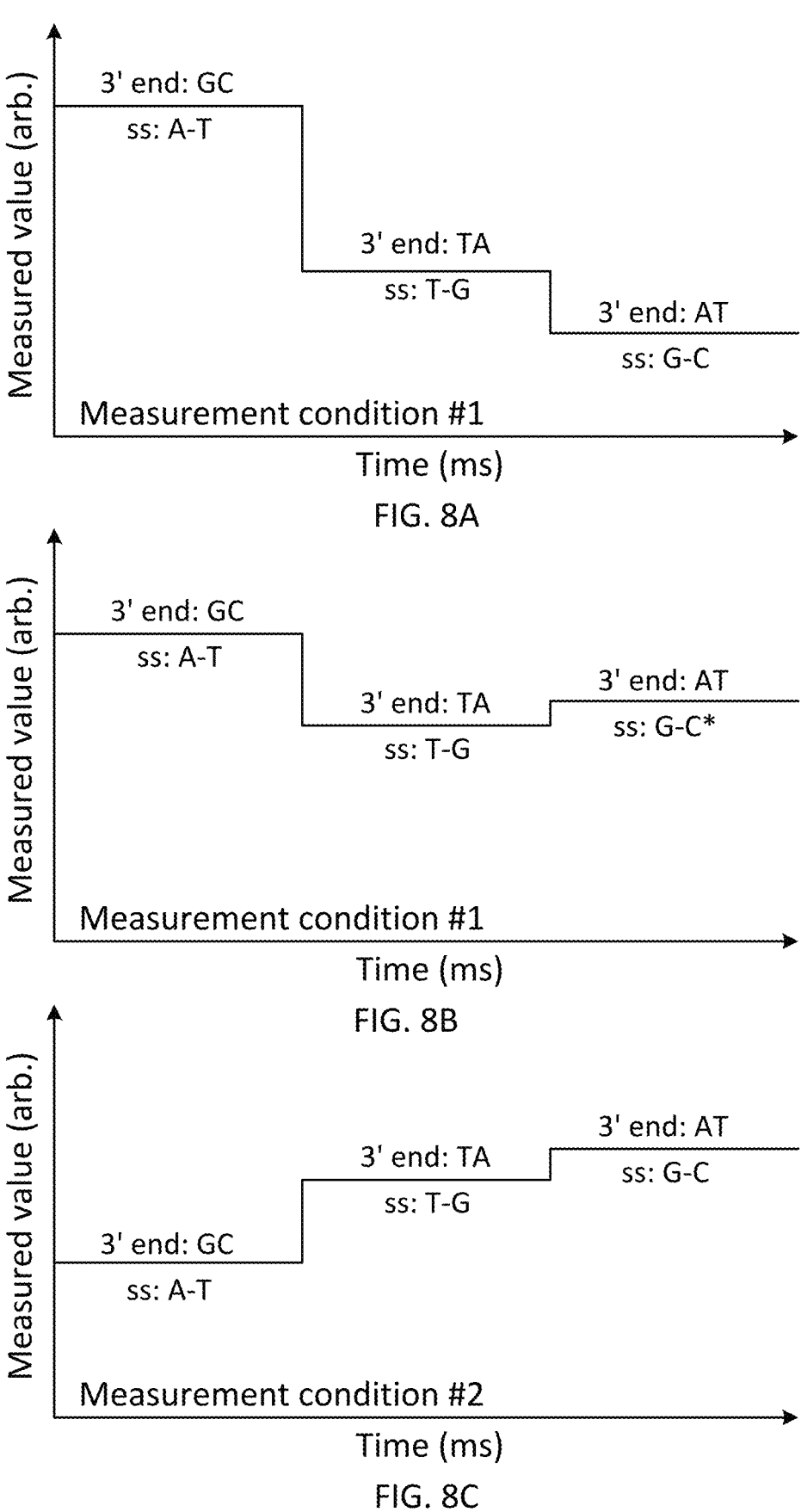
FIGS. 8A-8E illustrate example values of electrical characteristics that may be measured using the system of FIGS. 1A-1H.

For example, FIGS. 8A-8E illustrate example values of electrical characteristics that may be measured using the system of FIGS. 1A-1H. More specifically, FIG. 8A illustrates an example sequence of values that may be measured under a first set of measurement conditions as base pairs G (153) C (in 150 and paired to 153) (referred to herein as "GC"), T (153) A (in 150 and paired to 153) (referred to herein as "TA"), and A (153) T (in 150 and paired to 153) (referred to herein as "AT") respectively become located at the 3' end 153 of duplex 154, and sequences of nucleotides A-T, T-G, and G-C respectively become located in the single-stranded second portion 156 of polynucleotide 150, in a manner such as respectively described with reference to FIGS. 1A, 1C, and 1E. As illustrated in FIG. 8A, a first value is measured for the combination GC and A-T (FIG. 1A), a second value is measured for the combination TA and T-G (FIG. 1C), and a third value is measured for the combination AT and G-C (FIG. 1E). The particular types of nucleotides at the 3' end 153 of duplex 154, and in the sequences of nucleotides located in the single-stranded second portion 156 of polynucleotide 150 may affect the ionic current (and/or fluctuations in the ionic current) through nanopore 110 and therefore may affect the measured values.

Indeed, even the particular types of paired nucleotides that are within duplex 154 and spaced apart from the 3' end 153 of duplex 154, and/or the particular types of unpaired nucleotides that in polynucleotide 150 and are spaced apart from the single-stranded second portion 156 of polynucleotide 150, may affect the ionic current through nanopore 110 (and/or fluctuations in the ionic current or other noise) and therefore may affect the measured values. For example, FIG. 8B illustrates an example sequence of values that may be measured, again under the first set of measurement conditions, as base pairs GC, TA, and AT respectively become located at the 3' end 153 of duplex 154, and sequences of nucleotides A-T, T-G, and G-C* respectively become located in the single-stranded second portion 156 of polynucleotide 150, in a manner such as respectively described with reference to FIGS. 1A, 1C, and 1E, but in which C* is a nucleotide analogue, e.g., a methylated cytosine. As illustrated in FIG. 8B, a first value is measured for the combination GC and A-T (FIG. 1A), a second value is measured for the combination TA and T-G (FIG. 1C), and a third value is measured for the combination AT and G-C* (FIG. 1E). The first value in FIG. 8B may be similar to the first value in FIG. 8A, for example because C* is separated from the 3' end of the duplex by three bases, and therefore may not significantly affect the ionic current through nanopore 110. The second value in FIG. 8B may differ somewhat from the second value in FIG. 8A, for example because C* may somewhat affect the ionic current through nanopore 110, relative to how unmethylated C may affect such current, even though it is separated from the 3' end of the duplex by two bases. The third value in FIG. 8B may differ significantly from the third value in FIG. 8A, for example because C* may significantly affect the ionic current through nanopore 110, relative to how unmethylated C may affect such current, because it is directly adjacent to the 3' end of the duplex.

Different sets of measurement conditions also may affect the values which are measured for different combinations of nucleotides at the 3' end 153 of the duplex 154 and in the single-stranded second portion 156 of polynucleotide 150. For example, in a manner such as described with reference to FIG. 1G, applying a different force using circuitry 160 may move the 3' end 153 of the duplex 154, and the second portion 156 of polynucleotide 150, to a different location relative to nanopore 110 at which nucleotides in the duplex 154 and polynucleotide 150 may affect the ionic current (and/or fluctuations in the ionic current or other noise) differently than they do at another location (under another force). Changes in the measurement conditions may linearly or nonlinearly affect the measured values, and indeed may change the measured values in different directions for different combinations of nucleotides at the 3' end 153 of the duplex 154 and within the second portion 156 of polynucleotide 150.

For example, FIG. 8C illustrates an example sequence of values that may be measured, under a second set of measurement conditions that differs from the first set of measurement conditions, as base pairs GC, TA, and AT respectively become located at the 3' end 153 of duplex 154, and sequences of nucleotides A-T, T-G, and G-C respectively become located in the single-stranded second portion 156 of polynucleotide 150, in a manner such as respectively described with reference to FIGS. 1A, 1C, and 1E. As illustrated in FIG. 8C, a first value is measured for the combination GC and A-T (FIG. 1A), a second value is measured for the combination TA and T-G (FIG. 1C), and a third value is measured for the combination AT and G-C (FIG. 1E). The first value in FIG. 8C may be different from the first value in FIG. 8A, the second value in FIG. 8C may be different from the second value in FIG. 8A, and the third value in FIG. 8C may be different from the third value in FIG. 8A, even though the sequences are the same, for example because the second set of measurement conditions affects the ionic current through nanopore 110 in a manner that is different, for each combination of nucleotides, than does the first set of measurement conditions. In this nonlimiting example, the second set of measurement conditions decreases the first value, increases the second value, and increases the third value, relative to those values under the first set of measurement conditions.

Because the measured values are highly reproducible and accurate, even though sequencing the same polynucleotide 150 under two or more different sets of measurement conditions may provide different sequences of measured values that may be nonlinearly related to the particular measurement conditions used, it is expected that each such sequence of measured values reliably may be used to identify the sequence of nucleotides in polynucleotide 150. Indeed, in a manner such as described with reference to FIG. 9, polynucleotide 150 may be sequenced multiple times under different sets of measurement conditions, and/or may be sequenced using multiple sets of conditions during a single round of sequencing polynucleotide 150, and the sequences compared to one another to further improve the accuracy of the sequence.

Figures 8D, 8E, 9:
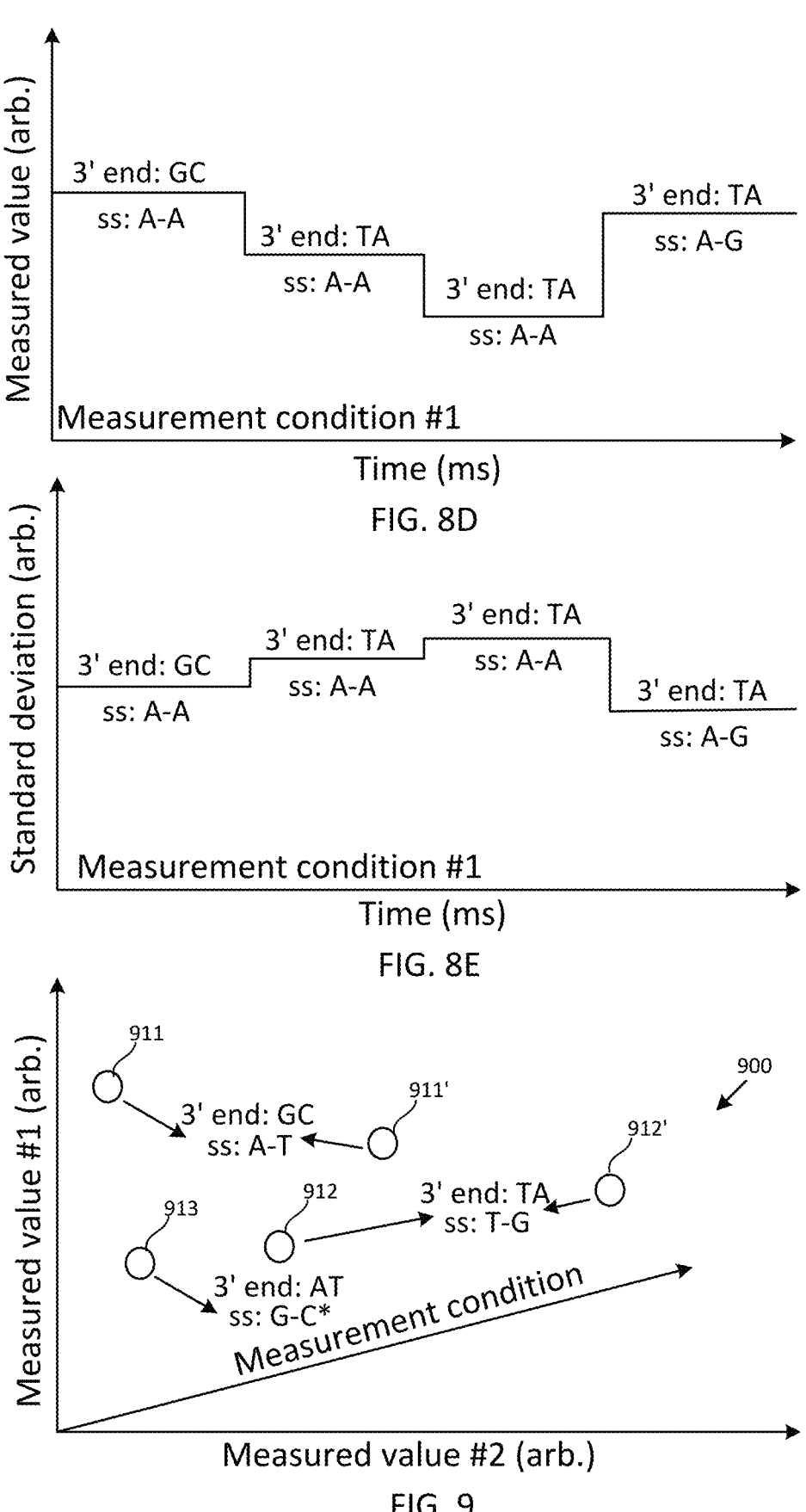
FIG. 9 illustrates an example N-dimensional read map of electrical characteristics that may be used to identify nucleotides using the system of FIGS. 1A-1H.

As further noted above, multiple aspects of the present systems and methods address the homopolymer issue. One such aspect is the contribution of signal from the duplex, as well as from surrounding nucleotides, to the particular value of the signal that may obtained within a given portion of the polymer. For example, FIG. 8D illustrates an example sequence of values that may be measured for the polynucleotide sequence CAAAG in polynucleotide 150, in which the base pair GC initially is located at the 3' end of the duplex, to which the nucleotides TTT sequentially are added so that the base pairs TA, TA, TA sequentially become located at the 3' end of the duplex and the polynucleotide sequences A-A, A-A, and A-G sequentially become located within the single-stranded second portion 156 of polynucleotide 150. As illustrated in FIG. 8D, under a first set of measurement conditions, a first value is measured for the combination GC and A-A, a second value is measured for the combination TA and A-A, a third value is measured for the combination TA and A-A, and a fourth value is measured for the combination TA and A-G. The particular types of nucleotides at the 3' end 153 of duplex 154, and in the sequences of nucleotides located in the single-stranded second portion 156 of polynucleotide 150 may affect the ionic current (and/or fluctuations in the ionic current) through nanopore 110 and therefore may affect the measured values. Indeed, even the particular types of paired nucleotides that are within duplex 154 and spaced apart from the 3' end 153 of duplex 154, and/or the particular types of unpaired nucleotides that within polynucleotide 150 and are spaced apart from the single-stranded second portion 156 of polynucleotide 150, may affect the ionic current through nanopore 110 (and/or fluctuations in the ionic current) and therefore may affect the measured values.

For example, although during the first and second measurements A-A is located within the single-stranded second portion 156 of polynucleotide 150, the presence of different base pairs GC and TA at the 3' end 153 of the duplex 154 provide signal contributions that allow the first A-A to be readily distinguished from the second A-A. Furthermore, although during the second and third measurements TA is located at the 3' end 153 of the duplex 154 and A-A is located within the single-stranded second portion 156 of polynucleotide 150, the presence of different base pairs at locations that are within duplex 154 and spaced apart from the 3' end 153 of duplex 154, and/or different unpaired nucleotides that are within polynucleotide 150 and spaced apart from the single-stranded second portion 156 of polynucleotide 150, provide signal contributions that allow the first combination of TA and A-A to be readily distinguished from the second combination of TA and A-A.

Accordingly, it will be appreciated that signal contributions from different portions of the duplex 154 and/or from additional unpaired bases in the sequence of polynucleotide 150 may be used to distinguish different nucleotides in a homopolymer sequence from one another. In this regard, referring back to FIGS. 1F and 1G, the greater the values of M and/or D, the longer the sequence or "word" that may be read at a given time, the longer the homopolymer stretches that may be reliably read because the more unpaired nucleotides and/or duplex base pairs may contribute to signals by which the nucleotides of the homopolymer may be distinguished from one another. It will be appreciated that the sequence of measurements illustrated in FIG. 8D may be repeated under a different set of measurement conditions, to obtain a different set of values that may distinguish the nucleotides in the homopolymer sequence from one another in a different way.

Although different combinations of nucleotides and/or duplex base pairs may affect the magnitude of the ionic current through a nanopore, such combinations also or alternatively may affect fluctuations of the ionic current through the nanopore, or noise. Circuitry 160 may measure such fluctuations or noise and use the measured values of those fluctuations or noise to identify nucleotides. As such, the fluctuations may be considered to be an electrical property of the 3' end 153 of the duplex 154 and the second portion 156 of the polynucleotide 150, although such fluctuations sometimes may be referred to as a "standard deviation" in the magnitude of another measurement in order to facilitate a discussion of certain distinctions between the information obtained from such fluctuations, and the information obtained from the magnitude of the measurement. For example, FIG. 8E illustrates an example sequence of standard deviation values that may be measured for the same sequence described with reference to FIG. 8D. As illustrated in FIG. 8E, under the first set of measurement conditions, a first value of the standard deviation is measured for the combination GC and A-A, a second value of the standard deviation is measured for the combination TA and A-A, a third value of the standard deviation is measured for the combination TA and A-A, and a fourth value of the standard deviation is measured for the combination TA and A-G. The particular types of nucleotides at the 3' end 153 of duplex 154, and/or the particular types of nucleotides in the sequences of nucleotides located in the single-stranded second portion 156 of polynucleotide 150, may affect the fluctuations in the ionic current through nanopore 110 and therefore may affect the measured standard deviation values. Indeed, even the particular types of nucleotides that are within duplex 154 and spaced apart from the 3' end 153 of duplex 154, and/or the particular types of unpaired nucleotides that are within polynucleotide 150 and spaced apart from the single-stranded second portion 156 of polynucleotide 150, may affect the fluctuations in the ionic current, and therefore may affect the measured standard deviation values. As such, the standard deviations of measured values may be used alone, or may be used together with, the magnitudes of the measured values to identify the sequence of polynucleotide 150. It will be appreciated that the sequence of measurements illustrated in FIG. 8E may be repeated under a different set of measurement conditions, to obtain a different set of standard deviation values that may distinguish the nucleotides in the homopolymer sequence (or any other sequence) from one another in a different way.

For example, as provided herein, measurements such as described with reference to FIGS. 8A-8E may be used to generate a data structure, such as an N-dimensional "read map," that correlates measured values—each of which may have any desired level of accuracy and may be obtained under any suitable set of measurement conditions—with different combinations of sequences within duplex 154 and the second portion of polynucleotide 150. For example, FIG. 9 illustrates an example N-dimensional read map of electrical characteristics that may be used to identify nucleotides using the system of FIGS. 1A-1H. In the nonlimiting example illustrated in FIG. 9, read map 900 includes a first axis corresponding to a first type of measured value, a second axis corresponding to a second type of measured value (e.g., the standard deviation of the same type of measured value as the first axis), and a third axis corresponding to a given measurement condition that may be varied between different measurements. Illustratively, the measurement condition may be or include application of a first force F1 such as described with reference to FIGS. 1A, 1C, 1E, and 1F, and the measurement condition may be varied (changed along the respective axis in FIG. 9) by applying a modified first force F1', such as described with reference to FIG. 1G, that positions the 3' end 153 of the duplex 154 differently relative to nanopore 110, thus causing a change in one or more measured values and/or in the noise or fluctuations in ionic current, e.g., in the standard deviation of the same or a different one or more measured values.

N-dimensional read map 900 illustrated in FIG. 9 may be generated using a calibration procedure in which a sufficient number of different polynucleotides, the sequences of which are known a priori, are sequenced using measurement operations and nucleotide addition operations in a manner such as describe with reference to FIGS. 1A-1E. Such a calibration procedure may be performed on a per-system basis, or may be performed in such a manner that the points in read map 900 apply approximately equally to each of a plurality of systems, such that each system need not be individually calibrated to generate its own read map. For example, at a first measurement condition, circuitry 160 may measure the values of one or more electrical properties of the 3' end 153 of the duplex 154 and the second portion 156 of polynucleotide 150, such as an electrical current, an ionic current, an electrical resistance, or an electrical voltage drop across nanopore 110, and/or the standard deviations of one or more of such electrical properties, between nucleotide addition steps. Circuitry 160 may store the measured values and the measurement condition in a non-volatile computer readable medium (e.g., memory), and this set of information may be considered to populate a first plane of points in read map 900. Then, at a second (different) measurement condition, circuitry 160 may measure the values of one or more electrical properties of the 3' end 153 of the duplex 154 and the second portion 156 of polynucleotide 150, and/or the standard deviations of one or more of such electrical properties, between nucleotide addition steps. Circuitry 160 may store the measured values and the measurement condition in the computer readable medium (e.g., memory), and this set of information may be considered to populate a second plane of points in read map 900. Such operations of measuring and storing measurement values and the respective measurement condition may be repeated any suitable number of times to provide read map 900 with the desired number of dimensions.

For each of the points that are stored in read map 900, circuitry 160 also may store the identities and respective locations in the sequence of the nucleotide(s) which are known to have contributed to that signal because the sequences of the polynucleotides are known a priori. For example, for each of the points stored in read map 900, circuitry 160 may store the identities and locations in the sequence at least of nucleotides 4, 4', 5, and 6 illustrated in FIG. 1F. Optionally, circuitry 160 also may store the identities of nucleotides 3 and 3'. As a further option, circuitry 160 also may store the identities and locations in the sequence of nucleotides 2 and 2'. As a still further option, circuitry 160 also may store the identities and locations in the sequence of nucleotides 1 and 1'. Additionally, or alternatively, circuitry 160 also may store the identity and location in the sequence of nucleotide 7. As a further option, circuitry 160 also may store the identity and location in the sequence of nucleotide 8. Nonlimiting examples of the numbers and locations of nucleotides that may contribute to the measured signal, and thus may be stored within read map 900, are described with reference to FIGS. 1F-1G.

As a purely illustrative example, for point 911 in the read map defined by the measured value and standard deviation of electrical current through nanopore 110 at a first set of measurement conditions (e.g., first force F1) illustrated in FIG. 1A, and for point 911' corresponding to the same measurements at a second set of measurement conditions (e.g., modified first force F1' described with reference to FIG. 1G), circuitry 160 may store the nucleotides and their locations in a format such as G C A T, where it is defined by convention that the first listed nucleotide corresponds to nucleotide 4' which is located at the 3' end 153 of duplex 154, the second listed nucleotide corresponds to nucleotide 4 which is the base pair of nucleotide 4', the third listed nucleotide corresponds to nucleotide 5 which is unpaired and adjacent to the base pair, and the fourth listed nucleotide corresponds to nucleotide 6 which is unpaired and adjacent to nucleotide 5. Similarly, for point 912 in the read map defined by the measured value and standard deviation of electrical current through nanopore 110 at a first set of measurement conditions (e.g., first force F1) illustrated in FIG. 1C, and for point 912' corresponding to the same measurements at a second set of measurement conditions (e.g., modified first force F1' described with reference to FIG. 1G), circuitry 160 may store the nucleotides and their locations in a format such as T A T G, using the same convention. Of course, any other suitable format may be used, and any suitable number of nucleotides may be included and their identities and locations indicated in any suitable manner.

Note that methylated bases, or other modified nucleotides, may be included in the polynucleotides at locations that are known a priori, and the calibration procedure performed. In a manner such as described with reference to FIGS. 1H and 8C, one or more of the values that are measured from sequences including such modified nucleotides may be different from the values that are measured from sequences including unmodified nucleotides. The identity of the nucleotide which circuitry 160 stores may include a suitable indication of whether and how the nucleotide is modified. For example, point 913 in read map 900 may be defined by the measured value and standard deviation of electrical current through nanopore 910 at a first set of measurement conditions (e.g., first force F1) for a sequence including AT at the 3' end, G at location 5, and methylcytosine (C*) at location 6. It may be seen that point 913 may have a different location in read map 900 than may another point for which the cytosine is unmodified, as well as may yet another point for which the cytosine includes a different type of modification.

It will be appreciated that while the inclusion of a plurality of measured value axes (e.g., both a measured value and a standard deviation) in read map 900 may enhance the accuracy with which circuit 160 identifies nucleotides, in some examples only a single such axis, corresponding to a single type of measured value, is included in read map 900. Conversely, read map 900 may include any suitable number of dimensions, e.g., axes corresponding to any suitable number and types of measured values, standard deviations of measured values, measurement conditions (such as temperature, fluid composition such as salt concentration and/or pH, location in flow cell), types of (e.g., variants of) nanopores, types of (e.g., variants of) polymerases, nucleotide modifications, and the like.

Read map 900 (or other suitable data structure such as described elsewhere herein) may be stored in non-volatile computer-readable memory in operable communication with circuitry 160, and circuitry 160 repeatedly may use the read map to identify individual nucleotides in the sequence of polynucleotide 150, e.g., as nucleotides are added to the 3' end 153 of duplex 154. For example, in a manner such as described with reference to FIGS. 1A, 1C, and 1E, circuit 160 may measure the values of one or more electrical properties of the 3' end 153 of duplex 154 and the single-stranded second portion 156 of polynucleotide 150 under a given set of measurement conditions. In some examples, circuit 160 may be programmed to use sets of measurement conditions for which read map 900 contains points, so as to facilitate comparison of values that are measured for unknown sequences to values that were previously measured for sequences that were known a priori. In some examples, circuit 160 may locate the set (e.g., plane) of points in the read map corresponding to that set of measurement conditions, may compare the measured value(s) to the corresponding set of values in the read map, and based upon such comparison may select the value or combination of values in that set that is/are closest to the measured value. Then, for the selected value(s), circuit 160 may retrieve the identities and locations of the nucleotides that generated the value(s) during the calibration step. Illustratively, circuit 160 may determine that the measured value(s) for the unknown polynucleotide sequence is closest in magnitude to the value(s) for point 911 in read map 900. Based upon such comparison, circuit 160 may determine that the unknown polynucleotide sequence includes the base pair GC at the 3' end 153 of the duplex 154 (locations 4' and 4, respectively), A at location 5, and T at location 6. Such a determination may be referred to as a "base call."

Note, however, that circuitry 160 is not limited to using a single point in read map 900 to make a base call, although that is an option. Instead, circuitry 160 may use multiple points within read map in order to significantly enhance the accuracy of the base call. For example, as may be understood from comparing FIGS. 1A, 1B, and 1C, the nucleotide that is added to the 3' end 153 of duplex 154 shifts the single-stranded second portion 156 of polynucleotide 150 upward by a single nucleotide. As such, the sequence of single-stranded second portion 156 in FIG. 1A and the sequence of single-stranded second portion 156 in FIG. 1C overlap with one another by at least one nucleotide—in this example, the T which shifts from position 6 in FIG. 1A to position 5 in FIG. 1C. Circuitry 160 may compare the base call from the measurement made at the time of FIG. 1A to the base call from the measurement made at the time of FIG. 1C, to confirm whether the same nucleotide(s) are present but are shifted in location by a single nucleotide, as should be the case if (i) a single nucleotide was added in the operation illustrated in FIG. 1B and (ii) the base calls made for FIGS. 1A and 1C were both correct. If, based upon such a comparison, circuitry 160 determines that the base calls between addition of a nucleotide are consistent with one another (e.g., contain sequences that are shifted by one nucleotide), then circuitry 160 may proceed with the sequencing process. On the other hand, if circuitry 160 determines that these base calls are inconsistent with one another, then the circuitry may flag this portion of the sequence as containing an error, may attempt to make the base call again, or even to resequence the polynucleotide in a manner such as described elsewhere herein. Note that for a sufficiently long homopolymer stretch, there may not necessarily be any change in the signals. In this case, other information provided by the present systems and methods still may be used to confirm the individual addition of nucleotides in a manner such as described elsewhere herein.

Circuitry 160 also, or alternatively, may use multiple measurements in order to locate the closest point within read map 900. For example, circuitry 160 may make another base call for the same sequence, but using a second, different set of measurement conditions for which read map 900 contains points, so as to facilitate comparison of values that are measured for unknown sequences to values that were previously measured for sequences that were known a priori. Circuitry 160 may impose the second set of measurement conditions shortly after imposing a first set of measurement conditions, e.g., may apply first force F1 and then may apply modified first force F1' before adding another nucleotide. Alternatively, circuitry 160 may impose the second set of measurement conditions while resequencing polynucleotide 150 in a manner such as described elsewhere herein. Circuitry 160 may compare the base call from the measurement made with the first set of measurement conditions to the base call from the measurement made with the same set of measurement conditions, to confirm whether the same nucleotide(s) are present at the same locations in both base calls, which should be the case if both of the base calls were correct. For example, base calls made using points 911 and 911' in read map 900 will be consistent, while a base call made using point 911 and a base call made using point 912' will be consistent. If, based upon such a comparison, circuitry 160 determines that the base calls for different measurement conditions are consistent with one another (e.g., contain the same sequences), then circuitry 160 may proceed with the sequencing process. On the other hand, if circuitry 160 determines that these base calls are inconsistent with one another, then the circuitry may flag this portion of the sequence as containing an error, may attempt to make one or both of the base calls again, or even to resequence the polynucleotide in a manner such as described elsewhere herein.

Although read map 900 is illustrated graphically for purposes of discussion, it should be understood that the points in read map suitably may be stored any suitable format, within a non-volatile computer-readable medium, that correlates a given measurement condition with one or more values that were measured under that condition and combinations of duplex and single-stranded sequences that were used to generate those values. A look-up table (LUT) is a non-limiting example of a format that may be used to store correlations between measured values and known combinations of duplex and single-stranded sequences that were used to generate those values. However, it will be understood that any suitable data structure may be used to store correlations between measured values and known combinations of duplex and single-stranded sequences that were used to generate those values. For example, the data structure may be generated by, and appropriately stored for use by, a machine learning algorithm. For example, the data structure may be generated by training a machine learning algorithm to recognize values that are obtained, under each respective given set of measurement conditions, and are known a priori to correspond to respective combinations of duplex and single-stranded sequences, and may be stored in any suitable format within a non-volatile computer-readable medium. The data structure subsequently may be used by the trained machine learning algorithm, implemented by circuitry 160, to generate an output that identifies nucleotides in the sequence of polynucleotide 150, based upon an input of values that are measured in between nucleotide addition steps such as described with reference to FIGS. 1A-1H. It will be appreciated that circuitry 160 may be used to train the machine learning algorithm, or different circuitry may be used to train the machine learning algorithm that then is implemented by circuitry 160. In certain examples, the data structure may be generated by, and appropriately stored for use by, a neural network, such as a deep learning algorithm. For example, the data structure may be generated by training a neural network (e.g., deep learning algorithm) to recognize values that are obtained, under each respective set of measurement conditions, and are known a priori to correspond to respective combinations of duplex and single-stranded sequences, and may be stored in any suitable format within a non-volatile computer-readable medium. Accordingly, the data structure may include neurons of the neural network (e.g., deep learning algorithm). The data structure subsequently may be used by the trained neural network (e.g., deep learning algorithm), implemented by circuitry 160, to generate an output that identifies nucleotides in the sequence of polynucleotide 150, based upon an input of values that are measured in between nucleotide addition steps such as described with reference to FIGS. 1A-1H. It will be appreciated that circuitry 160 may be used to train the neural network (e.g., deep learning algorithm), or different circuitry may be used to train the neural network (e.g., deep learning algorithm) that then is implemented by circuitry 160.

Figure 10:
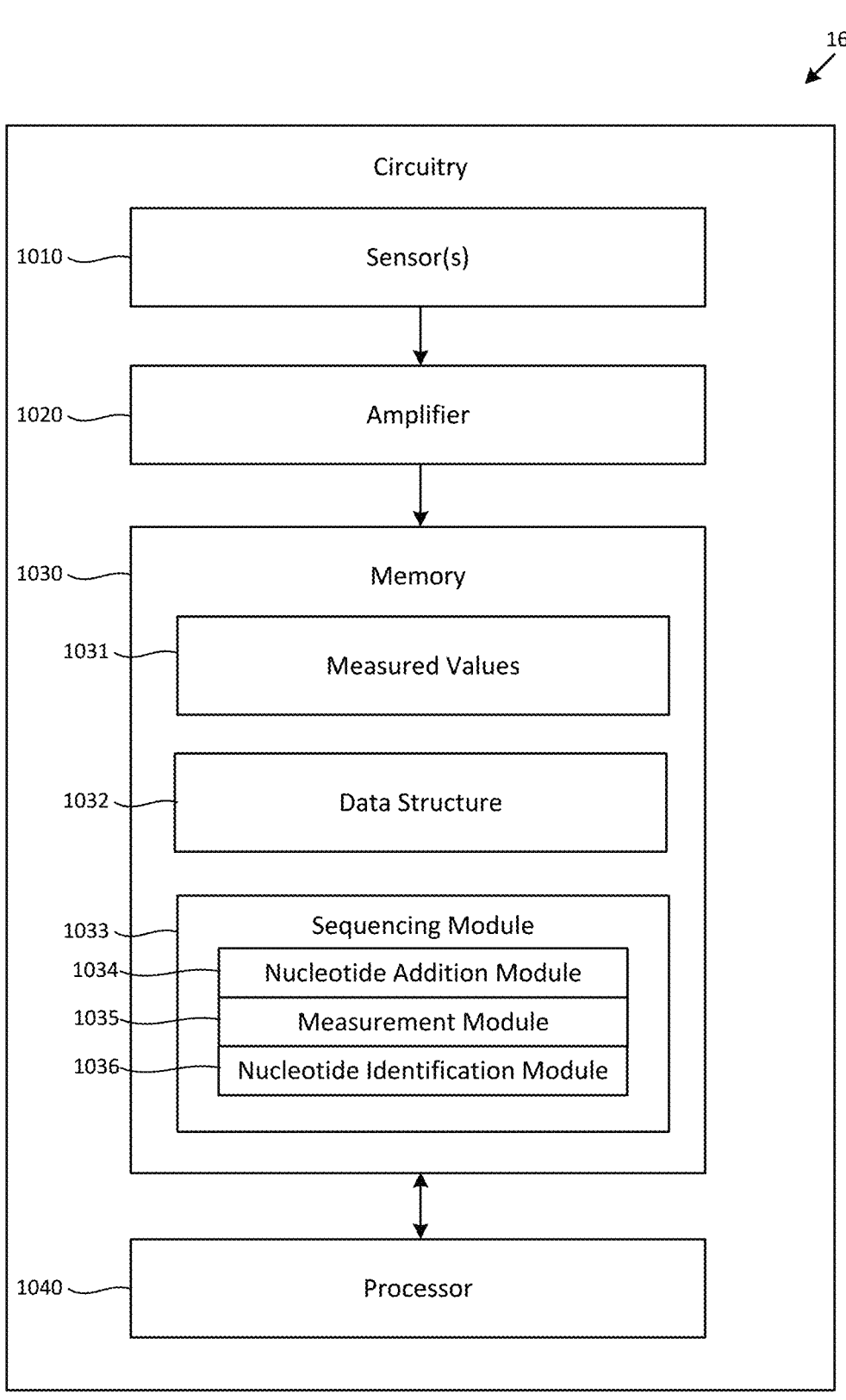
FIG. 10 schematically illustrates example circuitry that may be used in the system of FIGS. 1A-1H.

It should be noted that operations such as described herein, e.g., operations for measuring values, adding nucleotides, and identifying nucleotides, can be executed using any suitable combination of hardware and software. For example, FIG. 10 illustrates an example circuit 160 for sequencing an unknown polynucleotide in a manner such as provided herein. Circuit 160 may include processor 1040 and at least one computer-readable medium 1030. The computer-readable medium 1030 may store a plurality of measured values 1031 of an electrical property of a 3' end of a duplex including a first portion of the unknown polynucleotide and a second portion of the known polynucleotide within an aperture of a nanopore. The computer-readable medium 1030 may store a data structure 1032 (e.g., read map 900 or trained neurons), wherein the data structure correlates different measured values with different combinations of nucleotides within a 3' end 153 of a duplex 154 including a first portion 155 of a known polynucleotide and a second portion 156 of the known polynucleotide within an aperture 113 of a nanopore 110. Data structure 1032 further may identify a respective measurement condition under which the measured values were obtained, e.g., the magnitude of a bias voltage used to impose first force F1 or modified first force F1' during the measurement. Data structure 1032 further may identify the combination of nucleotides (e.g., at least at locations 4 and 4' at the 3' end 153 of the duplex 154 and at locations 5 and 6 illustrated in FIG. 1F) that provided each of the measured values.

The computer-readable medium 1030 also may store instructions for causing processor 1040 to implement operations such as provided herein. For example, the instructions may be for causing processor 1040 to compare the plurality of measured values to the values within a data structure (such as read map 900 or trained neurons), to determine the sequence of nucleotides in the sequence of the unknown polynucleotide using the comparisons; and to output a representation of the determined sequence of nucleotides. Illustratively, the instructions may be provided within sequencing module 1033. Sequencing module 1033 may include nucleotide addition module 1034 configured to cause processor 1040 to add a nucleotide to the 3' end 153 of duplex 154 in a manner such as described with reference to FIGS. 1B and 1D. For example, circuit 160 may be operably coupled to electrodes 102 and 103. Nucleotide addition module 1034 may cause processor 1040 to apply second force F2 by applying a suitable voltage bias across electrodes 102 and 103. Sequencing module 1033 may include measurement module 1035 configured to cause processor 1040 to measure, in between nucleotide addition operations, values of an electrical property of a 3' end 153 of a duplex 154 including a first portion of the unknown polynucleotide and a second portion of the known polynucleotide within an aperture of a nanopore in a manner such as described with reference to FIGS. 1A, 1C, and 1E, and to store the measured values within computer-readable medium 1031. For example, measurement module 1035 may cause processor 1040 to apply first force F1 or modified first force F1' by applying a suitable voltage bias across electrodes 102 and 103, and measuring the value of the electrical property while applying such force.

Circuitry 160 may include one or more sensor(s) 1010, each configured to measure the value of one or more electrical properties. Each sensor 1010 may be configured to measure, for example, an electrical voltage drop across nanopore 110, an electrical current through nanopore 110, or an electrical resistance across nanopore 110, or an intensity of light from a dye the emission from which changes responsive to the amount of ionic current through nanopore 110. Optionally, each sensor 1010 further may be configured to measure the standard deviation of the metric which it is measuring, for example, the standard deviation of an electrical voltage drop across nanopore 110, the standard deviation of an electrical current through nanopore 110, or the standard deviation of an electrical resistance across nanopore 110, or the standard deviation of an intensity of light from a dye the emission from which changes responsive to the amount of ionic current through nanopore 110. Alternatively, measurement module 1035 may be configured to determine the standard deviation of such metrics based on statistical analyses of measured values 1031. Measured values 1031 further may identify a measurement condition under which the measured values were obtained, e.g., the magnitude of a bias voltage used to impose first force F1 or modified first force F1' during the measurement.

In examples in which the measured value is electrical in nature, sensor 1010 may include one or both of electrodes 102 and 103 or may include one or more additional electrodes or other circuit component(s) respectively in contact with fluid 120 and/or fluid 120'. In examples in which the measured value is electrical in nature, the circuit component(s) in contact with fluid 120 and/or fluid 120' may include a field effect transistor configured to sense a voltage drop across fluid 120 and fluid 120'. In examples in which the measured value is optical in nature, sensor 1010 may include any suitable optical detector, such as an active-pixel sensor (APS) including an array of amplified photodetectors configured to generate an electrical signal based on light received by the photodetectors. APSs may be based on complementary metal oxide semiconductor (CMOS) technology known in the art. CMOS-based detectors may include field effect transistors (FETs), e.g., metal oxide semiconductor field effect transistors (MOSFETs). In particular examples, a CMOS imager having a single-photon avalanche diode (CMOS-SPAD) may be used, for example, to perform fluorescence lifetime imaging (FLIM). In other examples, the optical detector may include a photodiode, such as an avalanche photodiode, charge-coupled device (CCD), cryogenic photon detector, reverse-biased light emitting diode (LED), photoresistor, phototransistor, photovoltaic cell, photomultiplier tube (PMT), quantum dot photoconductor or photodiode, or the like. Each sensor 1010 generates an electrical signal corresponding to the measured value, and provides that signal to memory 1030 for storage at 1031. Optionally, circuitry 160 includes amplifier(s) 1020 respectively configured to amplify the electrical signal(s) from respective sensor(s) 210 prior to storage of that signal at 1031; as a further option, an amplifier 1020 may be included within a respective sensor 1010.

Sequencing module 1033 also may include nucleotide identification module 1036 configured to cause processor 1040 to identify nucleotides by comparing the measured values 1031 to values within data structure 1032, e.g., in a manner such as described with reference to FIGS. 8A-8E and 9. For example, nucleotide identification module 1036 may cause processor 1040 to use measured values from 1031 (illustratively, in an order corresponding to the temporal order in which they were obtained), and to use at least a portion of data structure 1032 that was obtained under the same operating condition as were the measured values. For example, nucleotide identification module 1036 may cause processor 1040 to compare the identification of a measurement condition stored within measured values 1031 to the identification of a measurement condition stored within data structure 1032, and to ignore any values within data structure 1032 that do not match the measurement condition of the measured values 1031. Nucleotide identification module 1036 may cause processor 1040 to perform an operation comparing the measured values to values within the data structure, for example by taking differences between the measured values and values within the data structure, by taking ratios between the measured values and values within the data structure, by performing statistical comparisons such as the T-test, or the like. Nucleotide identification module 1036 may cause processor 1040 to select the value within data structure 1032 that, based on the comparison, is most similar to the measured value, and to select from data structure 1032 the combination of nucleotides (e.g., at least at locations 4 and 4' at the 3' end of the duplex and at locations 5 and 6 illustrated in FIG. 1F) that previously provided that measured value.

Nucleotide identification module 1036 may cause processor 1040 to use the selected combinations of nucleotides to construct an electronic sequence of nucleotides that corresponds to the physical sequence of nucleotides in unknown polynucleotide 150 to which measured values 1031 correspond. For example, using the labels illustrated in FIG. 1F, each measured value 1031 includes contributions from the base pair 4, 4', as well as the unpaired nucleotides 5 and 6. Accordingly, in some examples, nucleotide identification module 1036 may cause processor 1040 to include the nucleotides at locations 4, 5, and 6 within the electronic sequence of nucleotides that corresponds to the physical sequence of nucleotides in unknown polynucleotide 150. In this regard, at least some of such nucleotides may already have been included in the electronic sequence, because at least some of such nucleotides also would have contributed to the value measured in the immediately prior measurement step—that is, before the addition of a single nucleotide—but at a location that is shifted by a single nucleotide. As such, the electronic sequence already may include the nucleotides that now are at locations 4 and 5, but were at locations 5 and 6 in the previous measurement step. The nucleotide that is now at location 6 may be added to the electronic sequence; for example, having been at location 7 in the previous measurement step it may not have sufficiently contributed to the value in the previous measurement step in such a manner as to be identifiable during that step, but now is identifiable. Nucleotide identification module 1036 may cause processor 1040 to output the electronic sequence of nucleotides, e.g., by saving the sequence to memory 1030, electronically transmitting the sequence to another device or system (not specifically illustrated), displaying the sequence or a portion thereof on a display screen (not specifically illustrated) that is operably coupled to circuit 160, or the like.

Nucleotide identification module 1036 optionally may be configured to cause processor 1040 to identify nucleotides, or confirm the identity of nucleotides, using measurements of multiple types of values. For example, in a manner such as described with reference to FIGS. 8A-8E and 9, for any given combination of nucleotides, data structure 1032 optionally may include different values of a particular type that respectively correspond to different measurement conditions. Additionally, or alternatively, for any given combination of nucleotides, data structure 1032 optionally may include different types of measured values. Nucleotide identification module 1036 may cause processor 1040 to use any combination of values obtained using different types of measurements and/or different measurement conditions to identify nucleotides, or confirm the identity of nucleotides. As one illustrative example, nucleotide identification module 1036 may cause processor 1040 to use both a given value, and the standard deviation of that or a different value, to identify a point in data structure 1032 corresponding to a particular combination of duplex base pairs and unpaired nucleotides. As another illustrative example, nucleotide identification module 1036 may cause processor 1040 to use values from two other different types of measurements to identify a point in data structure 1032 corresponding to a particular combination of duplex base pairs and unpaired nucleotides.

In some examples, nucleotide identification module 1036 additionally, or alternatively, may be configured to cause processor 1040 to confirm the accuracy of an identification using at least the immediately previous or next measurement step, if not even earlier and/or even later measurement step(s). For example, in a manner such as described with reference to FIGS. 8A-8E, if for a given measurement step processor 1040 identifies nucleotides A, C, and G at locations 4, 5 and 6, and if such identification is accurate, then for the next measurement step (after addition of a single nucleotide using nucleotide addition module 1034) the processor should identify nucleotides C and G at locations 4 and

5. On the other hand, if either the current or previous identification is inaccurate, then one or both of the nucleotides at locations 4 and 5 in one measurement step may not match the nucleotides at locations 5 and 6 in the immediately previous measurement step. So as to enhance accuracy of the electronic sequence obtained, nucleotide identification module 1036 may cause processor 1040 to compare the nucleotides identified for a given measurement step to the nucleotides identified for at least one other (e.g., earlier or later step) measurement step, and to indicate (e.g., flag) an error based on any differences between identified nucleotides that should have been the same as each other.

Responsive to an indication of a nucleotide identification error, nucleotide identification module 1036 may cause processor 1040 to take one or more remedial actions. For example, nucleotide identification module 1036 may cause processor 1040 to disregard one or more nucleotide identifications that are in error, e.g., by replacing the erroneous identification with an identification that is known to be correct from other measurement steps that are consistent with each other (e.g., because each given nucleotide may contribute to three or more sequential measurement values); or by indicating the nucleotide as not being identified (e.g., using a nonce character such as "X" to indicate that the nucleotide's identity is unknown). As another example, which may be implemented in addition to or as an alternative to another remedial action, nucleotide identification module 1036 may cause processor 1040 to attempt to identify the nucleotide again using stored measured values 1031 and data structure 1032. As another example, which may be implemented in addition to or as an alternative to another remedial action, nucleotide identification module 1036 may cause processor 1040 to attempt to identify the nucleotide again by obtaining a new measured value 1031 using a different measurement condition (e.g., a modified first force F1') and data structure 1032. As another example, which may be implemented in addition to or as an alternative to another remedial action, nucleotide identification module 1036 may cause processor 1040 to attempt to identify the nucleotide again by obtaining a new measured value 1031 using a different measurement type (e.g., a standard deviation of the first used measurement type) and data structure 1032; in this regard, note that a separate measurement step need not necessarily be performed, e.g., because the standard deviation may be obtained from the stored measured values 1031. As another example, which may be implemented in addition to or as an alternative to another remedial action, nucleotide identification module 1036 may cause processor 1040 to resequence the unknown polynucleotide 150 in a manner such as described elsewhere herein. As another example, which may be implemented as an alternative to such remedial measure(s), or may be implemented if such remedial measure(s) are attempted but do not succeed, nucleotide identification module 1036 may cause processor 1040 to indicate in the electronic sequence that the nucleotide was not identified (e.g., using a nonce character such as "X" to indicate that the nucleotide's identity is unknown). In some examples, nucleotide identification module 1036 may cause processor 1040 to select from among these or other operations based upon the apparent nature of the error and the options available at the time the error is identified.

Note that in some examples, data structure 1032 and nucleotide identification module 1036 suitably may be implemented using machine learning. For example, data structure 1032 may be generated by training any suitable machine learning algorithm, such as a neural network (e.g., deep learning algorithm) using measured values, the combinations of nucleotides where are known a priori to correspond to those measured values, and the measurement conditions under which those measured values were obtained. In this regard, data structure 1032 may have a construction that is readily usable by the trained machine learning algorithm, e.g., trained neural network, such as a trained deep learning algorithm (nucleotide identification module 1036, implemented by processor 1040) to identify combinations of nucleotides using measured values, but such construction may not necessarily be usable by any other software, module, or algorithm to determine correlations between measured values and unknown combinations of nucleotides. For example, machine learning algorithms (such as neural networks, e.g., deep learning algorithms) may be trained, using the signal output of circuitry 160, to make base calls. Non-limiting examples of machine learning algorithms are supervised, semi-supervised, unsupervised, and reinforcement algorithms. Neural network algorithms are a subset of machine learning algorithms and may include deep learning algorithms, convolutional neural networks, recurrent neural networks, generative adversarial networks, and recursive neural networks. Accordingly, the particular construction of data structure 1032 may include, for example, a vector space, graph space, neurons of a neural network, or the like. Alternatively, data structure 1032 may be implemented using any suitable data structure that may be queried using nucleotide identification module, such as a look-up table (LUT), matrix, flat-file database structure, SQL database structure, or the like. Nucleotide identification module 1036 may cause processor 1040 to suitably identify points in the data structure 1032 with measured values, for known combinations of nucleotides, that correspond to the measured values for unknown combinations of nucleotides.

It should be appreciated that circuitry 160 may be implemented using any suitable combination of digital electronic circuitry, integrated circuitry, application specific integrated circuits (ASICs), field programmable gate arrays (FPGAs), central processing units (CPUs), graphical processing units (GPUs), computer hardware, firmware, software, and/or combinations thereof. For example, one or more functionalities of circuit 160 may be implemented in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to as modules, programs, software, software applications, applications, components, or code, can include machine instructions for a programmable processor, and/or can be implemented in a high-level procedural language, an object-oriented programming language, a functional programming language, a logical programming language, and/or in assembly/machine language. As used herein, the terms "memory" and "computer-readable medium" refer to any computer program product, apparatus and/or device, such as magnetic discs, optical disks, solid-state storage devices, memory, and Programmable Logic Devices (PLDs), used to provide machine instructions and/or data to a programmable data processor, including a machine-readable medium that receives machine instructions as a computer-readable signal. The term "computer-readable signal" refers to any signal used to provide machine instructions and/or data to a programmable data processor. The computer-readable medium can store such machine instructions non-transitorily, such as would a non-transient solid-state memory or a magnetic hard drive or any equivalent storage medium. The computer-readable medium can alternatively or additionally store such machine instructions in a transient manner, such as for example as would a processor cache or other random-access memory associated with one or more physical processor cores.

The computer components, software modules, functions, data stores and data structures described herein can be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality can be located on a single computer or distributed across multiple computers and/or the cloud, depending upon the situation at hand.

In one nonlimiting example, circuit 160 described with reference to FIG. 10 may be implemented using a computing device architecture. In such architecture, a bus (not specifically illustrated) can serve as the information highway interconnecting the other illustrated components of the hardware. The system bus can also include at least one communication port (such as a network interface) to allow for communication with external devices either physically connected to the computing system or available externally through a wired or wireless network. Processor 1040 may be implemented using a CPU (central processing unit) (e.g., one or more computer processors/data processors at a given computer or at multiple computers) that can perform calculations and logic operations required to execute a program. Memory 1030 may include a non-transitory processor-readable storage medium, such as read only memory (ROM) and/or random access memory (RAM) in communication with processor 1040 and can include one or more programming instructions for the operations provided herein, e.g., sequencing module 1033 and its components, and may store measured values 1031 and data structure 1032. Optionally, memory 1030 may include a magnetic disk, optical disk, recordable memory device, flash memory, or other physical storage medium. To provide for interaction with a user, circuit 160 may include or may be implemented on a computing device having a display device (e.g., a CRT (cathode ray tube) or LCD (liquid crystal display) monitor) for displaying information obtained to the user and an input device such as keyboard and/or a pointing device (e.g., a mouse or a trackball) and/or a touchscreen by which the user can provide input to the computer.

Note that sequencing module 1033 further may be configured to cause processor 1040 to perform additional operations such as will be described with reference to FIGS. 2A-2E, 3, 4A-4C, 5A-5B, and 6. Such operations may be implemented using additional modules not specifically illustrated in FIG. 10, or may be implemented using suitable modifications to nucleotide addition module 1034, measurement module 1035, and/or nucleotide addition module 1036.

The system, compositions, and operations described with reference to FIGS. 1A-1H suitably may be modified so as to further enhance accuracy of the measurements made. For example, FIGS. 2A-2E schematically illustrate use of an example sequencing system, and additional example compositions and operations, for sequencing a polynucleotide using a nanopore. System 200, which will now be described with reference to FIGS. 2A-2E, may be configured and used similarly as system 100 described with reference to FIGS. 1A-1H. For example, system 200 similarly may include first and second electrodes 102, 103, barrier 101 optionally including first and second layers 107, 108, nanopore 110, polynucleotides 140, 150, polymerases 105, nucleotides 121, 122, 123, 124, and circuitry 160, each of which may be configured similarly as described with reference to FIGS. 1A-1H. However, duplex 254 may be modified relative to duplex 154, in that a blocking moiety 234 may be reversibly associated with the duplex and may reversibly inhibit polymerase 105 from adding a second nucleotide. For example, at the particular time illustrated in FIG. 2A, circuitry 160 may apply the second force F2 such that polymerase 105 may add nucleotide 122 to 3' end 253 in a similar manner as described with reference to FIG. 1B. Blocking moiety 234 may inhibit polymerase 105 in fluid 220 from adding another nucleotide to 3' end 253 until blocking moiety 234 is intentionally removed. In some examples, blocking moiety 234 may include a 3'-blocking group that is coupled to respective nucleotides 121, 122, 123, 124 in fluid 220.

Figure 2A:
FIGS. 2A-2E schematically illustrate use of an example sequencing system, and additional example compositions and operations, for sequencing a polynucleotide using a nanopore.
Figure 2B:
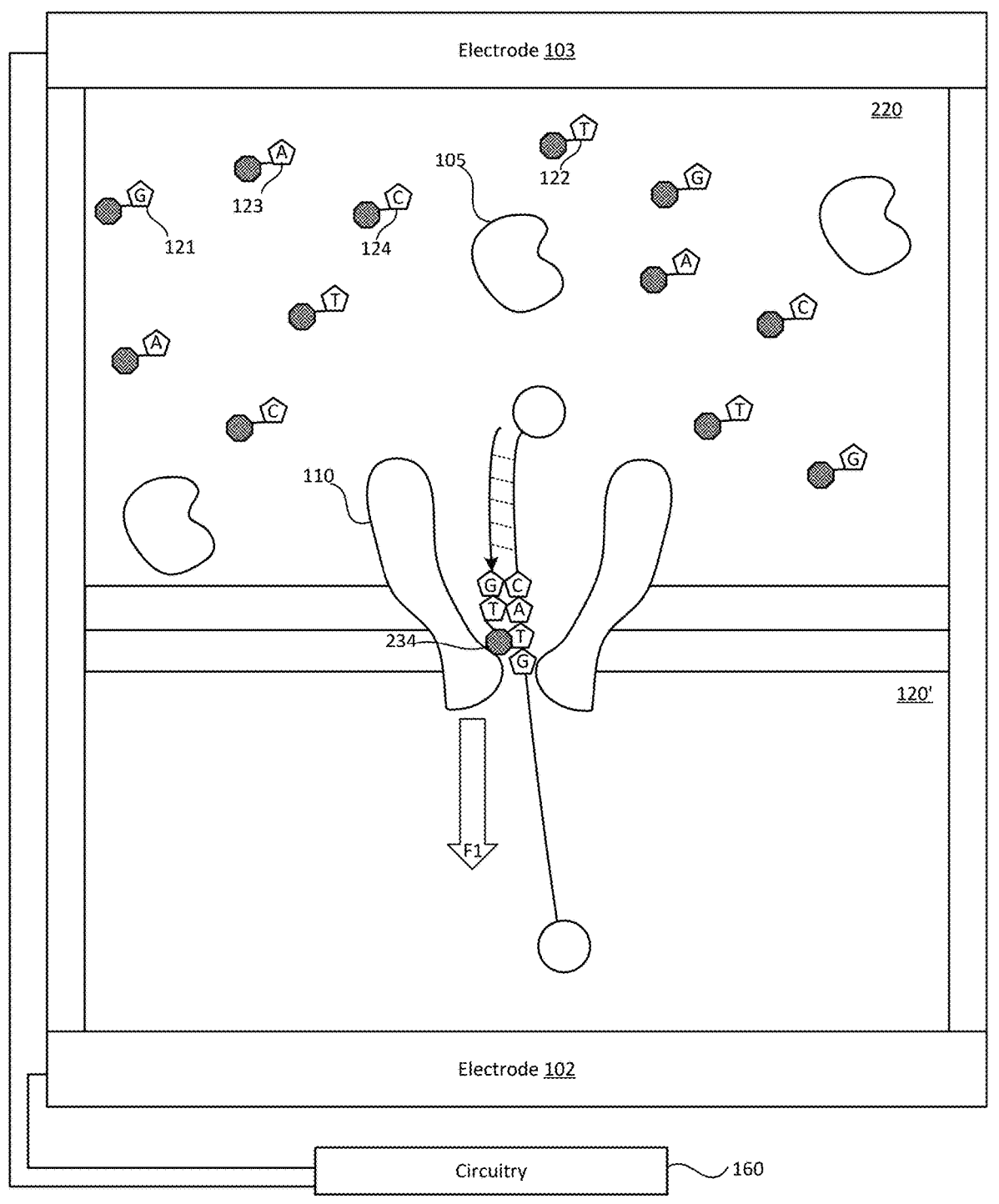
Figure 2C:
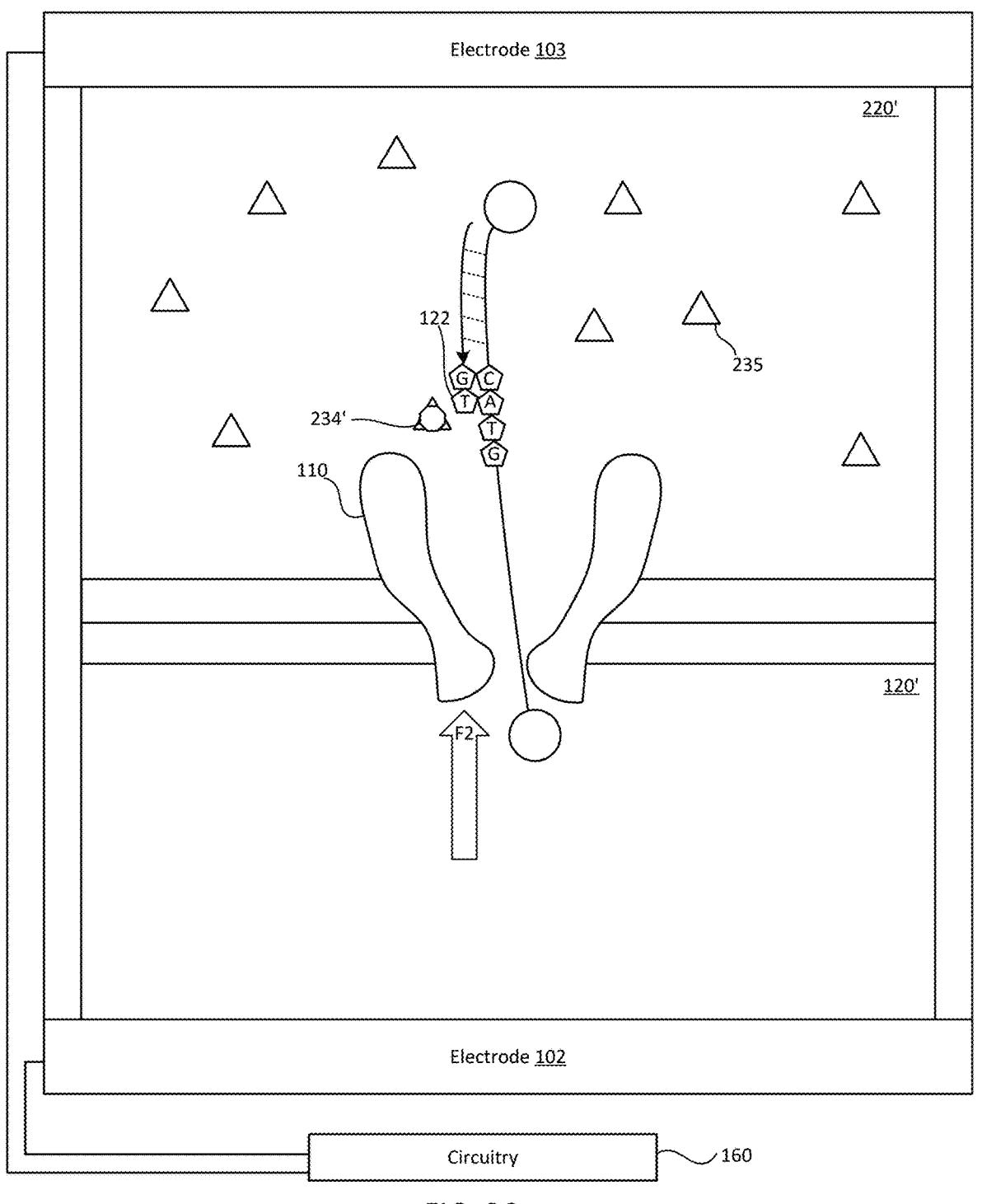

Circuitry 160 may be configured to detect association of blocking moiety 234 with duplex 254. For example, as illustrated in FIG. 2B, while applying the first force F1, circuitry also may measure a value of an electrical property in a manner similar to that described with reference to FIGS. 1A, 1C, and 1E. In a similar manner as discussed with reference to FIGS. 1A, 1F, 1G, and 1H, the particular base pair at 3' end 253 of duplex 254 (e.g., TA), the sequence of one or more bases in single-stranded second portion 156 (e.g., T,G), in combination with the presence of blocking moiety 234, may alter the rate at which salt in fluid 120 moves through aperture 113 and into fluid 120' under the particular measurement conditions used, and thus may alter the electrical current, ionic current, electrical resistance (resistance to ion flow), or electrical voltage drop across nanopore 110, or the standard deviation of any such electrical characteristics, in such a manner as to be detected by circuitry 160. Accordingly, circuitry 160 may use the value measured to detect the presence of blocking moiety 234, and also may identify at least one nucleotide in the polynucleotide 150 using the value measured. Additionally, or alternatively, circuitry 160 may detect absence of blocking moiety 234 from the duplex 254. For example, if blocking moiety 234 is not present, then its absence may alter the rate at which salt in fluid 120 moves through aperture 113 and into fluid 120' as compared to the rate in the presence of blocking moiety 234, and thus may alter the electrical current, ionic current, electrical resistance (resistance to ion flow), or electrical voltage drop across nanopore 110, or the standard deviation of any such electrical characteristics, in such a manner as to be detected by circuitry 160. In this regard, note that additional dimension(s) of data structure 1032 further may include measured values corresponding to the presence of blocking moiety 234 coupled to the nucleotide at the 3' end 253 of duplex 254.

Figure 2D:
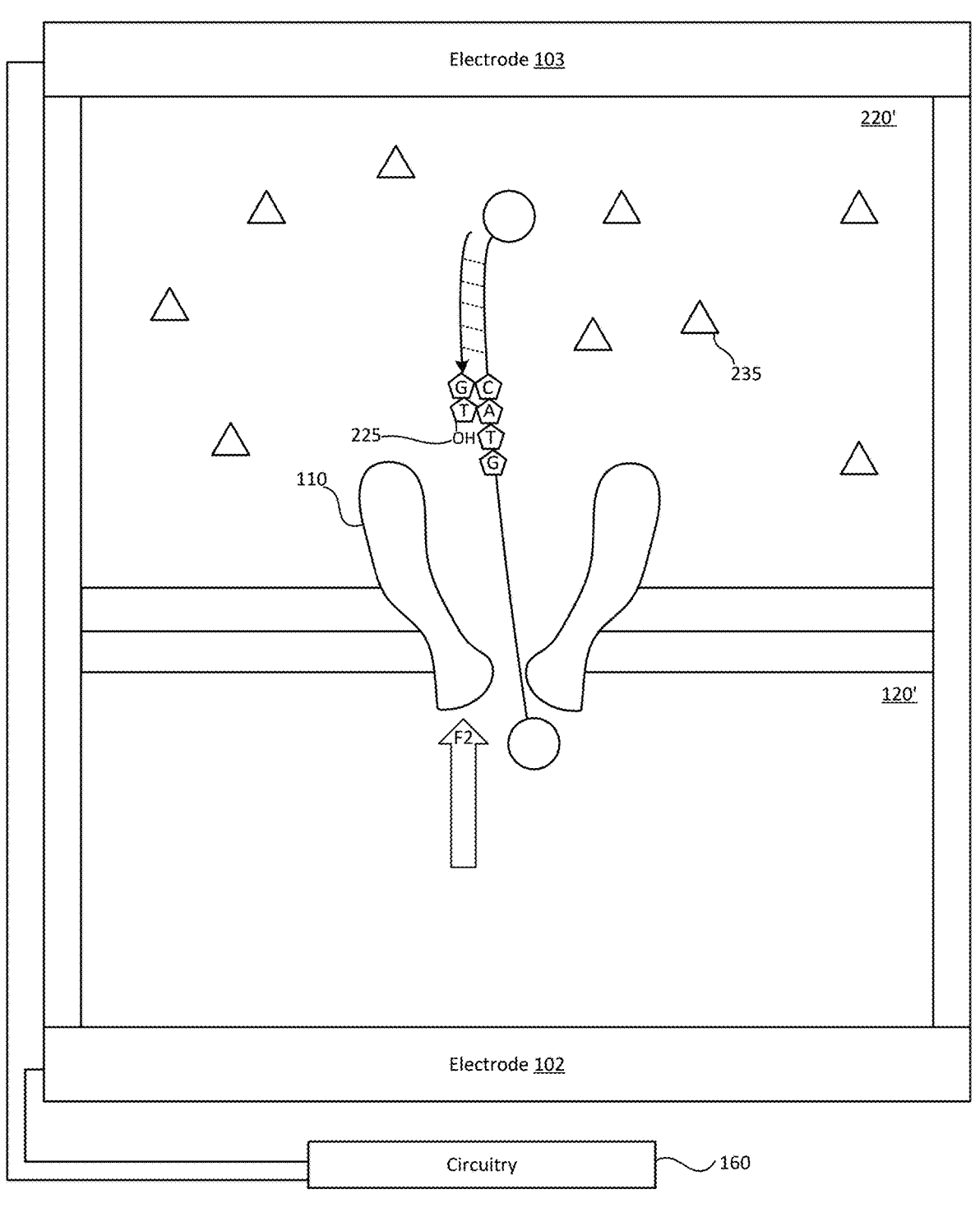
Figure 2E:
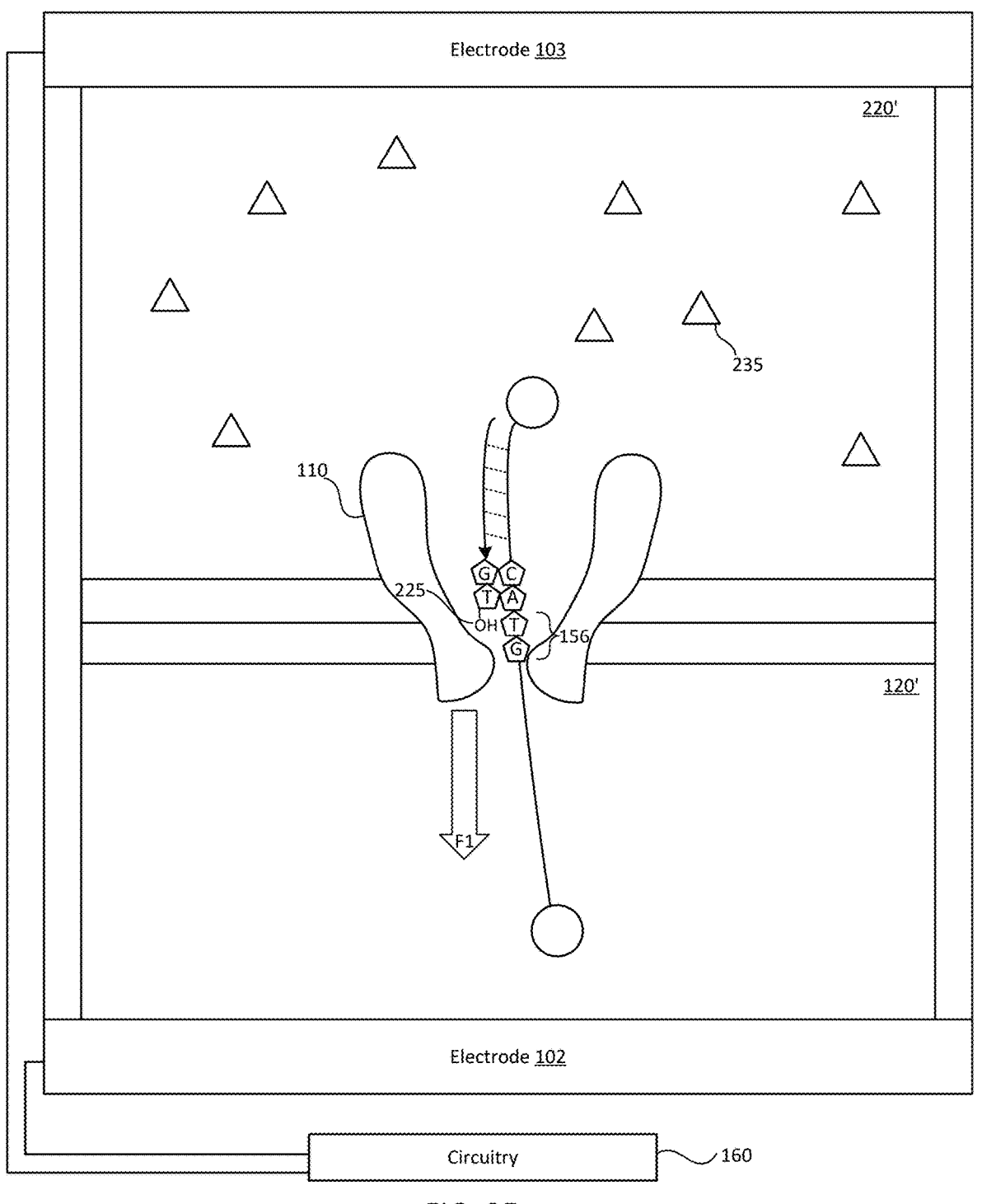

The blocking moiety 234 may be alterable or removable in such a manner as to allow polymerase 105 to add a second nucleotide, for example after presence of the blocking moiety has been confirmed using operations such as described with reference to FIG. 2B. In the nonlimiting example illustrated in FIG. 2C, the fluid 220 is replaced with a fluid that does not contain polymerase and does not contain blocked nucleotides, and circuitry 160 applies a second force F2 so that 3' end 253 becomes accessible to modified fluid 220' which includes reactant 235 which may alter or remove blocking moiety 234, for example yielding modified blocking moiety 234' which may no longer be associated with 3' end 253. Illustratively, in examples where blocking moiety 234 includes a 3'-blocking group, removal of the blocking moiety 234 from nucleotide 221 may including replacing the blocking moiety with another chemical moiety, such as an —OH group 225 as illustrated in FIG. 2D. After blocking moiety 234 is removed, circuitry 160 again may apply the first force F1 disposing 3' end 253 of duplex 254 (which is now not associated with blocking moiety 234, and thus may correspond to 3' end 153 of duplex 154) within aperture 112 and the single-stranded second portion 156 of polynucleotide 150 within the aperture in a manner such as illustrated in FIG. 2E. While the circuitry 160 again applies first force F1, constriction 114 again may inhibit passage of 3' end 253 of duplex 254 to second side 112 of nanopore 110, and the circuitry may measure the value of the electrical property of the nanopore, confirming that the blocking moiety has been removed. Fluid 220' optionally may then be replaced with another fluid, e.g., a fluid that does not cause the block to be removed. Whether or not fluid 220' is replaced at this time, because blocking moiety 234 is not present at the 3' end 253 of duplex 254, then the absence of the blocking moiety alters the rate at which salt in fluid 120 moves through aperture 113 and into fluid 120' as compared to the rate in the presence of blocking moiety 234, and thus may alter the electrical current, ionic current, electrical resistance, or electrical voltage drop across nanopore 110, and/or the standard deviation of any such electrical characterization, in such a manner as to be detected by circuitry 160. Nucleotide 122 thus may be identified using the value measured, e.g., in a manner such as described with reference to FIGS. 1A, 1C, 1E, 8A-8E, 9, and 10. Fluid 220' may be replaced with fluid 220 that contains polymerase and blocked nucleotides so as to repeat the process of adding a blocked nucleotide to the end of the duplex 254 (FIG. 2A), generating a signal using the blocked nucleotide at the end of the duplex (FIG. 2B), removing the blocking group 234 (FIGS. 2C-2D), and generating a signal using the deblocked nucleotide at the end of the duplex (FIG. 2E). Such operations may be repeated any suitable number of times, e.g., so as to sequence at least a portion of polynucleotide 150, e.g., identifying the added nucleotides using the signals in a manner such as described elsewhere herein.

Accordingly, it will be appreciated that measurements such as described with reference to FIG. 2B may be used to confirm that a blocked nucleotide has been incorporated. Because the blocking moiety inhibits the duplex 254 from being extended by any additional nucleotides until the blocking moiety 234 is removed (FIG. 2C), deletion errors are inhibited that otherwise may have occurred due to uncontrolled and unobserved addition of multiple nucleotides. Measurements such as described with reference to FIG. 2E may be used to confirm that the nucleotide was properly deblocked, in addition to identifying the nucleotide. It will be appreciated that the ability to perform such repeated measurements in an electronically controlled, stepwise manner may provide for remarkable enhancements in accuracy as compared, for example, to the enzyme-driven translocation used in strand sequencing.

In one illustrative example, second force F2 is used to eject the 3' end 253 of duplex 254 from nanopore 110 into fluid 220 (FIG. 2A), and a suitable time window (e.g., about 1-50 ms) is provided for the polymerase to add a nucleotide.

There is a probability during this time window that a blocked nucleotide would have been added. It may be useful to confirm whether this blocked nucleotide indeed was added, for example in circumstances in which the nucleotide combination otherwise may be difficult to identify. For example, a relatively long homopolymer region is being sequenced in which subsequent nucleotide combinations yield similar measured signals as one another. Or, for example, nucleotide identification module 1036 may determine that the measured value for the unknown combination is too similar to multiple ones of the measured values within data structure 1032. Information confirming that a blocked nucleotide was added may provide a useful aid to nucleotide identification module 1036 in treating the signal properly. For example, responsive to confirmation of the presence of a blocked nucleotide at the 3' end 253 of duplex 254, nucleotide identification module 1036 may cause processor 1040 to include the nucleotide in the electronic sequence, even if it is flagged as having a low quality base call or as not being identified. Or, for example, nucleotide identification module 1036 may cause processor 1040 to implement any other suitable remedial measure, such as repeating the measurement using a modified first force F1'. Or, for example, responsive to determining that the nucleotide at the 3' end 253 of duplex 254 did not include blocking moiety 234, nucleotide identification module 1036 may cause processor 1040 to assume that the polymerase did not add a nucleotide, and therefore to again eject the 3' end of duplex 254, and to wait again for the time window during which a polymerase may add a blocked nucleotide. Accordingly, measurements indicating that the blocking moiety 234 is not present at the 3' end of the duplex after the time window usefully may be interpreted as meaning that the polymerase did not act upon the duplex during that time window. Responsive to such an indication, circuit 160 may repeat the nucleotide addition and sequencing operations so as to attempt again to identify (or confirm the identity of) the next nucleotide in the sequence of polynucleotide 150.

It will further be appreciated that measurements and operations such as described with reference to FIGS. 2A-2E suitably may be used in conjunction with measurements such as described with reference to FIG. 1D, e.g., to additionally confirm that a polymerase is acting at the appropriate time upon the 3' end of the duplex. In this regard, the measurement described with reference to FIG. 1D further may be used to detect the blocking moiety coupled to a nucleotide upon which the polymerase is acting.

In examples such as described with reference to FIGS. 2A-2E, nucleotides 121, 122, 123, 124 may be coupled to any suitable blocking moiety 234, and any suitable reactant 235 may be used to deblock the nucleotide at the 3' end 253 of duplex 254 (remove the blocking moiety). In one non-limiting example, blocking moiety 234 includes an azido methyl (AZM) group (—OCH$_2$N$_3$), which may be expected to alter the current flow through nanopore 110 when present at the 3' end of the duplex 254, and which may be removed using tris(2-carboxyethyl)phosphine (TCEP) or tris(hydroxypropyl)phosphine (THP) to leave a 3' OH group that can be extended by another blocked nucleotide using a polymerase. A variety of other blocking moieties, and reactants for removing such blocking moieties, are known in the art and suitably may be adapted for use with the present subject matter. See, e.g., U.S. Patent Publication No. 2020/0216891 to Francais et al., the entire contents of which are incorporated by reference herein.

While FIGS. 2A-2E illustrate an example in which the reactant 235 is located in a fluid on the first side 111 of nanopore 110 so as to remove blocking moiety 234 while the 3' end 253 of the duplex 254 is ejected from nanopore 110, the reactant instead may be located in such a manner as to remove the blocking moiety while 3' end of the duplex is within the nanopore. As such, the presence of the blocking moiety may be measured in a manner similar to that described with reference to FIGS. 2A-2E, and also the removal of the blocking moiety may be observed in real-time. For example, if the presence of the blocking moiety affects the measured value, then as the moiety is removed a change in the measured value may be expected. Confirming removal of the blocking moiety via such a change is useful information, because if the moiety was not removed (as reflected by the measured value not changing), then when the duplex is ejected from the nanopore (which may happen on a clock whether the moiety was removed or not), then circuitry 160 may determine that the next "incorporation" should be ignored because it was not actually an incorporation from a new cycle.

Note that the need for fluidic cycling (the exchange of one fluid with another between certain operations) may be reduced in examples such as described with reference to 1A-1H, as compared to examples such as described with reference to FIGS. 2A-2E. For example, in order to dissociate blocking moiety 234 from nucleotide 122 during the operation described with reference FIG. 2C, fluid 220 including nucleotides and polymerase may be removed (e.g., by flushing with an aqueous solvent) and then replaced with fluid 220' including reagent 235. Later, in order to add another nucleotide to deblocked nucleotide 122, fluid 220' may be removed (e.g., by flushing with an aqueous solvent) and then replaced with fluid 220. In the examples described with reference to FIGS. 2A-2E, multiple fluidic cycles are used because nucleotide deblock and nucleotide addition steps occur within the same compartment (on the same, first side 111 of the nanopore), and direct contact between the nucleotide deblock and nucleotide addition components in that compartment may cause premature deblocking of the nucleotides (e.g., prior to addition), which may result in reduced control of the nucleotide addition process. In comparison, throughout the nucleotide addition steps described with reference to FIGS. 1A-1H, polymerase 105 may run freely without the need for fluidic cycling. For example, FIGS. 1A-1H obviate the need for addition and removal of deblocking agent, because the polymerase may freely add nucleotides from fluid 120 to the 3' end 153 of duplex, and such nucleotides may be distinguished from one another in a manner such as described with reference to 8A-8E, 9, and 10 and the Working Examples provided further below.

It will further be appreciated that any suitable combination of operations such as described with reference to FIGS. 1A-1H, 2A-2E, 7, 8A-8E, 9, and 10 may be used to sequence a polynucleotide, e.g., polynucleotide 150. For example, FIG. 3 illustrates a flow of operations in an example method for sequencing a polynucleotide. Method 300 may use a nanopore that includes a first side, a second side, and an aperture extending through the first and second sides, e.g., in a manner such as described with reference to FIGS. 1A-1H and FIG. 7. Method 300 may include disposing the polynucleotide through the aperture of the nanopore such that a 3' end of the polynucleotide is on the first side of the nanopore, and a 5' end of the polynucleotide is on the second side of the nanopore (operation 310). Example operations for disposing polynucleotide 150 through the aperture of nanopore 110 in such a manner are provided below with reference to FIG. 6. Method 300 may include forming a duplex with the polynucleotide on the first side of the nanopore, the duplex including a 3' end (operation 320).

Figure 6:
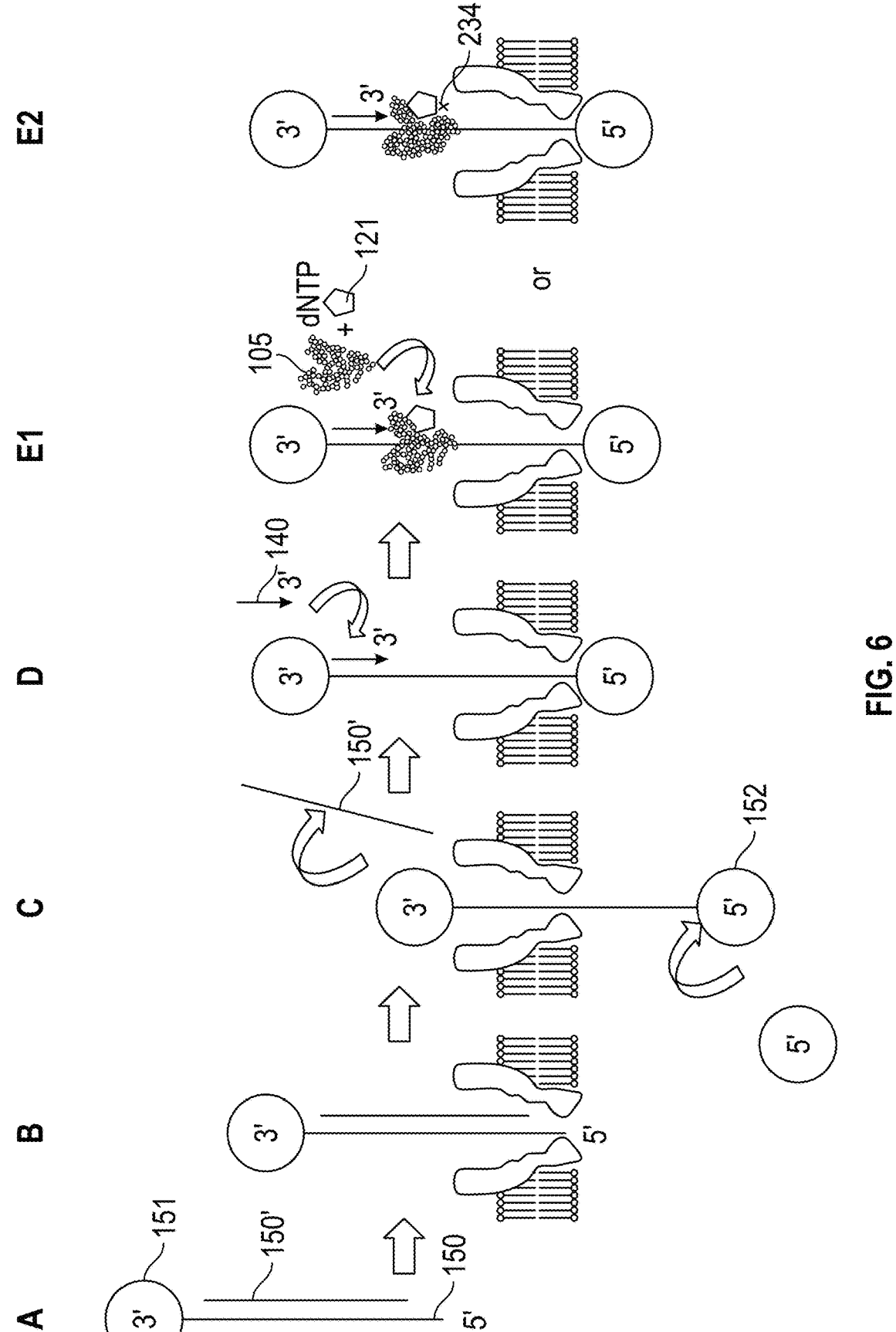
FIG. 6 (SEQ ID NO: 5, SEQ ID NO: 6) schematically illustrates use of the sequencing system of FIGS. 1A-1H to generate and use a polynucleotide for sequencing or polynucleotide synthesis.

Such a duplex may be formed, for example, by hybridizing the first portion 155 of nucleotide 150 to a primer (polynucleotide 140 or a portion thereof) on the first side of the nanopore, e.g., in a manner such as described below with reference to FIG. 6.

Method 300 may include extending the duplex on the first side of the nanopore by adding a nucleotide to the 3' end of the duplex (operation 330). For example, circuitry 160 may apply second force F2, responsive to which the 3' end of the duplex is located out of the aperture of the nanopore such that a polymerase may act upon the 3' end of the duplex to add a nucleotide thereto, e.g., in a manner such as described with reference to FIGS. 1B, 1D, and 2A. Method 300 may include applying a first force disposing the 3' end of the duplex within the aperture (operation 340). For example, circuitry 160 may apply a first force F1 in a manner such as described with reference to FIGS. 1A, 1C, 1E, 2B, and 2E. Operation 340 of method 300 may include, while applying the first force, inhibiting, using the nanopore, translocation of the 3' end of the extended duplex to the second side of the nanopore (operation 341). For example, constriction 114 or other feature of nanopore 110 may inhibit passage of 3' end 153 of duplex 154, or passage of 3' end 253 of duplex 254, from the first side 111 of nanopore 110 to the second side 112 of nanopore 110 in a manner such as described with reference to FIGS. 1A, 1C, 1E, 2B, and 2E. Operation 340 of method 300 also may include, while applying the first force, measuring a value of an electrical property of the 3' end of the duplex and a single-stranded portion of the polynucleotide (operation 342). For example, circuitry 160 may measure such a value of the electrical property in a manner such as described with reference to FIGS. 1A, 1C, 1E, 2B, and 2E. Method 300 may include identifying the nucleotide which had been added using the value measured in operation 340 (operation 350). For example, circuitry 160 may identify one or more nucleotides in the polynucleotide 150 in a manner such as described with reference to FIGS. 8A-8E, 9, and 10. As shown in FIG. 3, operations 330-350 may be repeated any suitable number of times, e.g., so as to substantially sequence polynucleotide 150.

Note that operations such as described with reference to method 300 are compatible with, and may be used in conjunction with, any other operations such as provided herein. For example, the nucleotides that are added optionally may include respective blocking moieties, and such blocking moieties optionally may be removed, in a manner such as described with reference to FIGS. 2A-2E.

Figure 4A:
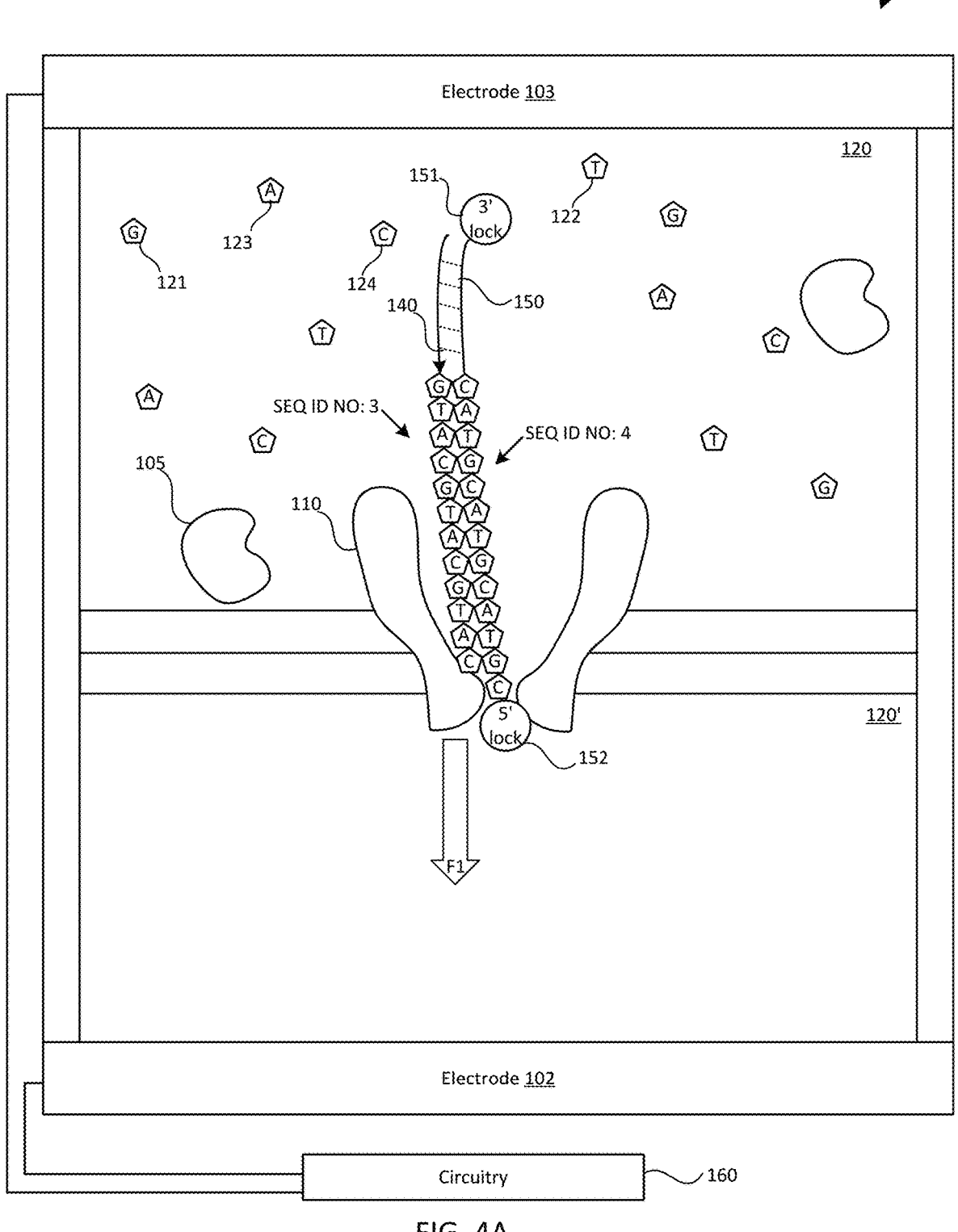
FIGS. 4A-4C (SEQ ID NO: 3, SEQ ID NO: 4) schematically illustrate use of the sequencing system of FIGS. 1A-1H to re-sequence the same polynucleotide.
Figure 4B:
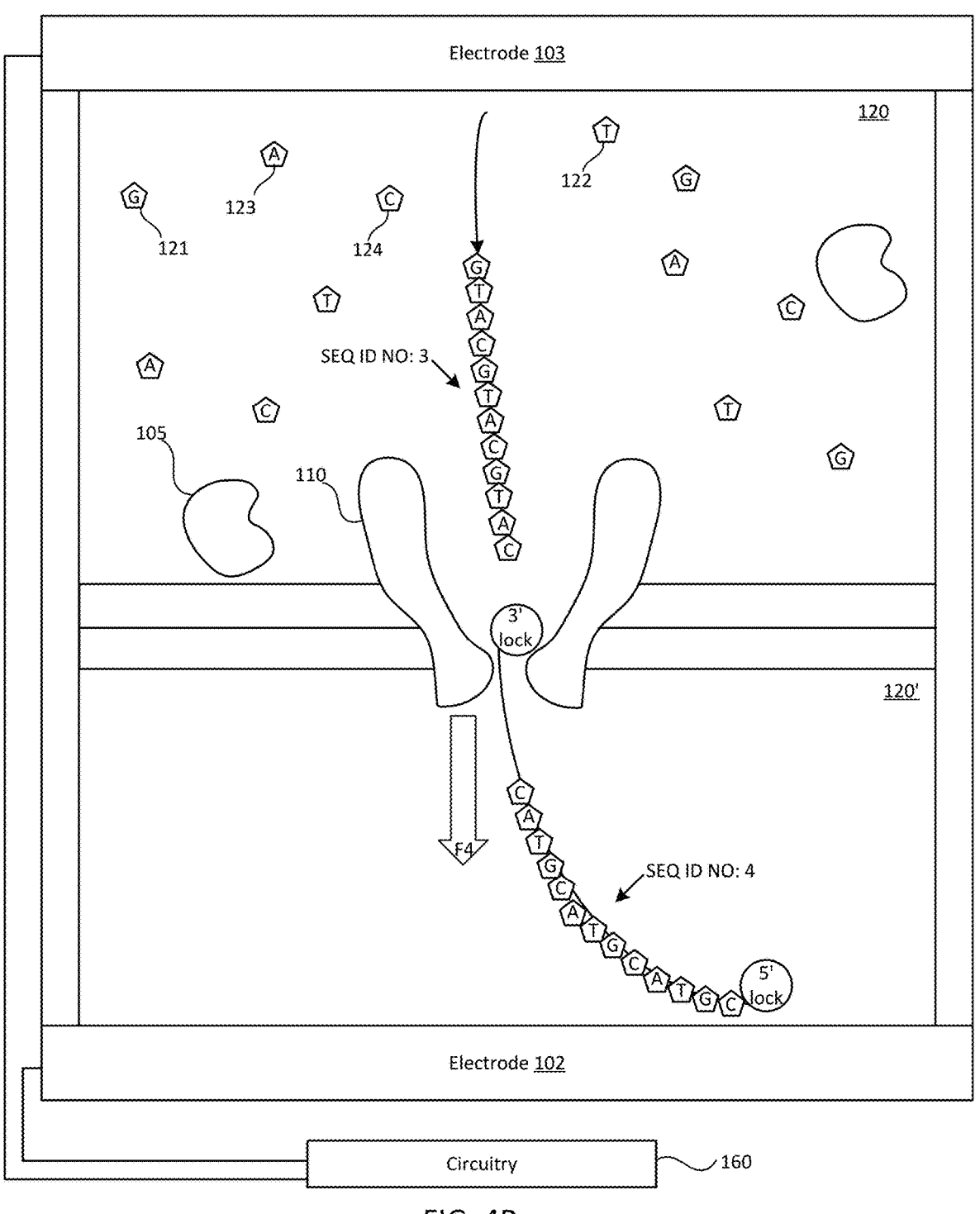
Figure 4C:
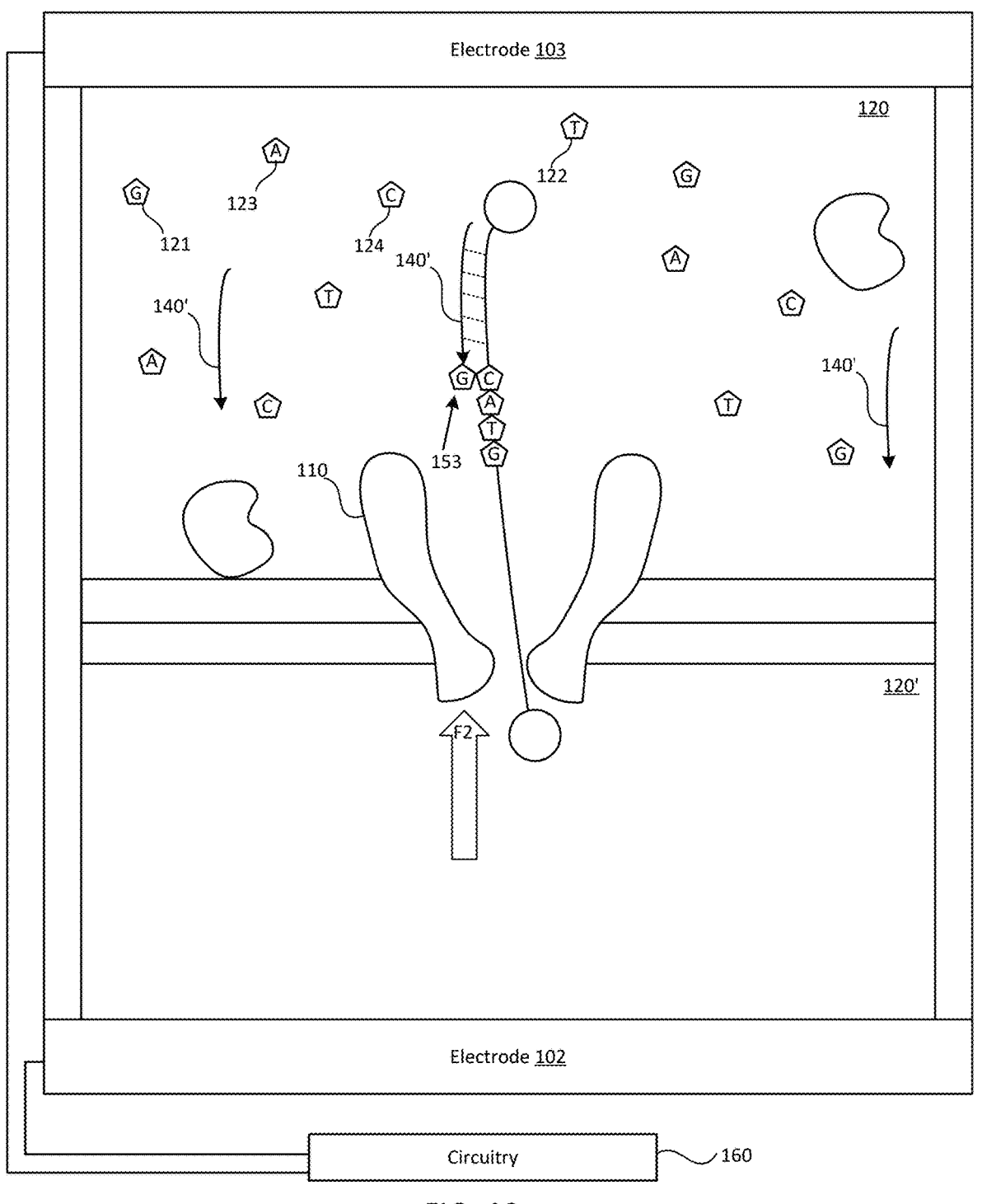

It will further be appreciated that the same nanopore may be used in multiple different sequences of operations such as described with reference to FIGS. 1A-1H, 2A-2E, 3, 7, 8A-8E, 9, and 10, which sequences of operations may use the same polynucleotides 150 as one another or may use different polynucleotides 150 than one another. For example, FIGS. 4A-4C schematically illustrate use of the sequencing system of FIGS. 1A-1H to re-sequence the same polynucleotide 150, e.g., to generate a consensus read. Referring now to FIG. 4A, system 100 is shown at a time at which sequencing of polynucleotide 150 is substantially complete; alternatively, the sequencing of polynucleotide 150 may be partially completed and nucleotide identification module 1042 has caused processor 1040 to take the remedial action of resequencing polynucleotide 150. Responsive to circuitry 160 applying the first force F1 as shown in FIG. 4A, polynucleotide 150 remains hybridized to the (now-extended) polynucleotide 140 in a manner such as described elsewhere herein. To resequence polynucleotide 150, circuitry may be configured to apply a sufficiently high voltage F4 to dissociate duplex 154 or to dissociate duplex 254, that is, to dehybridize extended polynucleotide 140 from polynucleotide 150 in a manner such as illustrated in FIG. 4B. Polynucleotide 150 optionally may be re-sequenced, e.g., using operations that include hybridizing a new (shorter) polynucleotide 140', such as a primer, to polynucleotide 150 in a manner such as illustrated in FIG. 4C. For example, primers 140' may be included in fluid 120. The sequence of nucleotide addition and measurement operations provided herein then may be used to partially or fully sequence polynucleotide 150 again. As such, the new duplex formed on the first side of the nanopore may include the same first portion 155 of polynucleotide 150 as described with reference to FIG. 1A, and may have another 3' end 153 that includes the end of the new polynucleotide 140'. Such sequence of operations described with reference to FIGS. 4A-4C may be repeated any desired number of times to sequence polynucleotide 150 over and over, e.g., until a desired level of accuracy is achieved to provide desired confidence in the sequence. For example, accuracy is improved by combining multiple reads of the same template when errors are random and those can be "averaged out" through the use of consensus algorithms known in the art.

Figure 5A:
FIGS. 5A-5B (SEQ ID NO: 3, SEQ ID NO: 4) schematically illustrate use of the sequencing system of FIGS. 1A-1H to prepare the nanopore for sequencing a different polynucleotide.
Figure 5B:
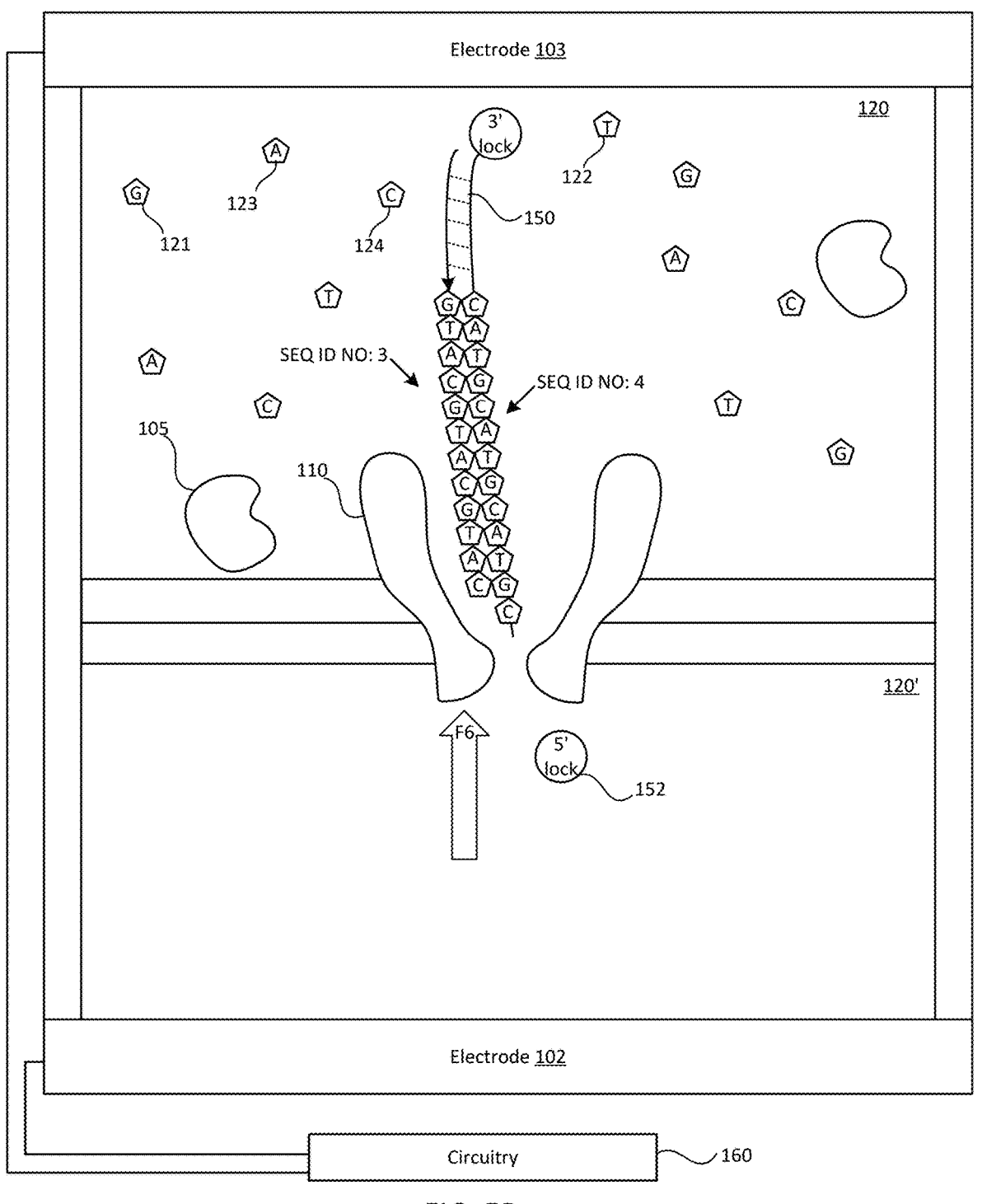

After fully or partially sequencing polynucleotide 150 any desired number of time(s), or alternatively after sequencing polynucleotide 150 a single time or even just partially sequencing polynucleotide 150, circuitry 160 optionally may eject polynucleotide 150 from contact with nanopore 110 so that nanopore 110 may be used again with a different polynucleotide. For example, FIGS. 5A-5B schematically illustrate use of the sequencing system of FIGS. 1A-1G to prepare the nanopore for sequencing a different polynucleotide. In a manner such as illustrated in FIG. 5A, circuit 160 may be configured to apply a sufficiently high force F5 (which may be greater than force F4) to cause first steric lock 151 to dissociate from polynucleotide 150. Alternatively, in a manner such as illustrated in FIG. 5B, circuit 160 may be configured to apply a sufficiently high force F6 to cause second steric lock 152 to dissociate from polynucleotide 150. The nanopore then may be recycled, e.g., by disposing a different polynucleotide 150 therethrough that may be sequenced (and optionally re-sequenced) in a manner such as provided herein.

Polynucleotide 150 may be disposed within, and optionally locked to, nanopore 110 using any suitable structure(s) and any suitable combination of operations. For example, FIG. 6 schematically illustrates use of the sequencing system of FIGS. 1A-1H to generate and use a polynucleotide for sequencing or polynucleotide synthesis. In operation A illustrated in FIG. 6, first steric lock 151 may be coupled to the 3'-end of the polynucleotide 150, optionally while that polynucleotide is hybridized to its naturally occurring complementary strand 150'. Illustratively, the 3' end of polynucleotide 150 may be biotinylated or otherwise functionalized, and first steric lock 151 may include a functional group (such as neutravidin or streptavidin) that will bind to the functionalized (e.g., biotinylated) 3' end of polynucleotide 150 and remain bound there until a sufficiently strong force is applied in a manner such as described with reference to FIG. 5A. In other examples, first steric lock 151 may include LNA or PNA that hybridizes to polynucleotide 150 and is of sufficient length to remain hybridized to polynucleotide 150 until a sufficiently strong force is applied in a manner such as described with reference to FIG. 5A. In operation B illustrated in FIG. 6, first side 111 of nanopore 110 may be contacted with the duplex 150, 150'. In operation C illustrated in FIG. 6, circuitry 160 applies a force sufficient to cause dissociation of complementary strand 150' from polynucleotide 150 while the 5' end of strand 150 is translocated through nanopore 110. During application of such force, first steric lock 151 may inhibit passage of the 3'-end of polynucleotide 150 to the second side of the nanopore through the aperture in a manner such as described with reference to FIGS. 1A-1E. Second steric lock 152 then may be coupled to the 5' end of polynucleotide 150. Illustratively, second steric lock 152 may include LNA or PNA that hybridizes to polynucleotide 150 and is of sufficient length to remain hybridized to polynucleotide 150 until a sufficiently strong force is applied in a manner such as described with reference to FIG. 5B. In operation D illustrated in FIG. 6, polynucleotide 140 may be hybridized to polynucleotide 150 to form a duplex which may be used to sequence polynucleotide 150 in a manner such as described elsewhere herein. For example, in operations E1 and E2 illustrated in FIG. 6, polymerase 105 may add nucleotide 121 to polynucleotide 140 based on the sequence of polynucleotide 150; optionally, in operation E2 illustrated in FIG. 6, the nucleotide may be coupled to blocking moiety 234. Operations for identifying the nucleotide, and for adding additional nucleotides, are provided elsewhere herein. First steric lock 151 added in operation A may be removable from polynucleotide 150 in a manner such as described with reference to FIG. 5A. Second steric lock 152 added in operation C may be removable from polynucleotide 150 in a manner such as described with reference to FIG. 5B.

It will further be appreciated that systems, compositions, and operations such as described with reference to FIGS. 1A-1H, 2A-2E, 3, 4A-4C, 5A-5B, 6, 7, 8A-8E, 9, and 10 suitably may be adapted for use in various methods of synthesizing polynucleotides, including but not limited to sequencing-by-synthesis (SBS).

From the foregoing, it should be understood that the present disclosure provides that which is recited in the following clauses:

Clause 1. A method of sequencing a polynucleotide using a nanopore comprising a first side, a second side, and an aperture extending through the first and second sides is provided. The method comprises: (a) disposing a polynucleotide through the aperture of the nanopore such that a 3' end of the polynucleotide is on the first side of the nanopore, and a 5' end of the polynucleotide is on the second side of the nanopore. The method also comprises (b) forming a duplex with the polynucleotide on the first side of the nanopore, the duplex including a 3' end. The method also comprises (c) extending the duplex on the first side of the nanopore by adding a first nucleotide to the 3' end of the duplex. The method also comprises (d) applying a first force disposing the 3' end of the extended duplex within the aperture, and while applying the first force: inhibiting, using the nanopore, translocation of the 3' end of the extended duplex to the second side of the nanopore; and measuring a value of an electrical property of the 3' end of the extended duplex and a single-stranded portion of the polynucleotide. The method also comprises (e) identifying the first nucleotide using the value measured in operation (d).

Clause 2. The method of clause 1, wherein the value measured in operation (d) comprises an electrical current, ionic current, electrical resistance, or electrical voltage drop across the nanopore.

Clause 3. The method of clause 1 or clause 2, wherein the value measured in operation (d) comprises noise of an electrical current, ionic current, electrical resistance, or electrical voltage drop across the nanopore.

Clause 4. The method of clause 3, wherein the value measured in operation (d) comprises a standard deviation of the noise.

Clause 5. The method of any one of clauses 1 to 4, wherein the value measured in operation (d) is at least based on M nucleotides of the single-stranded portion of the polynucleotide and D pairs of hybridized nucleotides of the extended duplex, wherein M is greater than or equal to two, and wherein D is greater than or equal to one.

Clause 6. The method of clause 5, wherein M is greater than or equal to three.

Clause 7. The method of clause 5 or clause 6, wherein D is greater than or equal to two.

Clause 8. The method of any one of clauses 5 to 7, wherein at least one of the M nucleotides of the single-stranded portion comprises a modified base, the method comprising identifying the modified base using the value measured in operation (d).

Clause 9. The method of clause 8, wherein the modified base comprises a methylated base.

Clause 10. The method of any one of clauses 1 to 9, further comprising inhibiting addition of another nucleotide to the 3' end of the extended duplex while the first force is applied in operation (d).

Clause 11. The method of clause 10, wherein the nanopore inhibits the addition of another nucleotide.

Clause 12. The method of any one of clauses 1 to 11, wherein the nanopore is oriented so that the first side of the nanopore includes a majority of the aperture.

Clause 13. The method of any one of clauses 1 to 11, wherein the nanopore is oriented so that the second side of the nanopore includes a majority of the aperture.

Clause 14. The method of any one of clauses 1 to 13, further comprising: (f) applying a modified first force again disposing the 3' end of the extended duplex within the aperture, and while applying the modified first force: inhibiting, using the nanopore, translocation of the 3' end of the extended duplex to the second side of the nanopore; and measuring a value of an electrical property of the 3' end of the extended duplex and a single-stranded portion of the polynucleotide; and (g) identifying the first nucleotide using the value measured in operation (f).

Clause 15. The method of any one of clauses 1 to 14, wherein the first nucleotide is added using a polymerase in contact with the 3' end of the duplex.

Clause 16. The method of clause 15, further comprising reversibly inhibiting the polymerase from adding a second nucleotide to the 3' end of the extended duplex.

Clause 17. The method of clause 16, wherein a blocking moiety reversibly inhibits the polymerase from adding the second nucleotide to the 3' end of the extended duplex.

Clause 18. The method of clause 17, wherein the first nucleotide is coupled to the blocking moiety.

Clause 19. The method of clause 18, wherein the blocking moiety comprises a 3'-blocking group.

Clause 20. The method of clause 17, wherein the blocking moiety is reversibly associated with the extended duplex.

Clause 21. The method of clause 20, further comprising detecting association of the blocking moiety with the extended duplex.

Clause 22. The method of clause 20 or clause 21, further comprising detecting absence of the blocking moiety from the extended duplex.

Clause 23. The method of any one of clauses 17 to 22, further comprising removing the blocking moiety to allow the polymerase to add the second nucleotide to the 3' end of the extended duplex.

Clause 24. The method of any one of clauses 15 to 23, wherein the first force applied in (d) removes the polymerase from contact with the 3' end of the extended duplex.

Clause 25. The method of any one of clauses 15 to 23, further comprising applying a second force to remove the polymerase from contact with the 3' end of the extended duplex, wherein the second force is greater than the first force.

Clause 26. The method of any one of clauses 15 to 25, further comprising: (f) applying a third force disposing the polymerase, in contact with the 3' end of the duplex, within or adjacent to the aperture on the first side of the nanopore, and while applying the third force: inhibiting, using the nanopore, movement of the polymerase into, or further into, the aperture; and measuring the value of the electrical property of the polymerase; and (g) identifying contact of the polymerase with the 3' end of the duplex using the value measured in operation (f).

Clause 27. The method of clause 26, wherein the third force is less than the first force.

Clause 28. The method of clause 26 or clause 27, wherein operation (f) is performed after operation (c) and before operation (d).

Clause 29. The method of any one of clauses 26 to 28, wherein the first nucleotide is associated with a blocking moiety.

Clause 30. The method of clause 29, wherein operation (g) further comprises confirming presence of the blocking moiety associated with the first nucleotide using the value measured in operation (f).

Clause 31. The method of any one of clauses 15 to 30, wherein the polymerase comprises a DNA polymerase.

Clause 32. The method of any one of clauses 15 to 30, wherein the polymerase comprises an RNA polymerase.

Clause 33. The method of any one of clauses 15 to 30, wherein the polymerase comprises a reverse transcriptase.

Clause 34. The method of any one of clauses 1 to 33, wherein the first nucleotide is associated with a blocking moiety, and wherein operation (e) further comprises confirming presence of the blocking moiety associated with the nucleotide using the value measured in operation (d).

Clause 35. The method of clause 34, further comprising removing the blocking moiety from the first nucleotide after operation (d).

Clause 36. The method of clause 35, further comprising, after removing the blocking moiety: (f) again applying the first force disposing the 3' end of the extended duplex within the aperture and the single-stranded portion of the polynucleotide within the aperture, and while again applying the first force: inhibiting, using the nanopore, translocation of the 3' end of the extended duplex to the second side of the nanopore; and measuring the value of the electrical property of the 3' end of the extended duplex and a single-stranded portion of the polynucleotide; and (g) again identifying the first nucleotide using the value measured in operation (f).

Clause 37. The method of clause 36, further comprising removing the blocking moiety from the first nucleotide before operation (d).

Clause 38. The method of any one of clauses 1 to 37, wherein the extended duplex comprises one or more nucleotide analogues.

Clause 39. The method of clause 38, wherein the one or more nucleotide analogues enhance stability of the extended duplex relative to a natural nucleotide.

Clause 40. The method of clause 38 or clause 39, wherein the one or more nucleotide analogues comprise one or more locked nucleic acids (LNA).

Clause 41. The method of any one of clauses 38 to 40, wherein the one or more nucleotide analogues comprise one or more 2'-methoxy (2'-OMe) nucleotides.

Clause 42. The method of any one of clauses 38 to 41, wherein the one or more nucleotide analogues comprise one or more 2'-fluorinated (2'-F) nucleotides.

Clause 43. The method of any one of clauses 38 to 42, wherein the one or more nucleotide analogues alter the value of the electrical property relative to a natural nucleotide.

Clause 44. The method of any one of clauses 38 to 43, wherein the first nucleotide comprises one of the one or more nucleotide analogues.

Clause 45. The method of clause 45, wherein the one or more nucleotide analogues comprise a 2' modification.

Clause 46. The method of clause 44 or clause 45, wherein the one or more nucleotide analogues comprise a base modification.

Clause 47. The method of any one of clauses 1 to 46, wherein the first force is insufficiently strong to cause dissociation of the extended duplex.

Clause 48. The method of any one of clauses 1 to 47, wherein the first force comprises a first voltage.

Clause 49. The method of any one of clauses 1 to 48, wherein operations (b) and (c) are performed in the absence of the first force.

Clause 50. The method of any one of clauses 1 to 49, wherein operation (c) is performed in the presence of a fourth force that opposes the first force.

Clause 51. The method of any one of clauses 1 to 50, wherein a first locking structure is coupled to the 3'-end of the polynucleotide on the first side of the nanopore, the first locking structure inhibiting translocation of the 3'-end of the polynucleotide to the second side of the nanopore through the aperture.

Clause 52. The method of clause 51, wherein the first locking structure is removable.

Clause 53. The method of any one of clauses 1 to 52, wherein a second locking structure is coupled to the 5'-end of the polynucleotide on the second side of the nanopore, the second locking structure inhibiting translocation of the 5'-end of the polynucleotide to the first side of the nanopore through the aperture.

Clause 54. The method of clause 53, wherein the second locking structure is removable.

Clause 55. The method of any one of clauses 1 to 54, further comprising, after operation (d): dissociating the extended duplex from the polynucleotide; and forming a new duplex with the polynucleotide on the first side of the nanopore, the new duplex including a new 3' end.

Clause 56. The method of any one of clauses 1 to 55, wherein operation (a) comprises: contacting the nanopore with the polynucleotide hybridized to a substantially complementary polynucleotide; and applying a sixth force dehybridizing the substantially complementary polynucleotide from the polynucleotide.

Clause 57. The method of any one of clauses 1 to 56, wherein the nanopore comprises a solid-state nanopore.

Clause 58. The method of any one of clauses 1 to 57, wherein the nanopore comprises a biological nanopore.

Clause 59. The method of clause 58, wherein the biological nanopore comprises MspA.

Clause 60. The method of any one of clauses 1 to 59, wherein the first polynucleotide comprises RNA.

Clause 61. The method of any one of clauses 1 to 59, wherein the first polynucleotide comprises DNA.

Clause 62. The method of any one of clauses 1 to 61, wherein the extended duplex comprises a primer hybridized to the polynucleotide.

Clause 63. A sequencing system is provided that includes a nanopore comprising a first side, a second side, and an aperture extending through the first and second sides. The system includes a polynucleotide disposed through the aperture of the nanopore such that a 3' end of the polynucleotide is on the first side of the nanopore, and a 5' end of the polynucleotide is on the second side of the nanopore. The system includes a duplex with the polynucleotide disposed on the first side of the nanopore, the duplex including a 3' end at which a first nucleotide is disposed. The system includes circuitry configured to: apply a first force disposing the 3' end of the duplex within the aperture; measure a value of an electrical property of the 3' end of the duplex and a single-stranded portion of the polynucleotide while applying the first force; and identify the first nucleotide using the measured value, wherein the nanopore inhibits translocation of the 3' end of the duplex to the second side of the nanopore while the first force is applied.

Clause 64. The system of clause 63, wherein the value measured by the circuitry comprises an electrical current, ionic current, electrical resistance, or electrical voltage drop across the nanopore.

Clause 65. The system of clause 63 or clause 64, wherein the value measured by the circuitry comprises noise of an electrical current, ionic current, electrical resistance, or electrical voltage drop across the nanopore.

Clause 66. The system of clause 65, wherein the value measured by the circuitry comprises a standard deviation of the noise.

Clause 67. The system of any one of clauses 63 to 66, wherein the value measured by the circuitry is at least based on M nucleotides of the single-stranded portion of the polynucleotide and D pairs of hybridized nucleotides of the duplex, wherein M is greater than or equal to two, and wherein D is greater than or equal to one.

Clause 68. The system of clause 67, wherein M is greater than or equal to three.

Clause 69. The system of clause 67 or clause 68, wherein D is greater than or equal to two.

Clause 70. The system of any one of clauses 67 to 69, wherein at least one of the M nucleotides of the single-stranded portion comprises a modified base, the circuitry being configured to identify the modified base using the value measured by the circuitry.

Clause 71. The system of clause 70, wherein the modified base comprises a methylated base.

Clause 72. The system of any one of clauses 63 to 71, wherein addition of another nucleotide to the 3' end of the duplex is inhibited while the first force is applied.

Clause 73. The system of clause 72, wherein the nanopore inhibits the addition of another nucleotide.

Clause 74. The system of any one of clauses 63 to 73, wherein the nanopore is oriented so that the first side of the nanopore includes a majority of the aperture.

Clause 75. The system of any one of clauses 63 to 73, wherein the nanopore is oriented so that the second side of the nanopore includes a majority of the aperture.

Clause 76. The system of any one of clauses 63 to 75, wherein the circuitry further is configured to: apply a modified first force again disposing the 3' end of the duplex within the aperture; measure a value of an electrical property of the 3' end of the duplex and a single-stranded portion of the polynucleotide while applying the modified first force; and identify the first nucleotide using the measured value, wherein the nanopore inhibits translocation of the 3' end of the duplex to the second side of the nanopore while the modified first force is applied.

Clause 77. The system of any one of clauses 63 to 76, further comprising a polymerase in contact with the 3' end of the duplex and adding the first nucleotide.

Clause 78. The system of clause 77, wherein the polymerase is reversibly inhibited from adding a second nucleotide to the 3' end of the duplex.

Clause 79. The system of clause 78, further comprising a blocking moiety reversibly inhibiting the polymerase from adding the second nucleotide to the 3' end of the duplex.

Clause 80. The system of clause 79, wherein the first nucleotide is coupled to the blocking moiety.

Clause 81. The system of clause 80, wherein the blocking moiety comprises a 3'-blocking group.

Clause 82. The system of clause 79, wherein the blocking moiety is reversibly associated with the duplex.

Clause 83. The system of clause 82, wherein the circuitry further is configured to detect association of the blocking moiety with the duplex.

Clause 84. The system of clause 82 or clause 83, wherein the circuitry further is configured to detect absence of the blocking moiety from the duplex.

Clause 85. The system of any one of clauses 79 to 84, wherein the blocking moiety is removable to allow the polymerase to add the second nucleotide to the 3' end of the duplex.

Clause 86. The system of any one of clauses 78 to 85, wherein the first force removes the polymerase from contact with the 3' end of the duplex.

Clause 87. The system of any one of clauses 78 to 86, wherein the circuitry further is configured to apply a second force to remove the polymerase from contact with the 3' end of the duplex, wherein the second force is greater than the first force.

Clause 88. The system of any one of clauses 78 to 87, wherein the circuitry further is configured to: apply a third force disposing the polymerase, in contact with the 3' end of the duplex, within or adjacent to the aperture on the first side of the nanopore; measure the value of the electrical property of the polymerase while applying the third force; and identify contact of the polymerase with the 3' end of the duplex using the value measured, wherein the nanopore inhibits movement of the polymerase into, or further into, the aperture.

Clause 89. The system of clause 88, wherein the third force is less than the first force.

Clause 90. The system of clause 88 or clause 89, wherein the circuitry is configured to apply the third force before applying the first force.

Clause 91. The system of any one of clauses 88 to 90, wherein the first nucleotide is associated with a blocking moiety.

Clause 92. The system of clause 91, wherein the circuitry is configured to confirm presence of the blocking moiety associated with the first nucleotide using the value measured.

Clause 93. The system of any one of clauses 77 to 92, wherein the polymerase comprises a DNA polymerase.

Clause 94. The system of any one of clauses 77 to 92, wherein the polymerase comprises an RNA polymerase.

Clause 95. The system of any one of clauses 77 to 92, wherein the polymerase comprises a reverse transcriptase.

Clause 96. The system of any one of clauses 63 to 95, wherein the first nucleotide is associated with a blocking moiety, and wherein the circuitry further is configured to confirm presence of the blocking moiety associated with the nucleotide using the value measured.

Clause 97. The system of clause 96, wherein the blocking moiety is removed from the first nucleotide after applying the first force.

Clause 98. The system of clause 97, wherein the circuitry is configured to, after the blocking moiety is removed: again apply the first force disposing the 3' end of the duplex within the aperture and the single-stranded portion of the polynucleotide within the aperture; while again applying the first force, measure the value of the electrical property of the 3' end of the duplex and a single-stranded portion of the polynucleotide; and again identify the first nucleotide using the value measured, wherein the nanopore inhibits translocation of the 3' end of the duplex to the second side of the nanopore.

Clause 99. The system of clause 98, wherein the blocking moiety is removed from the first nucleotide before the first force is applied.

Clause 100. The system of any one of clauses 63 to 99, wherein the duplex comprises one or more nucleotide analogues.

Clause 101. The system of clause 100, wherein the one or more nucleotide analogues enhance stability of the duplex relative to a natural nucleotide.

Clause 102. The system of clause 100 or clause 101, wherein the one or more nucleotide analogues comprise one or more locked nucleic acids (LNA).

Clause 103. The system of any one of clauses 100 to 102, wherein the one or more nucleotide analogues comprise one or more 2'-methoxy (2'-OMe) nucleotides.

Clause 104. The system of any one of clauses 100 to 103, wherein the one or more nucleotide analogues comprise one or more 2'-fluorinated (2'-F) nucleotides.

Clause 105. The system of any one of clauses 100 to 104, wherein the one or more nucleotide analogues alter the value of the electrical property relative to a natural nucleotide.

Clause 106. The system of any one of clauses 100 to 105, wherein the first nucleotide comprises one of the one or more nucleotide analogues.

Clause 107. The system of clause 106, wherein the one or more nucleotide analogues comprise a 2' modification.

Clause 108. The system of clause 106 or clause 107, wherein the one or more nucleotide analogues comprise a base modification.

Clause 109. The system of any one of clauses 63 to 108, wherein the first force is insufficiently strong to cause dissociation of the duplex.

Clause 110. The system of any one of clauses 63 to 109, wherein the first force comprises a first voltage.

Clause 120. The system of any one of clauses 63 to 110, wherein the polynucleotide is disposed through the aperture and the duplex is disposed on the first side of the nanopore in the absence of the first force.

Clause 121. The system of any one of clauses 63 to 120, wherein the circuitry is configured to apply a fourth force that opposes the first force.

Clause 122. The system of any one of clauses 63 to 121, wherein a first locking structure is coupled to the 3'-end of the polynucleotide on the first side of the nanopore, the first locking structure inhibiting translocation of the 3'-end of the polynucleotide to the second side of the nanopore through the aperture.

Clause 123. The system of clause 122, wherein the first locking structure is removable.

Clause 124. The system of any one of clauses 63 to 123, wherein a second locking structure is coupled to the 5'-end of the polynucleotide on the second side of the nanopore, the second locking structure inhibiting translocation of the 5'-end of the polynucleotide to the first side of the nanopore through the aperture.

Clause 125. The system of clause 124, wherein the second locking structure is removable.

Clause 126. The system of any one of clauses 63 to 125, wherein the circuitry is configured to, after applying the first force, dissociate the duplex from the polynucleotide.

Clause 127. The system of any one of clauses 63 to 126, wherein the circuitry is configured to apply a sixth force dehybridizing a substantially complementary polynucleotide from the polynucleotide so as to dispose the polynucleotide through the aperture of the nanopore.

Clause 128. The system of any one of clauses 63 to 127, wherein the nanopore comprises a solid-state nanopore.

Clause 129. The system of any one of clauses 63 to 128, wherein the nanopore comprises a biological nanopore.

Clause 130. The system of clause 129, wherein the biological nanopore comprises MspA.

Clause 131. The system of any one of clauses 63 to 130, wherein the first polynucleotide comprises RNA.

Clause 132. The system of any one of clauses 63 to 130, wherein the first polynucleotide comprises DNA.

Clause 133. The system of any one of clauses 63 to 132, wherein the duplex comprises a primer hybridized to the polynucleotide.

Clause 134. A method of sequencing an unknown polynucleotide is provided. The method comprises: providing as input to a nucleotide identification module a plurality of measured values of an electrical property of a single-stranded portion of the unknown polynucleotide and a 3' end of a duplex with the unknown polynucleotide within an aperture of a nanopore. The method also comprises using the nucleotide identification module to compare the plurality of measured values to values within a data structure, wherein the data structure correlates different measured values with different combinations of nucleotides within a single-stranded portion of a known polynucleotide and a 3' end of a known duplex including the known polynucleotide within an aperture of a nanopore. The method also comprises using the nucleotide identification module to determine the sequence of nucleotides in the sequence of the unknown polynucleotide using the comparisons. The method also comprises receiving as output from the nucleotide identification module a representation of the determined sequence of nucleotides.

Clause 135. The method of clause 134, wherein the nucleotide identification module comprises a trained machine-learning algorithm.

Clause 136. The method of clause 135, wherein the nucleotide identification module comprises a trained deep learning algorithm.

Clause 137. The method of clause 135 or clause 136, wherein the data structure comprises neurons of the trained machine-learning algorithm.

Clause 138. The method of any one of clauses 134 to 137, wherein the data structure comprises a read map.

Clause 139. The method of clause 138, wherein the read map comprises a look-up table storing the different measured values and representations of the different combinations of nucleotides within the 3' end of the known duplex and the single-stranded portion of the known nucleotide.

Clause 140. The method of any one of clauses 134 to 139, further comprising, by the computer, using a measurement module to generate the plurality of measured values using the aperture of the nanopore.

Clause 141. The method of any one of clauses 134 to 140, further comprising, by the computer, using a nucleotide addition module, a measurement module, and a nucleotide identification module to generate the data structure using the aperture of the nanopore.

Clause 142. A system for sequencing an unknown polynucleotide is provided. The system comprises a processor; and at least one computer-readable medium storing: a plurality of measured values of an electrical property of a single-stranded portion of the unknown polynucleotide and a 3' end of a duplex including the unknown polynucleotide within an aperture of a nanopore. The at least one computer-readable medium further stores a data structure correlating different measured values with different combinations of nucleotides within a single-stranded portion of a known polynucleotide and a 3' end of a known duplex within an aperture of a nanopore. The at least one computer-readable medium further stores instructions for causing the processor to implement operations comprising: comparing the plurality of measured values to the values within the data structure; determining the sequence of nucleotides in the sequence of the unknown polynucleotide using the comparisons; and outputting a representation of the determined sequence of nucleotides.

Clause 143. The system of clause 142, wherein the nucleotide identification module comprises a trained machine-learning algorithm.

Clause 144. The system of clause 143, wherein the nucleotide identification module comprises a trained deep learning algorithm.

Clause 145. The system of clause 143 or clause 144, wherein the data structure comprises neurons of the trained machine-learning algorithm.

Clause 146. The system of any one of clauses 142 to 145, wherein the data structure comprises a read map.

Clause 147. The system of clause 146, wherein the read map comprises a look-up table storing the different measured values and representations of the different combinations of nucleotides within the 3' end of the known duplex and the single-stranded portion of the known nucleotide.

Clause 148. The system of any one of clauses 142 to 147, wherein the instructions further are for causing the processor to generate the plurality of measured values using the aperture of the nanopore.

Clause 149. The system of any one of clauses 142 to 148, wherein the instructions further are for causing the processor to generate the data structure using the aperture of the nanopore.

Clause 150. A method of locking a polynucleotide to a nanopore comprising a first side, a second side, and an aperture extending through the first and second sides is provided. The method comprises: (a) coupling a first locking group to a 3' end of the polynucleotide. The method also comprises (b) disposing the polynucleotide through the aperture of the nanopore such that the 3' end of the polynucleotide and the first locking group are on the first side of the nanopore, and a 5' end of the polynucleotide is on the second side of the nanopore. The method also comprises (c) coupling a second locking group to the 5' end of the polynucleotide on the second side of the nanopore.

Clause 151. The method of clause 150, wherein the first locking group comprises locked nucleic acids (LNA) or peptide nucleic acids (PNA).

Clause 152. The method of clause 150 or 151, wherein the second locking group comprises locked nucleic acids (LNA) or peptide nucleic acids (PNA).

Clause 153. The method of any one of clauses 150 to 152, wherein the polynucleotide is hybridized to a complementary polynucleotide prior to operation (a), the method further comprising dehybridizing the complementary polynucleotide between operations (b) and (c).

Working Examples

The following examples are intended to be purely illustrative, and not limiting.

Figure 11:
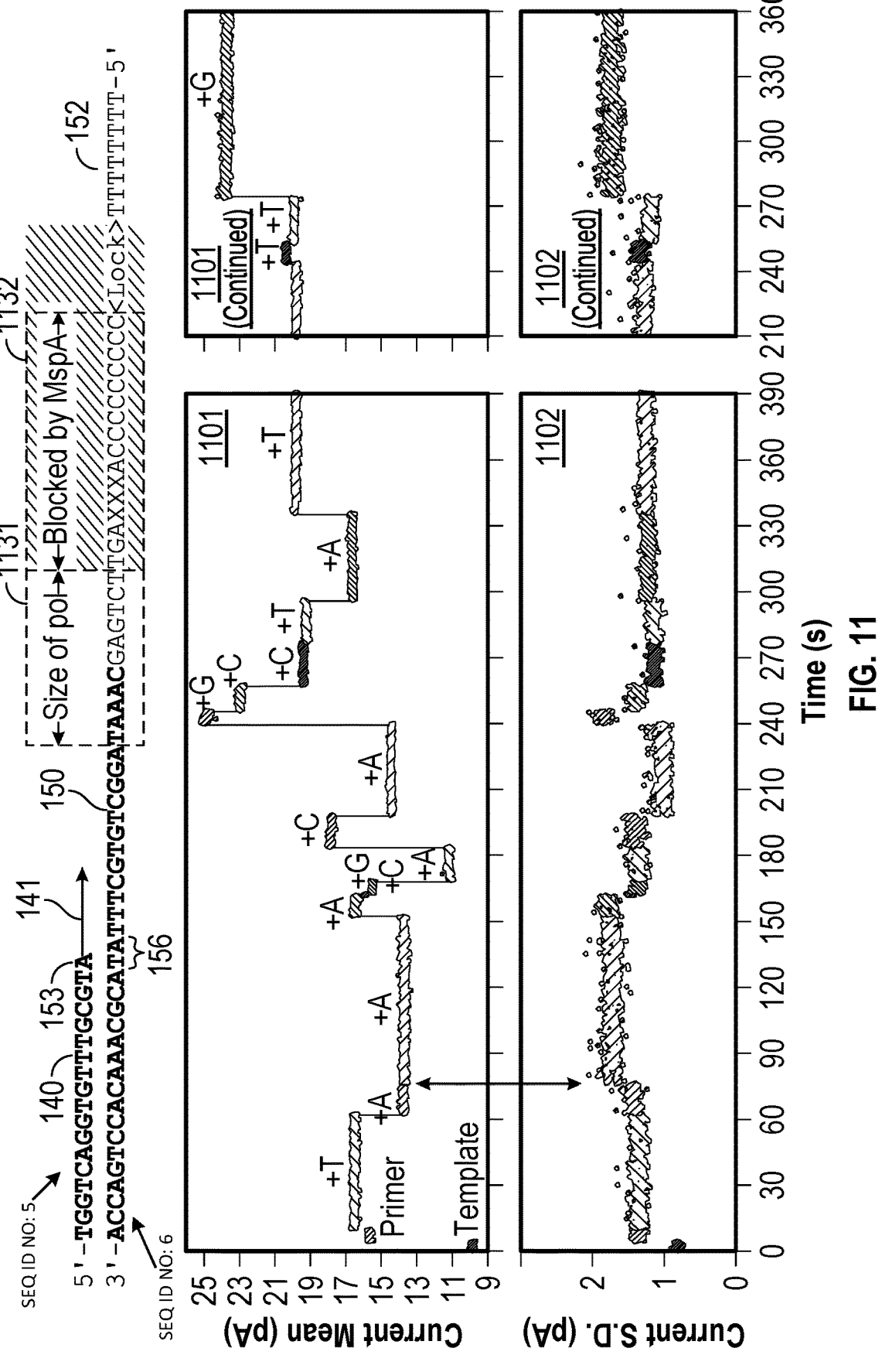
FIG. 11 illustrates plots of values measured as a function of time during sequencing of an example polynucleotide.

FIG. 11 illustrates plots of values measured as a function of time during incorporation using an example template polynucleotide. More specifically, system 100 described with reference to FIGS. 1A-1H was used, in which MspA was used as nanopore 110. Polynucleotides 140 and 150 had the sequences respectively shown in FIG. 11. More specifically, polynucleotide 140 had the sequence 5'-TGGTCAGGTG TTTGCGTA (SEQ ID NO: 5) and polynucleotide 150 had the sequence 3'-ACCAGTCCAC AAACGCATAT TTCGTGTCGG ATAAACGAGT CTTGAXXXXX CCCCCCCCC, or equivalently, 5'-CCCCCCCCCA XXXAGTTCTG AGCAAATAGG CTGTGCTTTA TACGCAAACA CCTGACCA (SEQ ID NO: 6), in which "X" denotes an abasic nucleotide (abasic site), and in which bold indicates the nucleotides in polynucleotide 150 for which signals were obtained as shown in FIG. 11. Note that although polynucleotide 150 included abasic nucleotides, the abasic nucleotides were located in a portion of the polynucleotide 150 that was not sequenced, and the abasic nucleotides were not used to generate signals during any portion of the cycle.

Circuitry 160 was used to apply a second force F2 (here, a −50 mV bias voltage applied for 40 ms in plot 1101 and for 60 ms in the continuation of plot 1101) during which polymerase 105 added the unmodified nucleotides dTTP, dATP, dCTP, and dGTP to polynucleotide 140 based on the sequence of polynucleotide 150 in a manner such as described with reference to FIGS. 1B and 1D, in the direction shown by arrow 141. Circuitry 160 also was used to apply a first force F1 (here, an 85 mV bias voltage applied for 100 ms) disposing the 3' end 153 of the duplex and single-stranded second portion 156 of polynucleotide 140 within the aperture of the nanopore, in a manner such as described with reference to FIGS. 1A, 1C, and 1E. The circuitry 160 alternated between applying the first and second forces. While applying the first force, the circuitry 160 measured the mean electrical current through the nanopore, shown in plot 1101 in FIG. 11. The standard deviation of the mean electrical current is shown in plot 1102 in FIG. 11. In plots 1101 and 1102, the different value levels are denoted as corresponding to the nucleotides that were presumed to have been added to polynucleotide 140 based on the sequence of nucleotides indicated in bold in polynucleotide 150. Each point in FIG. 11 corresponds to the mean current (or standard deviation thereof) measured during one of the 100 ms cycles during which the first force was applied.

Turning first to plot 1101, the mean current of about 10 pA at a time of 0 seconds corresponds to polynucleotide 150 being disposed within nanopore 110 without being hybridized to polynucleotide 140. Then, the mean current increases to about 15.5 pA from about 5-15 seconds, corresponding to annealing of polynucleotide 140 (primer) to polynucleotide 150. Then, mean current increases to about 17 pA from about 15-70 seconds, presumably corresponding to addition of nucleotide T to polynucleotide 140 based on the next nucleotide A in polynucleotide 150. Then, mean current decreases to about 14 pA from about 70-80 seconds, presumably corresponding to addition of nucleotide A to polynucleotide 140 based on the next nucleotide T in polynucleotide 150. Then, mean current remains at about 14 pA from about 80-150 seconds, presumably corresponding to addition of another nucleotide A to polynucleotide 140 based on the next nucleotide T in polynucleotide 150. Then, mean current increases to about 17 pA from about 150-160 seconds, presumably corresponding to addition of another nucleotide A to polynucleotide 140 based on the next nucleotide T in polynucleotide 150. Then, mean current decreases to about 16.5 pA from about 160-162 seconds, presumably corresponding to addition of nucleotide G to polynucleotide 140 based on nucleotide C in polynucleotide 150. Then, mean current decreases to about 15.5 pA from about 162-170 seconds, presumably corresponding to addition of nucleotide C to polynucleotide 140 based on nucleotide G in polynucleotide 150. Then, mean current decreases to about 11.5 pA from about 170-185 seconds, presumably corresponding to addition of nucleotide A to polynucleotide 140 based on nucleotide T in polynucleotide 150. Then, mean current increases to about 18 pA from about 185-200 seconds, presumably corresponding to addition of nucleotide C to polynucleotide 140 based on nucleotide G in polynucleotide 150. Then, mean current increases to about 14.5 pA from about 200-240 seconds, presumably corresponding to addition of nucleotide A to polynucleotide 140 based on nucleotide T in polynucleotide 150. Then, mean current increases to about 25 pA from about 240-250 seconds, presumably corresponding to addition of nucleotide G to polynucleotide 140 based on nucleotide C in polynucleotide 150. In a similar manner, as additional nucleotides were added, the mean current continued to increase or decrease based on the particular combination of nucleotides at the 3' end of the duplex and unpaired nucleotides in single-stranded second region 156 of polynucleotide 150 during the measurement.

From plot 1101, it may be understood that a change in the measured value as a function of time may be used to confirm when polynucleotide 140 (primer) initially is hybridized to polynucleotide 150. For example, the mean current was observed to increase from about 10 pA to about 15.5 pA responsive to hybridization of polynucleotide 140 to polynucleotide 150 (an increase of over about 50%). From plot 1101, it also may be understood that nucleotides may be added to polynucleotide 140 at the 3' end 153 of the duplex, and that change in the measured value as a function of time may be used to confirm when a nucleotide is added to polynucleotide 140. For example, the mean current was observed to increase from about 15.5 pA to about 17 pA with the addition of the first T, and then to decrease from about 17 pA to about 14 pA with the addition of the first A, and so on. The mean current was observed to range from about 11.5 pA (fourth A) to about 25 pA (second G), a change of over about 210%.

From plot 1101, it also may be understood that the change in the measured value may be based not only on the particular nucleotide which is added to the 3' end 153 of the duplex, but on other nucleotides as well. For example, the respective mean currents for the five different As mentioned above were about 14 pA, about 14 pA, about 17 pA, about 11.5 pA, and about 14.5 pA (a variation of over about 45%). If the mean current measured was based solely on the addition of A, then the same value would be expected with each such addition. In some combinations of nucleotides, a similar measured value was observed for the same added nucleotides (e.g., the first and second As), while for other combinations of nucleotides, different measured values were observed for the same added nucleotides (e.g., the third and fourth As, or the first and second Gs).

Turning now to plot 1102, the standard deviations are of the mean current described with reference to plot 1101. The standard deviation of about 0.9 pA at a time of 0 seconds corresponds to polynucleotide 150 being disposed within nanopore 110 without being hybridized to polynucleotide 140. Then, the standard deviation increases to about 1.3 pA from about 5-15 seconds, corresponding to annealing of polynucleotide 140 (primer) to polynucleotide 150. Then, standard deviation remains at about 1.3 pA from about 15-70 seconds, presumably corresponding to addition of nucleotide T to polynucleotide 140 based on the next nucleotide A in polynucleotide 150. Then, standard deviation increases to about 1.4 pA from about 70-80 seconds, presumably corresponding to addition of nucleotide A to polynucleotide 140 based on the next nucleotide T in polynucleotide 150. Then, standard deviation increases to about 1.8 pA from about 80-150 seconds, presumably corresponding to addition of another nucleotide A to polynucleotide 140 based on the next nucleotide T in polynucleotide 150. Then, standard deviation increases to about 1.9 pA from about 150-160 seconds, presumably corresponding to addition of another nucleotide A to polynucleotide 140 based on the next nucleotide T in polynucleotide 150. Then, standard deviation decreases to about 1.4 pA from about 160-162 seconds, presumably corresponding to addition of nucleotide G to polynucleotide 140 based on nucleotide C in polynucleotide 150. Then, standard deviation decreases to about 1.3 pA from about 162-170 seconds, presumably corresponding to addition of nucleotide C to polynucleotide 140 based on nucleotide G in polynucleotide 150. Then, standard deviation remains at about 1.3 pA from about 170-185 seconds, presumably corresponding to addition of nucleotide A to polynucleotide 140 based on nucleotide T in polynucleotide 150. Then, standard deviation increases to about 1.4 pA from about 185-200 seconds, presumably corresponding to addition of nucleotide C to polynucleotide 140 based on nucleotide G in polynucleotide 150. Then, standard deviation decreases to about 1.1 pA from about 200-240 seconds, presumably corresponding to addition of nucleotide A to polynucleotide 140 based on nucleotide T in polynucleotide 150. Then, standard deviation increases to about 1.9 pA from about 240-250 seconds, presumably corresponding to addition of nucleotide G to polynucleotide 140 based on nucleotide C in polynucleotide 150. In a similar manner, as additional nucleotides were added, the standard deviation continued to increase or decrease based on the particular combination of nucleotides at the 3' end of the duplex and unpaired nucleotides in single-stranded second region 156 of polynucleotide 150 during the measurement.

From plot 1102, it may be understood that a change in the standard deviation as a function of time may be used to confirm when polynucleotide 140 (primer) initially is hybridized to polynucleotide 150. For example, the standard deviation was observed to increase from about 0.9 pA to about 1.3 pA responsive to hybridization of polynucleotide 140 to polynucleotide 150 (an increase of over about 40%). From plot 1102, it also may be understood that nucleotides may be added to polynucleotide 140 at the 3' end 153 of the duplex, and that change in the standard deviation as a function of time may be used to confirm when a nucleotide is added to polynucleotide 140. For example, the standard deviation was observed to increase from about 1.4 pA to about 1.9 pA between addition of the first and second As, and so on. The standard deviation was observed to range from about 1.1 pA (fifth A) to about 1.9 pA (second G), a change of over about 70%.

From plot 1102, it also may be understood that the change in the standard deviation may be based not only on the particular nucleotide which is added to the 3' end 153 of the duplex, but on other nucleotides as well. For example, the respective standard deviations for the five different As mentioned above were about 1.4 pA, about 1.8 pA, about 1.9 pA, about 1.3 pA, and about 1.1 pA (a variation of over about 70%). If the standard deviation was based solely on the addition of A, then the same value would be expected with each such addition. In some combinations of nucleotides, a similar standard deviation was observed for the same added nucleotides (e.g., the second and third As, or the first and fourth As), while for other combinations of nucleotides, different standard deviations were observed for the same added nucleotides (e.g., the first and fifth As).

From plots 1101 and 1102, it also may be understood that the use of multiple different types of measured values may be used to distinguish between different nucleotides. For example, some nucleotides may have similar values as one another for a certain measurement type, and different values than one another for another measurement type. Such similar measured values may be referred to herein as being "degenerate" because additional information may be needed to distinguish the nucleotides from one another. In a manner such as described with reference to FIG. 8E, that additional information may include the standard deviation of those measured values. Illustratively, as shown in plot 1101, the first and second As may have similar mean currents as one another, and thus may be considered to be "degenerate" with respect to that metric, measured under those particular conditions. However, as shown in plot 1102, the standard deviation in the mean current for the first A may be readily distinguished from that for the second A. Accordingly, it may be understood that even if the mean currents alone may be insufficient to distinguish certain nucleotides, the standard deviations (or other type of measured values) may be sufficient to distinguish those nucleotides. Conversely, as shown in plot 1102, the T and first A may have similar standard deviations as one another, and thus may be considered to be "degenerate" with respect to that metric, measured under those particular conditions. However, as shown in plot 1101, the mean current for the T may be readily distinguished from that for the first A. Accordingly, it may be understood that even if the standard deviations alone, measured under those specific conditions, may be insufficient to distinguish certain nucleotides, the mean current (or other type of measured values) may be sufficient to distinguish those nucleotides. It also may be understood that multiple different types of information to characterize combinations of nucleotides at the 3' end 153 of the duplex and in single-stranded second portion 156 of polynucleotide 150 may be used to readily resolve any degeneracies. Note that such different types of information need not necessarily require making multiple types of measurements, but instead may involve obtaining different types of information from the same set of measurements—illustratively, the measured value and its standard deviation. More generally, it is expected that different sets of measurement conditions (e.g., different voltages, different fluid composition such as different salt concentration, or the like), may be used to characterize the same sequences of nucleotides in different ways, at least some of which are not "degenerate" and thus permit the nucleotides to be distinguished from one another.

From plots 1101 and 1102, it also may be understood that polynucleotide 140 may be extended sufficiently far that interactions between polymerase and nanopore 110 may inhibit any further extension of polynucleotide 140. For example, window 1132 illustrated in FIG. 11 illustrates the approximate location of the MspA nanopore 110 relative to polynucleotide 150 when circuitry 160 applies the second force F2 such that lock 152 is disposed against nanopore 110 in a manner such as described with reference to FIGS. 1B and 1D. Although the working example as illustrated in FIG. 11 shows abasic nucleotides in window 1132, any suitable components may be used in window 1132, such as natural nucleotides, non-natural nucleotides, abasic nucleotides, other suitable chemical components, and combinations thereof. Window 1131 illustrated in FIG. 11 illustrates the approximate location of polymerase 105 when polynucleotide 140 is sufficiently extended that the polymerase becomes lodged against the nanopore and no longer may access the 3' end 153 of the duplex.

Figure 12:
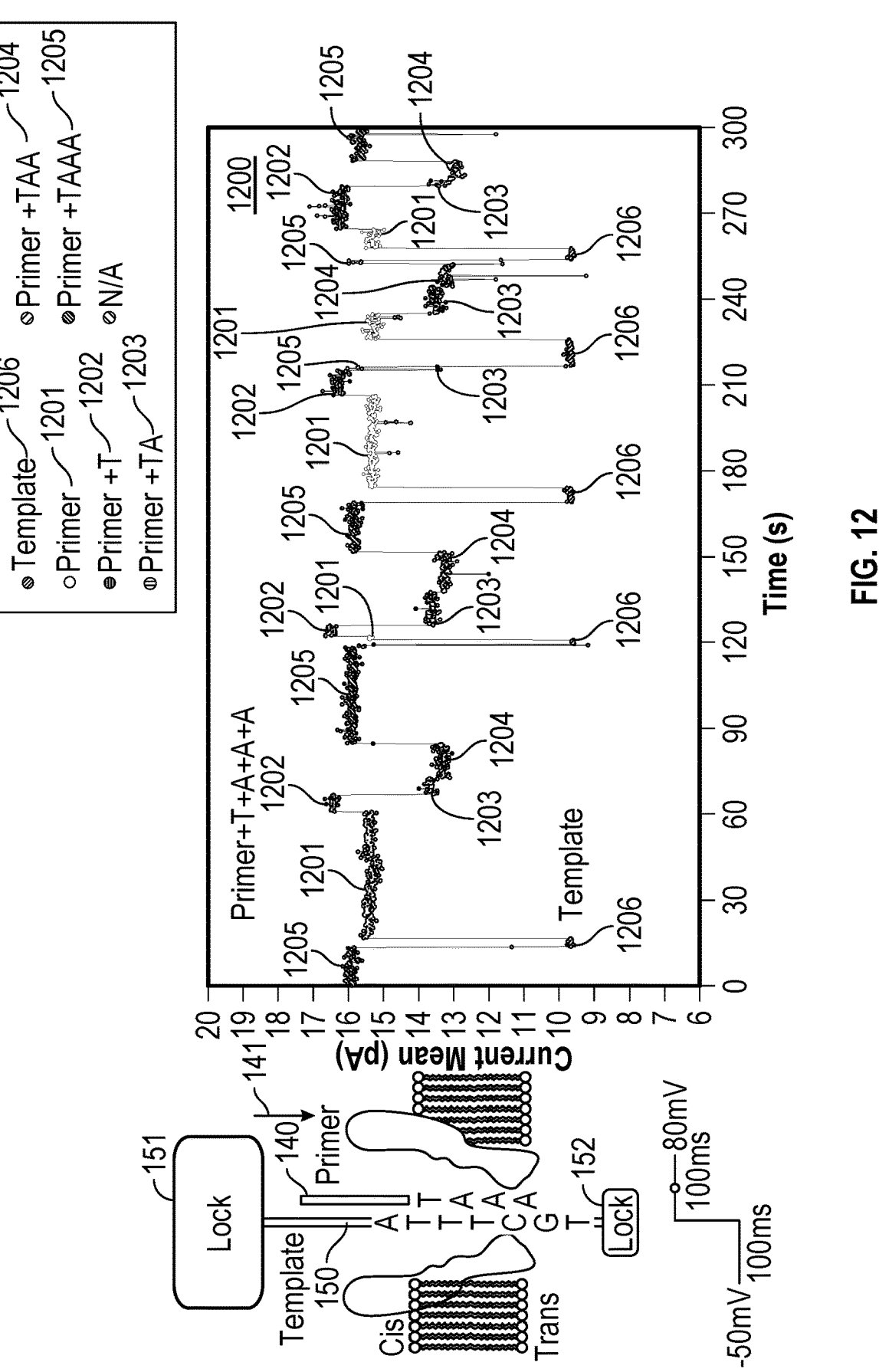
FIG. 12 illustrates plots of values measured during resequencing of an example polynucleotide under a set of measurement conditions.

As noted above with reference to FIGS. 1G, 4A-4C, 8A-8E, and 9, polynucleotide 150 may be sequenced and resequenced under the same set of measurement conditions, or a different set of measurement conditions. FIG. 12 illustrates plots of values measured during resequencing of an example polynucleotide under a set of measurement conditions. More specifically, system 100 described with reference to FIGS. 1A-1H, in which MspA was used as nanopore 110, was used in a manner similar to that described with reference to FIG. 11. An excess of primer (polynucleotide 140) and polymerase were added to the fluid on the first side of the nanopore, and the primer hybridized to the polynucleotide 150. Polynucleotides 140 and 150 had the sequences respectively shown in FIG. 12 (3'-ATTTCGT-5' for polynucleotide 150, and 5'-TAAA-3' for polynucleotide 140). Circuitry 160 was used to apply a second force F2 (here, a −50 mV bias voltage) during which polymerase 105 added the unmodified nucleotides dTTP and dATP to polynucle-
otide 140 based on the sequence of polynucleotide 150 in a
manner such as described with reference to FIGS. 1B and
1D, in the direction shown by arrow 141. While dCTP was
present as well, dGTP was excluded so as to inhibit exten-
sion of polynucleotide 140 past the sequence T-A-A-A.
Circuitry 160 also was used to apply a first force F1 (here,
an 80 mV bias voltage) disposing the 3' end 153 of the
duplex and single-stranded second portion 156 of polynucle-
otide 150 within the aperture of the nanopore, in a manner
such as described with reference to FIGS. 1A, 1C, and 1E.
The circuitry 160 alternated between first and second forces
at 100 ms intervals. While applying the first force, the
circuitry 160 measured the mean electrical current through
the nanopore, shown in plot 1201 in FIG. 12. After the
nucleotides T-A-A-A were added to polynucleotide 140, the
extended polynucleotide 140 spontaneously dissociated
from polynucleotide 150. The circuitry then was used to
again alternate between applying the second force and first
force at 100 ms intervals. During application of the second
force, a new primer (polynucleotide 140) hybridized to
polynucleotide 150 in a manner such as described with
reference to FIG. 4C, and such primer then was extended to
resequence polynucleotide 150. Such cycles of stripping and
resequencing were repeated several times.

In plot 1200, the different value levels are coded as
follows, and as shown in the legend: template alone=1206,
primer (hybridized to template)=1201, primer+T (hybrid-
ized to template)=1202, primer+TA (hybridized to template)
=1203, primer+TAA (hybridized to template)=1204,
primer+TAAA (hybridized to template)=1205. Each point in
FIG. 12 corresponds to the mean current measured during
one of the 100 ms cycles during which the first force was
applied. It may be seen in plot 1200 that at times of about
15 seconds, 120 seconds, 170 seconds, 220 seconds, and 260
seconds, the mean current corresponded to that of template
(polynucleotide 150) without the primer (1205). Each of
such times was followed by a mean current corresponding to
hybridization of primer (polynucleotide 140) to the template
(1201). Each of such times then was followed by a sequence
of mean currents corresponding to sequential additions to
the primer of T (1202), then A (1203), then another A (1204),
and then another A (1205). Although the mean currents for
additions of the first, second, and third As may be seen to
differ from one another (compare 1203, 1204, 1205 to one
another), it may be seen that in each resequencing cycle
those As have the same mean currents as they respectively
did in the other cycles. Accordingly, from FIG. 12 it may be
understood that a polynucleotide repeatedly may be rese-
quenced by stripping off the extended polynucleotide 140
and adding and extending a new polynucleotide 140, and
that the values during each resequencing cycle correlate
reliably to the sequence of nucleotides added to polynucle-
otide 140, and thus to the sequence of polynucleotide 150.

Figure 13A:
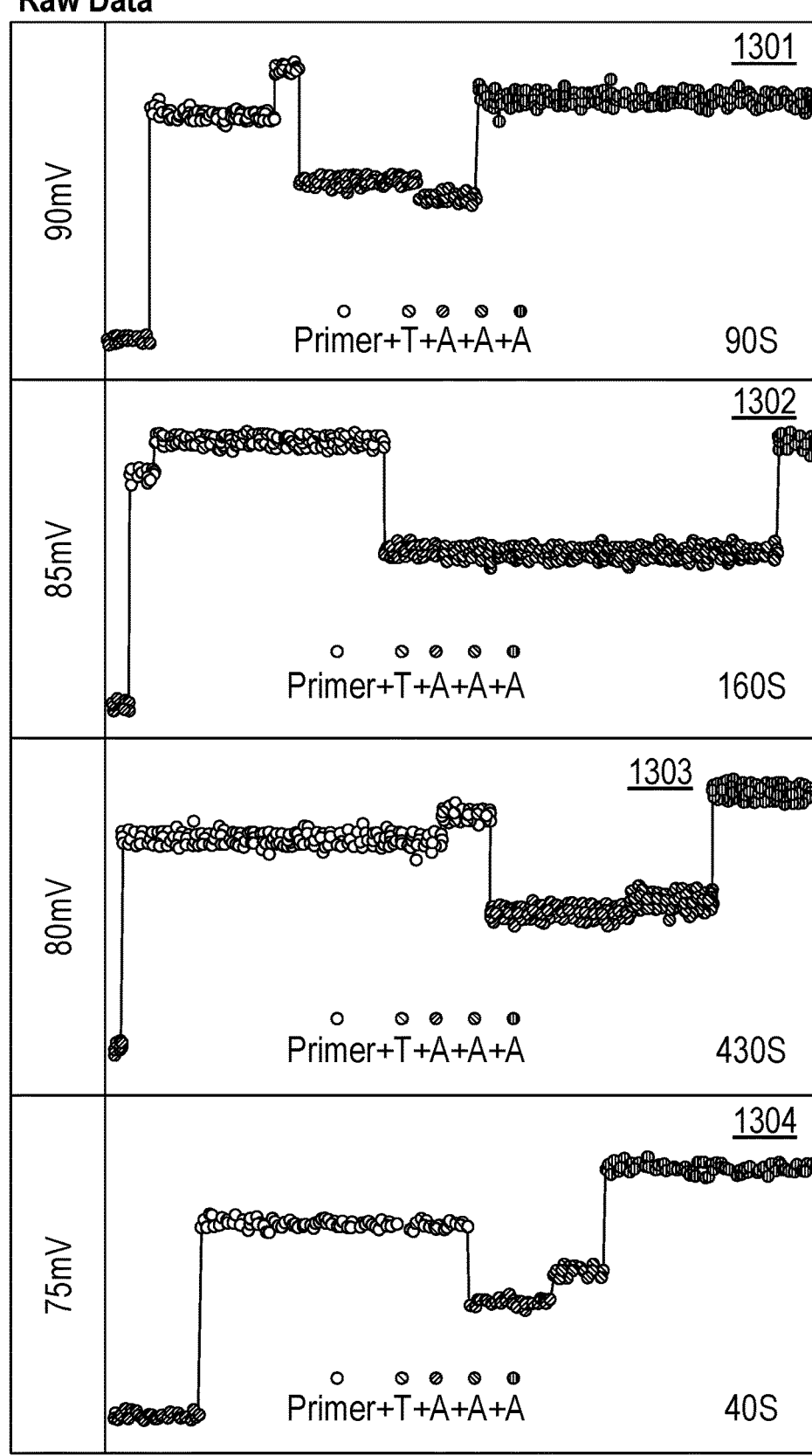
FIGS. 13A-13C illustrate plots of values measured during resequencing of an example polynucleotide under different sets of measurement conditions.
Figure 13B:
Figure 13C:
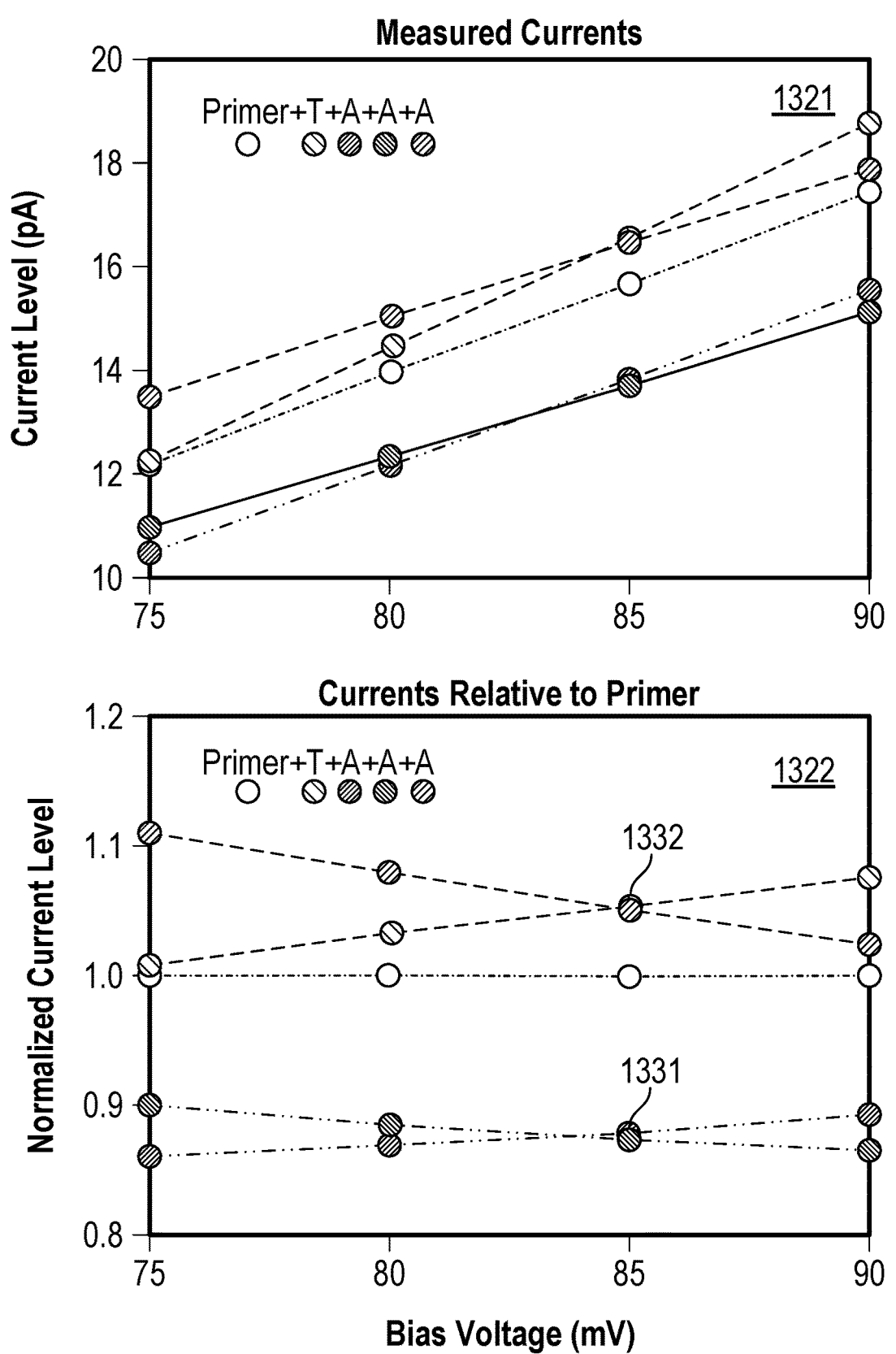

FIGS. 13A-13C illustrate plots of values measured during
resequencing of an example polynucleotide under different
sets of measurement conditions. More specifically, system
100 described with reference to FIGS. 1A-1H, in which
MspA was used as nanopore 110, was used in a manner
similar to that described with reference to FIGS. 11 and 12.
Polynucleotides 140 and 150 had the sequences respectively
shown in FIG. 12. Circuitry 160 was used to apply a second
force F2 (here, a −50 mV bias voltage) during which
polymerase 105 added the unmodified nucleotides dTTP and
dATP to polynucleotide 140 based on the sequence of
polynucleotide 150 in a manner such as described with
reference to FIGS. 1B and 1D, in the direction shown by arrow 141. While dCTP was present as well, dGTP was
excluded so as to inhibit extension of polynucleotide 140
past the sequence T-A-A-A. Circuitry 160 also was used to
sequentially apply several different (modulated) first forces
F1, F1', F1", F1''' created by specific bias voltages (here, 75
mV, 80 mV, 85 mV, and 90 mV bias voltages, each applied
for 100 ms). Each of the first forces disposed the 3' end 153
of the duplex and single-stranded second portion 156 of
polynucleotide 150 within the aperture of the nanopore, in a
manner such as described with reference to FIGS. 1A, 1C,
and 1E. Without wishing to be bound by any theory, it is
believed that in a manner such as described with reference
to FIG. 1G, the different forces caused the nucleotides in the
duplex and single-stranded second portion of polynucleotide
150 to interact differently with the nanopore, resulting in
different measured values. After applying the four different
first forces, circuitry 160 applied the second force (−50 mV
for 100 ms), resulting in addition of another nucleotide
followed by sequentially applying the four different first
forces.

In a manner similar to that described elsewhere herein,
while applying each of the first forces, the circuitry 160
measured the mean electrical current through the nanopore,
shown in a respective one of the plots 1301, 1302, 1303,
1304 in FIG. 13A. After the nucleotides T-A-A-A were
added to polynucleotide 140, the extended polynucleotide
140 dissociated from polynucleotide 150A new primer
(polynucleotide 140) then was hybridized to polynucleotide
150 in a manner such as described with reference to FIG. 4C,
and extended to resequence polynucleotide 150. Note that
each of the first forces was applied for 100 ms in this
example, resulting in a read cycle of 400 msec (for reads at
each of the four voltages), for example. The plots of the
different read voltage values are illustrated vertically, so that
they all reference the start time of the same read cycle.
Optionally, after it has been determined that the nucleotides
have been sufficiently characterized with those reads, force
F2 may be applied to incorporate the next nucleotide.
Accordingly, it will be appreciated that for each cycle a
single F2 may be applied, and as many different read
voltages, for as long a duration as desired, may be applied
in any desired sequence. Then, after going through the whole
template, F4 may be applied to strip the template, and the
sequencing process repeated as many times as desired, using
fresh primers.

In plot 1301, corresponding to a 90 mV first force F1, the
different value levels are coded using different fills to
correspond to hybridization of the primer (polynucleotide
140) or the sequence of nucleotides T-A-A-A, and each point
corresponds to the mean current measured during one of the
100 ms cycles during which the 90 mV first force F1''' was
applied, as a function of time. Plot 1302 was obtained
similarly with an 85 mV first force F1". Plot 1303 was
obtained similarly with an 80 mV first force F1'. Plot 1304
was obtained similarly with a 75 mV first force F1. It may
seen in each of plots 1301, 1302, 1303, and 1304 that at a
time of about 0 seconds, the mean current corresponded to
that of template (polynucleotide 150) without the primer.
This was followed by a mean current corresponding to
hybridization of primer (polynucleotide 140) to the tem-
plate. This then was followed by a sequence of mean
currents corresponding to sequential additions of T, A, A,
and A to the primer. From plots 1301, 1302, 1303, and 1304,
it may be seen that the mean currents respectively corre-
sponding to hybridization of the primer, or to different nucleotides, under a given first force F1 are similar to one another in some regards, and are different than each other in other regards.

Plots 1311, 1312, 1313, and 1314 in FIG. 13B illustrate the mean signal levels of each of the mean currents of FIG. 13A as a function of step (also referred to as the sequence index), so as to facilitate comparison of the raw data within plots 1301, 1302, 1303, and 1304, respectively. The signal levels shown are the means over the entire time that a particular base was at the 3' end 153 of duplex 154. It will be appreciated that the amount of time for a particular nucleotide incorporation can vary, e.g., a given incorporation can occur in less than one cycle between the first forces and second force, or over the course of many such cycles. In plots 1311, 1312, 1313, and 1314, the signal level corresponding to hybridization of the primer is higher than that corresponding to polynucleotide 150 without such hybridization. In plots 1311, 1312, and 1313 the signal level corresponding to extension of the primer by T is higher than that corresponding to hybridization of the primer, while in plot 1314 the signal level corresponding to extension of the primer by T is similar as that corresponding to hybridization of the primer (but still distinguishable). In plots 1311, 1312, 1313, and 1314, the signal level corresponding to extension of the primer by T is different than those corresponding to extension by each of the three As. In each of plots 1311, 1313, and 1314, the signal levels respectively corresponding to extension of the primer by each of the three As are different than one another, while in plot 1312 the signal levels corresponding to extension of the primer by the first and second As are about the same as each other (degenerate).

Plot 1321 in FIG. 13C illustrates the mean signal (measured current) levels of FIG. 13B as a function of bias voltage, so as further to facilitate comparison of the raw data within plots 1301, 1302, 1303, and 1304, respectively. It may be seen in plot 1321 that each of the signal levels increases as a function of the bias voltage applied during the measurement, and that at least some of the signal levels have different slopes than one another. So as to facilitate comparison of the different slopes in plot 1321, plot 1322 in FIG. 13C illustrates the normalized mean signal levels of FIG. 13B as a function of bias voltage, in which the signal levels were normalized by dividing the mean signal level corresponding to the added nucleotide by the mean signal level corresponding to hybridization of the primer. It may be seen that the normalized signal level for T is significantly higher than that for the first A and changes in a different direction. It also may be seen that the normalized signal level for the first A is similar to that of the second A (but still distinguishable) but changes in a different direction. Intersection point 1331 corresponds to the approximate bias voltage (85 mV) at which the normalized signal levels for the first and second As are approximately the same as one another (degenerate). It also may be seen that the normalized signal level for the third A is significantly higher than that for the first and second As, and changes in the same direction as that of the first A and in a different direction than that of the second A and the T. Intersection point 1332 corresponds to the approximate bias voltage (85 mV) at which the normalized signal levels for the T and third A are approximately the same as one another (degenerate).

Accordingly, from FIGS. 13A-13C it may be understood that at some first forces F1, the measured values for certain combinations of nucleotides may be degenerate, while at other first forces F1', F1", F1''' (which may be sequentially applied between nucleotide addition cycles using F2), the measured values for some or all combinations of nucleotides may be readily distinguished. As such, it will be appreciated that measurements may be performed using any suitable number of forces to obtain measured values from which any degeneracies in the measured values may be resolved. In other examples, the measurements may be performed using different first forces that are selected such that each possible combination of nucleotides has a measured value that is readily distinguished from that of other combinations under at least one of such first forces. From FIGS. 13A-13C it also may be understood that applying a different force using circuitry 160 may move the 3' end of the duplex, and the second portion of polynucleotide 150, to a different location relative to nanopore 110 at which nucleotides in the duplex and polynucleotide 150 may affect the measured value differently than they do at another location (under another force). In a manner such as described with reference to FIGS. 1G and 8C, changes in the measurement conditions may linearly or nonlinearly affect the measured values, and indeed may change the measured values in different directions for different combinations of nucleotides at the 3' end of the duplex and within the second portion of polynucleotide 150. Note that although each of plots 1301, 1302, 1303, 1304 were obtained while sequencing polynucleotide 150 using sequentially applied forces F1, F1', F1", F1''', in other configurations circuit 160 may be configured to sequence polynucleotide 150 using a selected one of the first forces, and then to sequence polynucleotide using one or more other ones of the first forces.

Figure 14:
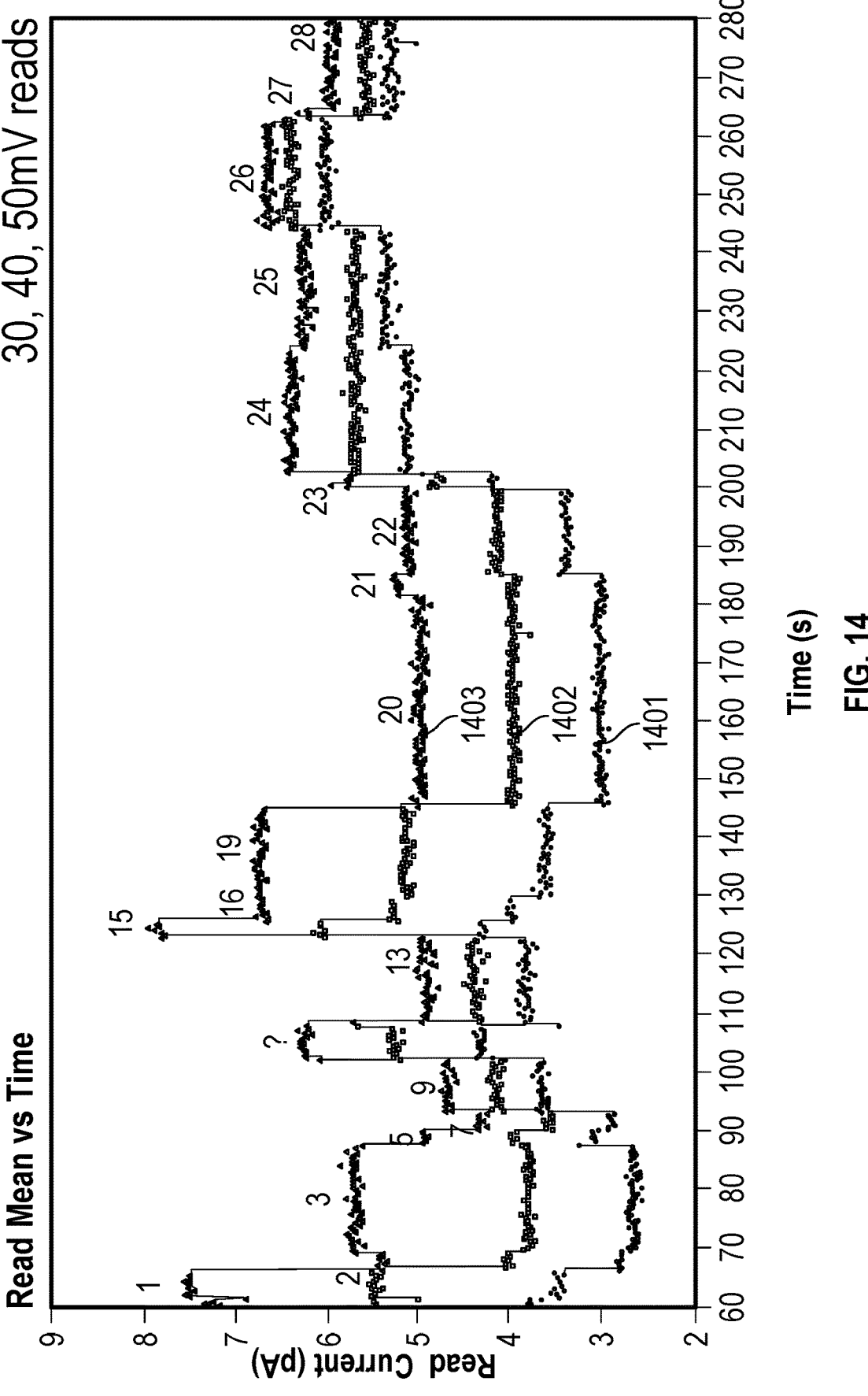
FIG. 14 illustrates plots of values measured during resequencing of an example polynucleotide under different sets of measurement conditions, in which the sequencing system has alternative configuration described with reference to FIG. 7.

The measured values described with reference to FIGS. 11, 12, and 13A-13C were obtained using an MspA nanopore 110 that was oriented so that first side 111 of the nanopore includes the majority of aperture 113, such that 3' end 153 of duplex 154 may fit relatively deeply within aperture 113, in a manner such as illustrated in FIGS. 1A-1H. FIG. 14 illustrates plots of values measured during resequencing of an example polynucleotide under different sets of measurement conditions, in which the sequencing system has an alternative configuration described with reference to FIG. 7. More specifically, MspA nanopore 110 was oriented so that second side 112 of the nanopore includes the majority of aperture 113, such that 3' end of duplex 154 may fit relatively shallowly within aperture 113. Twenty-eight nucleotides within polynucleotide 150 were resequenced using first forces of 30 mV (trace 1401), 40 mV (trace 1402), and 50 mV (trace 1403) in a manner similar to that described with reference to FIGS. 11, 12, and 13A, and it may be seen in FIG. 14 that different current levels were observed corresponding to different combinations of nucleotides at the 3' end 153 of the duplex and in the second portion of polynucleotide 150, using the different first forces. Accordingly, from FIG. 14 it may be understood that regardless of the orientation of the nanopore, addition of nucleotides to polynucleotide 140 results in measured values that correlate to the resulting combination of nucleotides at the 3' end 153 of the duplex and in the second portion of polynucleotide 150. The numbers shown above trace 1403 correspond to assignments of different signal levels to different nucleotides that were added.

Figure 15A:
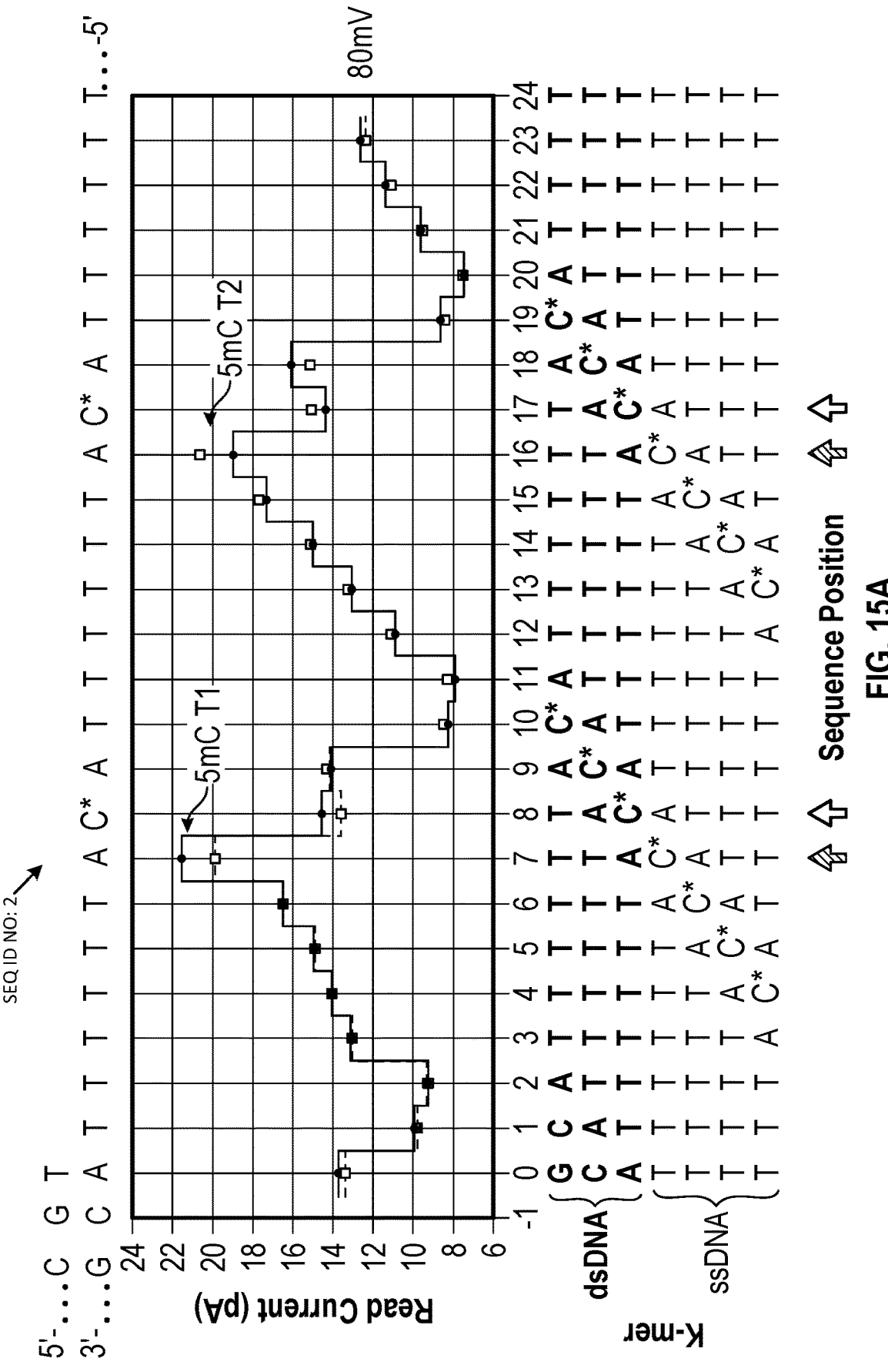
FIGS. 15A-15B (SEQ ID NO: 2) illustrate plots of values measured during sequencing of a polynucleotide including a modified base.
Figure 15B:
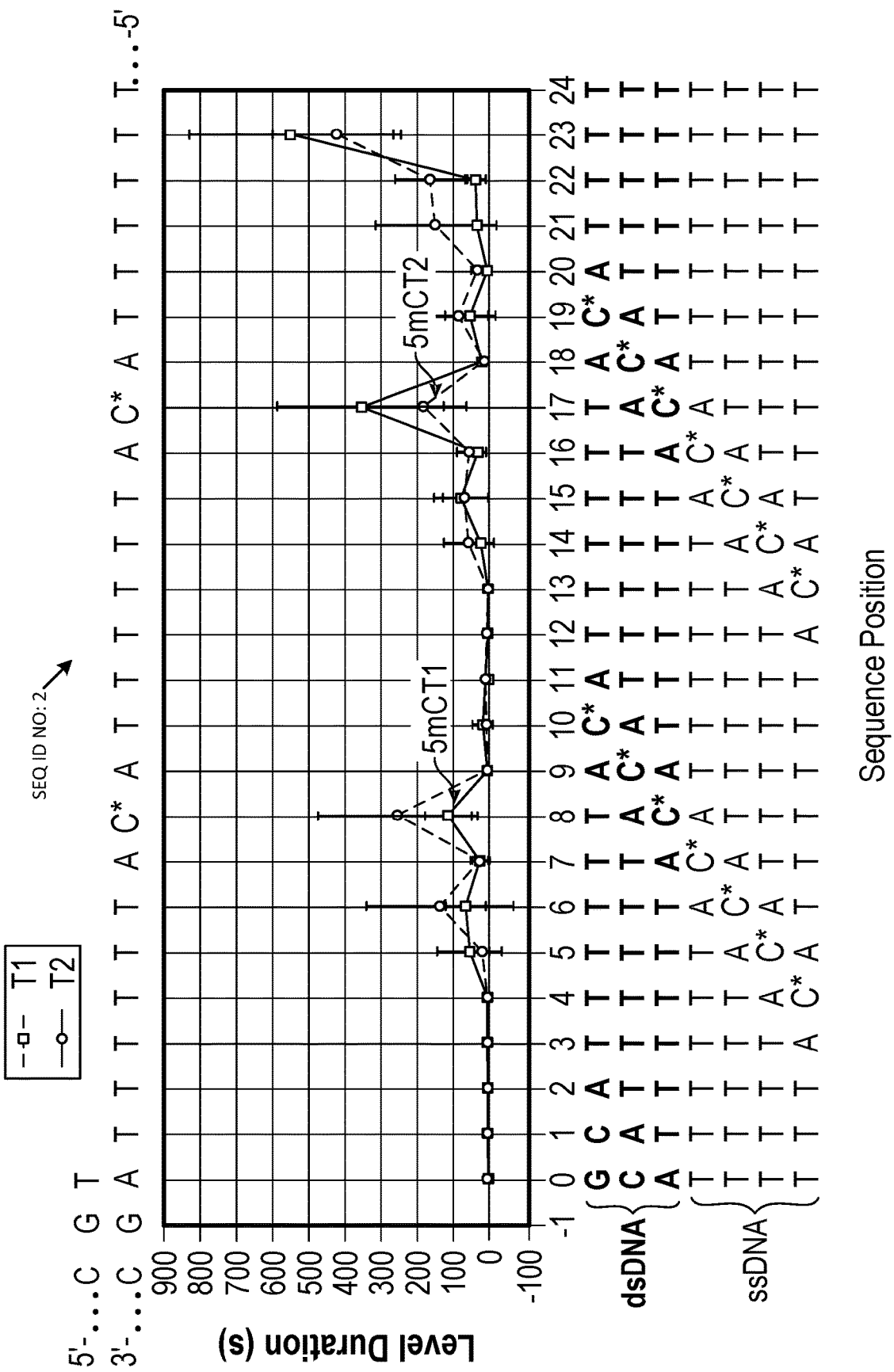

The example system described with reference to FIGS. 11, 12, 13A-13C, and 14 also was used to demonstrate that modified bases, such as methylated bases, may be identified. For example, FIGS. 15A-15B illustrate plots of values measured during sequencing of a polynucleotide including a modified base. Two version of polynucleotide 150 were prepared, one having the sequence 3'-GCATTTTTTACAT-TTTTTACATTTTTT-5' (SEQ ID NO: 1) and the other having a similar sequence 3'-GCATTTTTTAC*ATTTTTTAC*ATTTTTT-5' (SEQ ID NO: 2) in which the cytosines denoted in bold and with asterisks were methylated (5mC) in some measurement, and were not methylated in other measurements. The primer 5'-CGT was hybridized to each of these sequences poly-nucleotide 150 in the manner illustrated in FIG. 15A and extended in a manner such as described with reference to FIG. 11, in which circuitry 160 alternated between applying first force 80 mV (read voltage) and second force −50 mV (incorporation voltage). Each read was performed twice (T1 and T2).

FIG. 15A illustrates the mean currents over the entire time that a particular base was at the 3' end 153 of duplex 154, similarly as described for FIG. 13B. The approximate K-mers believed to be located in the sensing region of the nanopore, for the sequence shown above the plot in FIG. 15A (SEQ ID NO: 2), are illustrated below the respective signal levels that were measured. In one set of measurements, the sequence included methylcytosine (5mC, denoted C*), while in another set of measurements the methylcyto-sine in the sequence was replaced with cytosine (that is, the C* in the sequence was replaced with C). It may be seen that for K-mers 0, 1, 2, 3, 4, 5, 6, 9, 10, 11, 12, 13, 14, 19, 20, 21, 22, 23, and 24, the read currents for the two sequences are similar to one another. This was attributed to the cytosine or methylcytosine being sufficiently far away from the read head of the nanopore as either to affect the read current similarly as one another, or as not to significantly affect the read current. In comparison, for K-mers 7, 8, 15, 16, 17, and 18, the read currents for the two sequences differed signifi-cantly from one another. This was attributed to the cytosine or methylcytosine at the respective locations denoted C* being sufficiently close to the read head of the nanopore as to affect the read current differently from one another in a readily distinguishable way, e.g., at locations 5 and 4 illus-trated in FIG. 1F for the first methylcytosine in the sequence, and at locations 6, 5, 4, and 3 illustrated in FIG. 1F for the second methylcytosine in the sequence.

FIG. 15B illustrates the difference in time over which a given mean current was observed while particular base was at the 3' end 153 of duplex 154 (level duration) for the same sequence (SEQ ID NO: 2), again comparing the measure-ment with cytosine at the locations denoted C* relative to the sequence with 5mC at the locations denoted C*. The approximate K-mers believed to be located in the sensing region of the nanopore are again illustrated below the respective signal levels that were measured. It may be seen that for K-mers 0, 1, 2, 3, 4, 9, 10, 11, 12, and 13, the level durations for the two sequences are similar to one another. This was attributed to the cytosine or methylcytosine being sufficiently far away from the read head of the nanopore as either to affect the read current similarly as one another, or as not to significantly affect the read current. In comparison, for K-mers 5, 6, 7, 8, 14, 15, 16, 17, the level durations for the two sequences differed significantly from one another. This was attributed to the cytosine or methylcytosine being sufficiently close to the read head of the nanopore as to affect the level duration differently from one another in a readily distinguishable way, e.g., at locations 7, 6, 5, and 4 illus-trated in FIG. 1F for the first methylcytosine in the sequence, and at locations 7, 6, 5, and 4 illustrated in FIG. 1F for the second methylcytosine in the sequence.

From the plots described with reference to FIGS. 11, 12, 13A-13C, 14, and 15A-15B, it further may be understood that circuitry 160 may be used to obtain the measured value for each nucleotide addition with any desired level of accuracy. The level of accuracy may be increased by resolv-ing degeneracies using multiple different first forces F1, F1', F1". For example, while circuitry 160 applies any suitable number of first force(s), nanopore 110 inhibits a polymerase from adding another nucleotide to the 3' end 153 of the duplex in a manner such as described with reference to FIGS. 1A, 1C, and 1C. As noted elsewhere herein, circuitry 160 may be configured to sequentially apply any suitable number of first forces F1, F1', F1", and so on for any suitable amount of time to obtain a measured value with sufficient SNR for the particular context in which the sequencing system and method is being implemented, substantially without the risk of another nucleotide being added during such measurement. Accordingly, from the results herein, it may be understood that the stepwise addition and charac-terization of single nucleotides may be highly controlled and used to sequence polynucleotides with any suitable level of speed or accuracy.

ADDITIONAL COMMENTS

While various illustrative examples are described above, it will be apparent to one skilled in the art that various changes and modifications may be made therein without departing from the invention. The appended claims are intended to cover all such changes and modifications that fall within the true spirit and scope of the invention.

It is to be understood that any respective features/ex-amples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

---

What is claimed is:

1. A method of sequencing a polynucleotide using a nanopore comprising a first side, a second side, and an aperture extending through the first and second sides, the method comprising:

(a) disposing a polynucleotide through the aperture of the nanopore such that a 3' end of the polynucleotide is on the first side of the nanopore, and a 5' end of the polynucleotide is on the second side of the nanopore;

(b) hybridizing a primer to a primer binding sequence in the polynucleotide to form a duplex on the first side of the nanopore, the duplex including a 3' end corresponding to a 3' end of the primer;

(c) extending the duplex on the first side of the nanopore by adding a natural nucleotide to the 3' end of the duplex;

(d) applying a force disposing the 3' end of the extended duplex within the aperture, and while applying the force:

inhibiting, using the nanopore, translocation of the 3' end of the extended duplex to the second side of the nanopore; and measuring a value of an electrical property of the 3' end of the extended duplex and a single-stranded portion of the polynucleotide; and (e) identifying the natural nucleotide using the value measured in operation (d).

2. The method of claim 1, wherein the value measured in operation (d) comprises an electrical current, ionic current, electrical resistance, or electrical voltage drop across the nanopore.

3. The method of claim 1, wherein the value measured in operation (d) comprises noise of an electrical current, ionic current, electrical resistance, or electrical voltage drop across the nanopore.

4. The method of claim 3, wherein the value measured in operation (d) comprises a standard deviation of the noise.

5. The method of claim 1, wherein the value measured in operation (d) is at least based on M nucleotides of the single-stranded portion of the polynucleotide and D pairs of hybridized nucleotides of the extended duplex, wherein M is greater than or equal to two, and wherein D is greater than or equal to one.

6. The method of claim 5, wherein M is greater than or equal to three.

7. The method of claim 5, wherein D is greater than or equal to two.

8. The method of claim 5, wherein at least one of the M nucleotides of the single-stranded portion comprises a modified base, the method comprising identifying the modified base using the value measured in operation (d).

9. The method of claim 8, wherein the modified base comprises a methylated base.

10. The method of claim 1, further comprising:

(f) applying a modified force again disposing the 3' end of the extended duplex within the aperture, and while applying the modified force:

inhibiting, using the nanopore, translocation of the 3' end of the extended duplex to the second side of the nanopore; and measuring a value of an electrical property of the 3' end of the extended duplex and a single-stranded portion of the polynucleotide; and (g) identifying the natural nucleotide using the value measured in operation (f).

11. The method of claim 1, further comprising, after operation (d):

dissociating the extended duplex from the polynucleotide; and hybridizing a second primer to the primer binding sequence of the polynucleotide to form a new duplex with the polynucleotide on the first side of the nanopore, the new duplex including a new 3' end corresponding to a 3' end of the second primer polynucleotide.

12. The method of claim 1, wherein the nanopore comprises a solid-state nanopore.

13. The method of claim 1, wherein the nanopore comprises a biological nanopore.

14. The method of claim 13, wherein the biological nanopore comprises MspA.

15. The method of claim 1, wherein the polynucleotide comprises RNA.

16. The method of claim 1, wherein the polynucleotide comprises DNA.

17. A sequencing system, comprising:

a nanopore comprising a first side, a second side, and an aperture extending through the first and second sides;

a polynucleotide disposed through the aperture of the nanopore such that a 3' end of the polynucleotide is on the first side of the nanopore, and a 5' end of the polynucleotide is on the second side of the nanopore;

a primer hybridized to a primer binding sequence in the polynucleotide to form a duplex disposed on the first side of the nanopore, the duplex including a 3' end corresponding to a 3' end of the primer and at which a natural nucleotide is disposed; and circuitry configured to:

apply a force disposing the 3' end of the duplex within the aperture;

measure a value of an electrical property of the 3' end of the duplex and a single-stranded portion of the polynucleotide while applying the force; and identify the natural nucleotide using the measured value, wherein the nanopore inhibits translocation of the 3' end of the duplex to the second side of the nanopore while the force is applied.

18. The system of claim 17, wherein the value measured by the circuitry comprises an electrical current, ionic current, electrical resistance, or electrical voltage drop across the nanopore.

19. The system of claim 17, wherein the value measured by the circuitry comprises noise of an electrical current, ionic current, electrical resistance, or electrical voltage drop across the nanopore.

20. The system of claim 19, wherein the value measured by the circuitry comprises a standard deviation of the noise.

21. The system of claim 17, wherein the value measured by the circuitry is at least based on M nucleotides of the single-stranded portion of the polynucleotide and D pairs of hybridized nucleotides of the duplex, wherein M is greater than or equal to two, and wherein D is greater than or equal to one.

22. The system of claim 21, wherein M is greater than or equal to three.

23. The system of claim 21, wherein D is greater than or equal to two.

24. The system of claim 21, wherein at least one of the M nucleotides of the single-stranded portion comprises a modified base, the circuitry being configured to identify the modified base using the value measured by the circuitry.

25. The system of claim 24, wherein the modified base comprises a methylated base.

26. The system of claim 17, wherein the circuitry further is configured to:

apply a modified force again disposing the 3' end of the duplex within the aperture;

measure a value of an electrical property of the 3' end of the duplex and a single-stranded portion of the polynucleotide while applying the modified force; and identify the natural nucleotide using the measured value, wherein the nanopore inhibits translocation of the 3' end of the duplex to the second side of the nanopore while the modified force is applied.

27. The system of claim 17, wherein the circuitry is configured to, after applying the force, dissociate the duplex from the polynucleotide.

28. The system of claim 17, wherein the nanopore comprises a solid-state nanopore.

29. The system of claim 17, wherein the nanopore comprises a biological nanopore.

30. The system of claim 29, wherein the biological nanopore comprises MspA.

31. The system of claim 17, wherein the polynucleotide comprises RNA.

32. The system of claim 17, wherein the polynucleotide comprises DNA.

* * * * *